US008063018B2

(12) United States Patent
Ni et al.

(10) Patent No.: US 8,063,018 B2
(45) Date of Patent: Nov. 22, 2011

(54) BIVALENT THROMBIN BINDING MOLECULES COMPRISING LINKERS

(75) Inventors: Feng Ni, Pierrefonds (CA); Dmitri Tolkatchev, La Prairie (CA); Zhengding Su, St. Laurent (CA)

(73) Assignee: National Research Council of Canada, Ottawa (CA)

( * ) Notice: Subject to any disclaimer, the term of this patent is extended or adjusted under 35 U.S.C. 154(b) by 1319 days.

(21) Appl. No.: 11/630,462

(22) PCT Filed: Jun. 20, 2005

(86) PCT No.: PCT/CA2005/000951
§ 371 (c)(1),
(2), (4) Date: Dec. 22, 2006

(87) PCT Pub. No.: WO2006/000081
PCT Pub. Date: Jan. 5, 2006

(65) Prior Publication Data
US 2009/0105116 A1  Apr. 23, 2009

Related U.S. Application Data

(60) Provisional application No. 60/581,703, filed on Jun. 23, 2004.

(51) Int. Cl.
*A61K 38/16* (2006.01)
*C07K 14/00* (2006.01)

(52) U.S. Cl. .......................................... 514/12; 530/350
(58) Field of Classification Search .......................... None
See application file for complete search history.

(56) References Cited

U.S. PATENT DOCUMENTS

| 5,674,838 A | 10/1997 | Obermeier et al. |
| 6,127,337 A * | 10/2000 | Konishi et al. ............... 514/13.6 |
| 6,225,100 B1 | 5/2001 | Maurina-Brunker et al. |
| 6,533,819 B1 | 3/2003 | Urry et al. |

FOREIGN PATENT DOCUMENTS

| EP | 372670 A2 | 6/1990 |
| WO | 94/25491 A1 | 11/1994 |
| WO | 03/057258 A2 | 7/2003 |
| WO | 2004/076484 A1 | 9/2004 |

OTHER PUBLICATIONS

International Search Report on PCT/CA05/000951 dated Oct. 26, 2005.
Office Action on European Application 05759242.0 dated May 11, 2009.
Supplemental Search on European Application 05759242.0 dated May 26, 2009.
Office Action on European Application 05759242.0 dated May 12, 2010.
Anderson,P.J.; Nesset,A.; Dharmawardana, K.R.; and Bock,P.E., 2000, Characterization of proexosile I on prothrombin: J. Biol. Chem., 275, 16428-16434.

Bright,J.N., Woolf,T.B., Hoh,J.H., 2001, Predicting properties of intrinsically unstructured proteins. Prog. Biophys. Mol. Biol., 76, 131-173.
Burbelo, P. D., Drechsel, D., and Hall, A., 1995, A conserved binding motif defines numerous candidate target proteins for both Cdc42 and Rac GTPases: J Biol. Chem. 270, 29071-29074.
Dennis, M. S., Zhang, M., Meng, Y. G., Kadkhodayan, M., Kirchhofer, D., Combs, D., and Damico, L. A., 2002, Albumin binding as a general strategy for improving the pharmacokinetics of proteins: J.Biol.Chem., 277, 35035-35043.
Diella, F., Cameron, S., Gemund, C., Linding, R., Via, A., Kuster, B., Sicheritz-Ponten, T., Blom, N., and Gibson, T. J., 2004, Phospho. ELM: a database of experimentally verified phosphorylation sites in eukaryotic proteins: BMC. Bioinformatics., 5, 79.
DiMaio, J., Gibbs, B., Munn, D., Lefebvre, J., Ni, F., and Konishi, Y., 1990, Bifunctional thrombin inhibitors based on the sequence of hirudin45-65: J.Biol.Chem., 265, 21698-21703.
Gill, S. C. and von Hippel, P. H., 1989, Calculation of protein extinction coefficients from amino acid sequence data: Anal.Biochem., 182, 319-326. Gizachew, D. and Oswald, R. E., 2001, Concerted motion of a protein-peptide complex: backbone dynamics studies of an (15)N-labeled peptide derived from P(21)-activated kinase bound to Cdc42Hs.GMPPCP: Biochemistry 40, 14368-14375.
Hamad-Schifferli, K., Schwartz, J. J., Santos, A. T., Zhang, S., and Jacobson, J. M., 2002, Remote electronic control of DNA hybridization through inductive coupling to an attached metal nanocrystal antenna: Nature, 415, 152-155.
Hilpert, K., Hansen, G., Wessner, H., Kuttner, G., Welfle, K., Seifert, M., and Hohne, W., 2001, Anti-c-myc antibody 9E10: epitope key positions and variability characterized using peptide spot synthesis on cellulose : Protein Eng, 14, 803-806.
Holland S. et al. EBI Dbfetch accession No. AAN21177, Sep. 25, 2002.
Jordan, Andreas, Scholz, Regina, Wust, Peter, Fahling, Horst, and Roland, Felix, 1999, Magnetic fluid hyperthermia (MFH): Cancer treatment with AC magnetic field induced excitation of biocompatible superparamagnetic nanoparticles: Journal of Magnetism and Magnetic Materials, 201, 413-419.

(Continued)

Primary Examiner — Ruixiang Li
(74) Attorney, Agent, or Firm — Hans Koenig

(57) ABSTRACT

There is provided herein a multivalent binding molecule and uses thereof. The molecule is useful in binding a target under certain conditions and releasing it under other conditions. The molecule has the general formula (1) of BM1-L-(BM2)$_n$ (1) wherein, BM1 is a binding moiety 1 having an affinity for site 1 on the target, BM2 is a binding moiety 2 having an affinity for a site other than site 1 on the target, n is 1 or greater, and L is a linker joining BM1 and BM2, said linker being adapted to respond to a change in its environment with a change in conformation and/or flexibility, wherein BM1 and BM2 may be the same or different and are selected such that in use each of the BM1 and BM2 existing separately has a lower binding affinity then the complex of BM1 and BM2 does when they are linked to form the molecule. BM2 may have a single binding region or multiple binding regions with affinity for the target. The binding affinity of BM1 or BM2 to the target alone is no more than ½ the binding affinity of the molecule of formula (1). The molecule of formula (1) can be constructed using an oligomeric or polymeric linker, such as a polypeptide sequence. Such molecules can be useful in the delayed release of drugs, in screening assays, for stabilizing enzymes such as proteases, and for controlling reactions such as blood clotting.

7 Claims, 46 Drawing Sheets

OTHER PUBLICATIONS

Figure 1A:
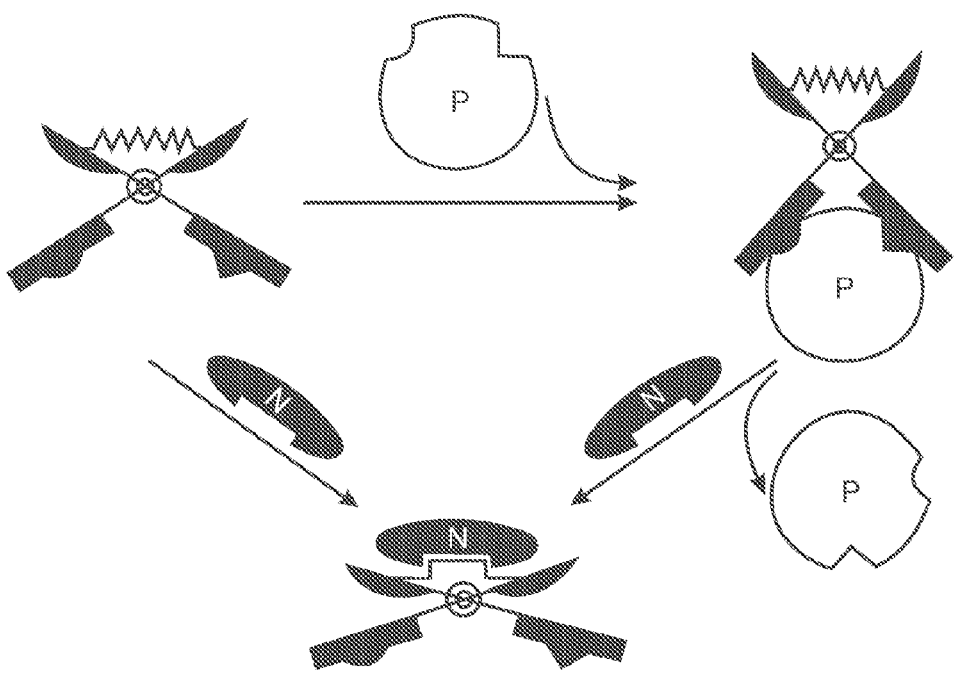

Leonard, D. A., Satoskar, R. S., Wu, W. J., Bagrodia, S., Cerione, R. A., and Manor, D., 1997, Use of a fluorescence spectroscopic readout to characterize the interactions of Cdc42Hs with its target/effector, mPAK-3: Biochemistry 36, 1173-1180.

Lin, Y., Padmapriya, A., Morden, K. M., and Jayasena, S. D., 1995, Peptide conjugation to an in vitro-selected DNA ligand improves enzyme inhibition: Proc.Natl.Acad.Sci.U.S.A, 92, 11044-11048.

McPherson, D. T., Morrow, C., Minehan, D. S., Wu, J., Hunter, E., and Urry, D. W., 1992, Production and purification of a recombinant elastomeric polypeptide, G-(VPGVG)19-VPGV, from *Escherichia coli*: Biotechnol.Prog., 8, 347-352.

Miyawakl A, et al. 1997. Nature. vol. 388, 882-887.

Ni, F., Ning, Q., Jackson, C.M., and Fenton, J.W., 1993, Thrombin exosite for fibrinogen recognition is partially accessible in prothrombin: J. Biol. Chem., 268, 16899-16902.

Nomanbhoy, T. and Cerione, R. A., 1999, Fluorescence assays of Cdc42 interactions with target/effector proteins: Biochemistry 38, 15878-15884.

Osborne, M. J., Su, Z., Sridaran, V., and Ni, F., 2003, Efficient expression of isotopically labeled peptides for high resolution NMR studies: application to the Cdc42/Rac binding domains of virulent kinases in Candida albicans: J Biomol. NMR 26, 317-326.

Pawson, T. and Linding, R., 2005, Synthetic modular systems—reverse engineering of signal transduction: FEBS Lett., 579, 1808-1814.

Pawson, T. and Nash, P., 2003, Assembly of cell regulatory systems through protein interaction domains: Science, 300, 445-452.

Petitjean A, et al. 2004. J. Am. Chem. Soc. 126, 6637-6647.

Polonelli,L.; Magliani,W.; Conti,S.; Bracci,L.; Lozzi,L.; Neri,P.; Adriani,D.; De Bernardis,F.; Cassone,A., 2003, Therapeutic activity of an engineered synthetic killer antiidiotypic antibody fragment against experimental mucosal and systemic candidiasis: Infect. Immun. 71, 6205-6212.

Puntervoll P, et al. 2003, ELM server: A new resource for investigating short functional sites in modular eukaryotic proteins: Nucleic Acids Res., 31, 3625-3630.

Rudolph, M. G., Bayer, P., Abo, A., Kuhlmann, J., Vetter, I. R., and Wittinghofer, A., 1998, The Cdc42/Rac interactive binding region motif of the Wiskott Aldrich syndrome protein (WASP) is necessary but not sufficient for tight binding to Cdc42 and structure formation: J Biol. Chem. 273, 18067-18076.

Slon-Usakiewicz, J. J., Sivaraman, J., Li,Y., Cygler, M., and Konishi, Y., 2000, Design of P1' and P3' residues of trivalent thrombin inhibitors and their crystal structures: Biochemistry, 39, 2384-2391.

Su,Z.; Vinogradova,A.; Koutychenko,A.; Tolkatchev,D.; and Ni,F., 2004a, Rational design and selection of bivalent peptide ligands of thrombin incorporating P4-P1 tetrapeptide sequences: from good substrates to potent inhibitors: Protein Eng. Des. Sel., 17, 647-657.

Su, Z., Xu, P., and Ni, F., 2004b, Single phosphorylation of Tyr304 in the cytoplasmic tail of ephrin B2 confers high-affinity and bifunctional binding to both the SH2 domain of Grb4 and the PDZ domain of the PDZ-RGS3 protein: Eur.J. Biochem., 271, 1725-1736.

Thompson, G., Owen, D., Chalk, P. A., and Lowe, P. N., 1998, Delineation of the Cdc42/Rac-binding domain of p21-activated kinase: Biochemistry 37, 7885-7891.

Tolkatchev, D., Xu, P., and Ni, F., 2003a, Probing the kinetic landscape of transient peptide-protein interactions by use of peptide (15)n NMR relaxation dispersion spectroscopy: binding of an antithrombin peptide to human prothrombin: J. Am.Chem.Soc., 125, 12432-12442.

Tolkatchev D, et al. 2005. Understanding Biology Using Peptides, Blondelle S, ed. (American Peptide Society) pp. 669-670.

Tolkatchev D, et al. 2005. Bioorganic and Medicinal Chemistry Letters. 15, 5120-5123.

Truong, K. Sawano, A., Mizuno, H., Hama, H., Tong, K. I., Mal, T. K., Miyawaki, A., and Ikura, M., 2001, FRET-based in vivo Ca2+ imaging by a new calmodulin-GFP fusion molecule: Nat.Struct.Biol., 8, 1069-1073.

Urry, D. W., 1997, Physical Chemistry of Biological Free Energy Transduction As Demonstrated by Elastic Protein-Based Polymers: J.Phys.Chem.B., 101, 11007-11028.

Witting,J.I., Bourdon,P., Brezniak,D.V., Maraganore,J.M. and Fenton,J.W., 1992, Thrombin-specific inhibition by and slow cleavage of hirulog-1: Biochem. J., 283 ( Pt 3), 737-743.

Wood DW, et al. 2000. Biotechnol. Progr. 16(6), 1055-1063.

Pirone, D.M., Carter, D.E., and Burbelo, P.D. 2001, Evolutionary Expansion of CRIB-Containing Cdc42 Effector Proteins. Trends in Genetics, 17, 370-373.

Li, S.C., Gish, G., Yang, D., Coffey, A.J., Forman-Kay, J.D., Ernberg, I., Kay, L.E. and Pawson, T. 1999, Novel Mode of Ligand Binding by the SH2 Domain of the Human XLP Disease Gene Product SAP/SH2D1A. Curr. Biol. 9, 1355-1362.

Covic, J., Gresser, A.L., Talavera, J., Swift, S., and Kuliopulos, A. 2002, Activation and Inhibition of G Protein-Coupled Receptors by Cell-Penetrating Membrane-Tethered Peptides. Proc. Natl. Acad. Sci., 99, 643-648.

* cited by examiner

CaM-DTI:

*WDPRPQRH*ADQLTEEQIAEFKEAFSLFDKDGDGTITTKELGTVMRSLGQN
PTEAELQDMINEVDADGNGTIDFPEFLTMMARKMKDTGGVKLIPSWTTVI
LVKSMLRKRSFGNPFGGDSEEEIREAFRVFDKGNGYISAAELRHVMTNL
GEKLTDEEVDEMIREADIDGDGQVNYEEFVQMMTAK*DFEEIPEEYLQ*

CaM-DTI2:

*IRFTDGEG*ADQLTEEQIAEFKEAFSLFDKDGDGTITTKELGTVMRSLGQNP
TEAELQDMINEVDADGNGTIDFPEFLTMMARKMKDNGGVKLIPSWTTVIL
VKSMLRKRSFGNPFGGDSEEEIREAFRVFDKDGNGYIRAAELRHVMTNLG
EKLTDEEVDEMIREADIDGDGQVNYEEFVQMMTAK*DFEEIPEEYLQ*

Figure 9

SEQUENCE LISTING

<160> NUMBER OF SEQ ID NOS: 143

<210> SEQ ID NO 1
<211> LENGTH: 12
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 1

Gly Asp Phe Glu Glu Ile Pro Glu Glu Tyr Leu Gln
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Asp Phe Glu Glu Ile Pro Glu Glu Tyr Leu Gln
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Asp Phe Glu Glu Ile Pro Glu Glu Tyr Leu Gln
 1               5                  10

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 4

Arg Xaa Gly Cys
 1

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Gly Ser Gly Ser Gly Ser Gly Ser Gly Ser Gly Ser Gly
 1               5                  10                  15

Ser Gly Asp Phe Glu Glu Ile Pro Glu Glu Tyr Leu Gln
                 20                  25

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic

```
                                peptide
<220> FEATURE:
<221> NAME/KEY: MOD_RES
<222> LOCATION: (2)
<223> OTHER INFORMATION: D-Pip

<400> SEQUENCE: 6

Arg Xaa Gly Cys
  1

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Ser Gly Ser Gly Ser Gly Ser Gly Ser Gly Ser Gly Ser Gly
  1               5                   10                  15

Ser Gly Asp Phe Glu Glu Ile Pro Glu Glu Tyr Leu Gln
             20                  25

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Pro His Tyr Glu Lys Val Ser Gly
  1               5

<210> SEQ ID NO 9
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip
<220> FEATURE:
<221> NAME/KEY: MOD_RES
<222> LOCATION: (7)
<223> OTHER INFORMATION: Tyr or O-phosphotyrosine

<400> SEQUENCE: 9

Arg Xaa Gly Ser Pro His Xaa Glu Lys Val Ser Gly Asp Phe Glu Glu
  1               5                   10                  15

Ile Pro Glu Glu Tyr Leu Gln
             20

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip
<220> FEATURE:
```

```
<221> NAME/KEY: MOD_RES
<222> LOCATION: (7)
<223> OTHER INFORMATION: O-phosphotyrosine

<400> SEQUENCE: 10

Arg Xaa Gly Ser Pro His Xaa Glu Lys Val Ser Gly Asp Phe Glu Glu
 1               5                  10                  15

Ile Pro Glu Glu Tyr Leu Gln
            20

<210> SEQ ID NO 11
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 11

Arg Xaa Gly Ser Pro His Tyr Glu Lys Val Ser Gly Asp Phe Glu Glu
 1               5                  10                  15

Ile Pro Glu Glu Tyr Leu Gln
            20

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Gln Lys Leu Ile Ser Glu Glu Asp Leu
 1               5                  10

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 13

Arg Xaa Gly Glu Gln Lys Leu Ile Ser Glu Glu Asp Leu Gly Asp Phe
 1               5                  10                  15

Glu Glu Ile Pro Glu Glu Tyr Leu Gln
            20                  25

<210> SEQ ID NO 14
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip
```

```
<220> FEATURE:
<221> NAME/KEY: MOD_RES
<222> LOCATION: (7)
<223> OTHER INFORMATION: O-phosphotyrosine
<220> FEATURE:
<221> NAME/KEY: MOD_RES
<222> LOCATION: (16)
<223> OTHER INFORMATION: O-phosphotyrosine

<400> SEQUENCE: 14

Arg Xaa Gly Ser Pro His Xaa Glu Lys Val Ser Gly Ser Pro His Xaa
 1               5                  10                  15

Glu Lys Val Ser Gly Asp Phe Glu Glu Ile Pro Glu Glu Tyr Leu Gln
            20                  25                  30

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 15

Arg Xaa Gly Cys
 1

<210> SEQ ID NO 16
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Asp Lys Asn Ala Asp Gly Trp Ile Asp Asn Gly Asp Phe Glu Glu
 1               5                  10                  15

Ile Pro Glu Glu Tyr Leu Gln
            20

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Lys Asn Ala Asp Gly Trp Ile Asp Asn Gly Asp Phe Glu
 1               5                  10

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Asp Pro Arg Pro Gln Arg His Asn Asp Gly Asp Phe Glu Glu Ile
 1               5                  10                  15
```

```
Pro Glu Glu Tyr Leu Gln
            20

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Trp Asp Pro Arg Pro Gln Arg His
 1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Phe Glu Glu Ile Pro Glu Glu Tyr Leu Gln
 1               5                  10

<210> SEQ ID NO 21
<211> LENGTH: 197
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 21

Trp Asp Pro Arg Pro Gln Arg His Ala Asp Gln Leu Thr Glu Glu Gln
 1               5                  10                  15

Ile Ala Glu Phe Lys Glu Ala Phe Ser Leu Phe Asp Lys Asp Gly Asp
                20                  25                  30

Gly Thr Ile Thr Thr Lys Glu Leu Gly Thr Val Met Arg Ser Leu Gly
            35                  40                  45

Gln Asn Pro Thr Glu Ala Glu Leu Gln Asp Met Ile Asn Glu Val Asp
        50                  55                  60

Ala Asp Gly Asn Gly Thr Ile Asp Phe Pro Glu Phe Leu Thr Met Met
 65                  70                  75                  80

Ala Arg Lys Met Lys Asp Thr Gly Gly Val Lys Leu Ile Pro Ser Trp
                85                  90                  95

Thr Thr Val Ile Leu Val Lys Ser Met Leu Arg Lys Arg Ser Phe Gly
            100                 105                 110

Asn Pro Phe Gly Gly Asp Ser Glu Glu Glu Ile Arg Glu Ala Phe Arg
        115                 120                 125

Val Phe Asp Lys Asp Gly Asn Gly Tyr Ile Ser Ala Ala Glu Leu Arg
130                 135                 140

His Val Met Thr Asn Leu Gly Glu Lys Leu Thr Asp Glu Glu Val Asp
145                 150                 155                 160

Glu Met Ile Arg Glu Ala Asp Ile Asp Gly Asp Gly Gln Val Asn Tyr
                165                 170                 175

Glu Glu Phe Val Gln Met Met Thr Ala Lys Asp Phe Glu Glu Ile Pro
            180                 185                 190

Glu Glu Tyr Leu Gln
            195
```

```
<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Arg Phe Thr Asp Gly Glu Gly Thr Pro Lys Pro Gln Ser His Asn
 1               5                  10                  15

Asp Gly Asp Phe Glu Glu Ile Pro Glu Glu Tyr Leu Gln
            20                  25

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Arg Phe Thr Asp Gly Glu Gly Thr Pro Asn Pro Glu Ser His Asn
 1               5                  10                  15

Asn Gly Asp Phe Glu Glu Ile Pro Glu Glu Tyr Leu Gln
            20                  25

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Lys Val Thr Met Thr Cys Ser Ala Ser
 1               5                  10

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Arg Phe Thr Asp Gly Ala Lys Val Thr Met Thr Cys Ser Ala Ser
 1               5                  10                  15

Gly Asp Phe Glu Glu Ile Pro Glu Glu Tyr Leu Gln
            20                  25

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
```

```
<222> LOCATION: (5)..(6)
<223> OTHER INFORMATION: Variable amino acid
<220> FEATURE:
<221> NAME/KEY: MOD_RES
<222> LOCATION: (8)
<223> OTHER INFORMATION: Variable amino acid
<220> FEATURE:
<221> NAME/KEY: MOD_RES
<222> LOCATION: (10)..(11)
<223> OTHER INFORMATION: Variable amino acid
<220> FEATURE:
<221> NAME/KEY: MOD_RES
<222> LOCATION: (15)
<223> OTHER INFORMATION: Variable amino acid

<400> SEQUENCE: 26

Ile Ser Xaa Pro Xaa Xaa Phe Xaa His Xaa Xaa His Val Gly Xaa Asp
 1               5                   10                  15

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Gly Ser Gly
 1

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Lys Ser Leu Thr Ile Tyr Ala Gln Val Gln Lys
 1               5                   10

<210> SEQ ID NO 29
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip
<220> FEATURE:
<221> NAME/KEY: MOD_RES
<222> LOCATION: (7)
<223> OTHER INFORMATION: O-phosphotyrosine

<400> SEQUENCE: 29

Arg Xaa Gly Ser Pro His Xaa Glu Lys Val Ser Gly Asp Phe Glu Glu
 1               5                   10                  15

Ile Pro Glu Glu Tyr Leu Gln
            20

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 30

Gly Ser Val Val Pro Arg Pro Gln Leu His Asn Asp Gly Asp Phe Glu
1               5                   10                  15

Glu Ile Pro Glu Glu Tyr Leu Gln
            20

<210> SEQ ID NO 31
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser His Ala Pro Arg Pro Gln Ile His Asn Asp Gly Asp Phe Glu
1               5                   10                  15

Glu Ile Pro Glu Glu Tyr Leu Gln
            20

<210> SEQ ID NO 32
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 32

Arg Xaa Gly Ser Val Val Pro Arg Pro Gln Leu His Asn Asp Gly Asp
1               5                   10                  15

Phe Glu Glu Ile Pro Glu Glu Tyr Leu Gln
            20                  25

<210> SEQ ID NO 33
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 33

Arg Xaa Gly Ser His Ala Pro Arg Pro Gln Ile His Asn Asp Gly Asp
1               5                   10                  15

Phe Glu Glu Ile Pro Glu Glu Tyr Leu Gln
            20                  25

<210> SEQ ID NO 34
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)

```
<223> OTHER INFORMATION: Variable amino acid
<220> FEATURE:
<221> NAME/KEY: MOD_RES
<222> LOCATION: (10)..(11)
<223> OTHER INFORMATION: Variable amino acid

<400> SEQUENCE: 34

Gly Ser Val Val Pro Asn Xaa Xaa Leu Xaa Xaa Asp Gly Asp Phe Glu
 1               5                  10                  15

Glu Ile Pro Glu Glu Tyr Leu Gln
            20

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 35

Arg Xaa Gly
 1

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Asp Phe Glu Glu Ile Pro Glu Glu Tyr Leu Gln
 1               5                  10

<210> SEQ ID NO 37
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Asn Ser Gly Val Ser Gly Pro Ile Asn Phe Thr His Lys Val
 1               5                  10                  15

His Val Gly Phe Asp Pro Ala Ser Gly Asn Phe Thr Gly Leu Pro Asp
            20                  25                  30

Thr Trp Lys Ser Leu Leu Gln His Ser Lys Ile Thr
        35                  40

<210> SEQ ID NO 38
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Val Asn Ile Lys Ile Ser Thr Pro Phe Asn Ala Lys His Leu Ala
 1               5                  10                  15
```

```
His Val Gly Ile Asp Asp Asn Gly Ser Tyr Thr Gly Leu Pro Ile Glu
            20                  25                  30

Trp Glu Arg Leu Leu Ser Ala Ser Gly Ile Thr
            35                  40
```

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Thr Leu Asp Leu Asn Thr Pro Val Asp Lys Thr Ser Asn
1               5                   10
```

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Ser Val Val Pro Arg Pro Gln Leu His Asn Asp
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Ser His Ala Pro Arg Pro Gln Ile His Asn Asp
1               5                   10
```

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Asn Gly Arg Lys Ile Cys Leu Asp Leu Gln Ala Pro Leu Tyr Lys Lys
1               5                   10                  15

Ile Ile Lys Lys Leu Leu Glu Ser
            20
```

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Asn Gly Arg Lys Ile Cys Leu Glu Leu Arg Ala Pro Leu Tyr Lys Lys
1               5                   10                  15

Ile Ile Lys Lys Leu Leu Glu Ser
```

```
<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

His His Leu Gly Gly Ala Lys Gln Ala Gly Asp Val
 1               5                  10

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Met Glu Ser Arg Ala Asp Arg
 1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser His Asn Arg
 1               5

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Gly Ser Gly Ser Gly Ser Gly Ser Gly Ser Gly Ser Gly
 1               5                  10                  15

Ser Gly

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Asp Lys Asn Ala Asp Gly Trp Ile Asp Asn
 1               5                  10

<210> SEQ ID NO 49
<211> LENGTH: 14
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 49

Asp Lys Asn Ala Asp Gly Trp Ile Asp Asn Gly Glu Phe Glu
1               5                   10

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ser Gly Ser
1

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Ser Gly Ser Gly Ser Gly Ser
1               5

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ser Gly Ser Gly Ser Gly Ser Gly Ser Gly Ser
1               5                   10

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Gly Ser Gly Ser Gly Ser Gly Ser Gly Ser Gly Ser Gly Ser
1               5                   10                  15

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Gly Ser Gly Ser Gly Ser Gly Ser Gly Ser Gly Ser Gly Ser
1               5                   10                  15

Gly Ser Gly Ser
            20

```
<210> SEQ ID NO 55
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ser Gly Ser Gly Ser Gly Ser Gly Ser Gly Ser Gly Ser Gly Ser
 1               5                  10                  15

Gly Ser Gly Ser Gly Ser Gly Ser
            20

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Ser Gly Ser Gly Ser Gly Ser Gly Ser Gly Ser Gly Ser Gly Ser
 1               5                  10                  15

Gly Ser Gly Ser Gly Ser Gly Ser Gly Ser Gly Ser
            20                  25

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Gly Ser Gly Ser Gly Ser Gly Ser Gly Ser Gly Ser Gly Ser Gly
 1               5                  10                  15

Ser

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser Gly Ser Gly Ser Gly Ser Gly Lys Gly Ser Gly Ser Gly Ser
 1               5                  10                  15

Gly Ser Gly Ser
            20

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Pro His Tyr Glu Lys Val Ser Gly
```

```
<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Pro His Tyr Glu Lys Val Ser Gly Ser Pro His Tyr Glu Lys Val
 1               5                  10                  15

Ser Gly

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: O-phosphotyrosine

<400> SEQUENCE: 61

Ser Pro His Xaa Glu Lys Val Ser Gly
 1               5

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: O-phosphotyrosine
<220> FEATURE:
<221> NAME/KEY: MOD_RES
<222> LOCATION: (13)
<223> OTHER INFORMATION: O-phosphotyrosine

<400> SEQUENCE: 62

Ser Pro His Xaa Glu Lys Val Ser Gly Ser Pro His Xaa Glu Lys Val
 1               5                  10                  15

Ser Gly

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro His Tyr Glu Lys Val Ser
 1               5

<210> SEQ ID NO 64
<211> LENGTH: 16
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 64

Pro His Tyr Glu Lys Val Ser Gly Ser Pro His Tyr Glu Lys Val Ser
1               5                   10                  15

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: O-phosphotyrosine

<400> SEQUENCE: 65

Pro His Xaa Glu Lys Val Ser
1               5

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: O-phosphotyrosine
<220> FEATURE:
<221> NAME/KEY: MOD_RES
<222> LOCATION: (12)
<223> OTHER INFORMATION: O-phosphotyrosine

<400> SEQUENCE: 66

Pro His Xaa Glu Lys Val Ser Gly Ser Pro His Xaa Glu Lys Val Ser
1               5                   10                  15

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Variable natural amino acid
<220> FEATURE:
<221> NAME/KEY: MOD_RES
<222> LOCATION: (9)..(10)
<223> OTHER INFORMATION: Variable natural amino acid

<400> SEQUENCE: 67

Ser Val Val Pro Asn Xaa Xaa Leu Xaa Xaa Asp
1               5                   10

<210> SEQ ID NO 68
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (2)
<223> OTHER INFORMATION: D-Pip

<400> SEQUENCE: 68

Arg Xaa
 1

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Arg Phe Thr Asp Gly Glu Gly Thr Pro Lys
 1               5                  10

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Arg Phe Thr Asp
 1               5

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Arg Phe Thr Asp Gly Glu Gly Thr Pro Asn
 1               5                  10

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Arg Phe Thr Asp
 1               5

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 73

Arg Xaa Gly Ser Gly Ser Gly Asp Phe Glu Glu Ile Pro Glu Glu Tyr
```

Leu Gln

<210> SEQ ID NO 74
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 74

Arg Xaa Gly Ser Gly Ser Gly Ser Gly Ser Gly Asp Phe Glu Glu Ile
 1               5                   10                  15

Pro Glu Glu Tyr Leu Gln
            20

<210> SEQ ID NO 75
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 75

Arg Xaa Gly Ser Gly Ser Gly Ser Gly Ser Gly Ser Gly Ser Gly Asp
 1               5                   10                  15

Phe Glu Glu Ile Pro Glu Glu Tyr Leu Gln
            20                  25

<210> SEQ ID NO 76
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 76

Arg Xaa Gly Ser Gly Ser Gly Ser Gly Ser Gly Ser Gly Ser Gly Ser
 1               5                   10                  15

Gly Ser Gly Asp Phe Glu Glu Ile Pro Glu Glu Tyr Leu Gln
            20                  25                  30

<210> SEQ ID NO 77
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

```
<400> SEQUENCE: 77

Arg Xaa Gly Ser Gly Ser Gly Ser Gly Ser Gly Ser Gly Ser
 1               5                  10                  15

Gly Ser Gly Ser Gly Ser Gly Asp Phe Glu Glu Ile Pro Glu Glu Tyr
            20                  25                  30

Leu Gln

<210> SEQ ID NO 78
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 78

Arg Xaa Gly Ser Gly Ser Gly Ser Gly Ser Gly Ser Gly Ser
 1               5                  10                  15

Gly Ser Gly Ser Gly Ser Gly Ser Gly Asp Phe Glu Glu Ile
            20                  25                  30

Pro Glu Glu Tyr Leu Gln
        35

<210> SEQ ID NO 79
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 79

Arg Xaa Gly Ser Gly Ser Gly Ser Gly Ser Gly Ser Gly Ser
 1               5                  10                  15

Gly Ser Gly Ser Gly Ser Gly Ser Gly Ser Gly Ser Gly Asp
            20                  25                  30

Phe Glu Glu Ile Pro Glu Glu Tyr Leu Gln
        35                  40

<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 80

Arg Xaa Gly Ser Pro His Tyr Glu Lys Val Ser Gly Asp Phe Glu Glu
 1               5                  10                  15

Ile Pro Glu Glu Tyr Leu Gln
            20
```

```
<210> SEQ ID NO 81
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 81

Arg Xaa Gly Ser Pro His Tyr Glu Lys Val Ser Gly Ser Pro His Tyr
 1               5                  10                  15

Glu Lys Val Ser Gly Asp Phe Glu Glu Ile Pro Glu Glu Tyr Leu Gln
            20                  25                  30

<210> SEQ ID NO 82
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip
<220> FEATURE:
<221> NAME/KEY: MOD_RES
<222> LOCATION: (7)
<223> OTHER INFORMATION: O-phosphotyrosine

<400> SEQUENCE: 82

Arg Xaa Gly Ser Pro His Xaa Glu Lys Val Ser Gly Asp Phe Glu Glu
 1               5                  10                  15

Ile Pro Glu Glu Tyr Leu Gln
            20

<210> SEQ ID NO 83
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Cys Gly Ser Gly Ser Gly Ser Gly Ser Gly Ser Gly Ser Gly Ser Gly
 1               5                  10                  15

Ser Gly Asp Phe Glu Glu Ile Pro Glu Glu Tyr Leu Gln
            20                  25

<210> SEQ ID NO 84
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 84

Arg Xaa Gly Ser Gly Ser Gly Ser Gly Ser Lys Gly Ser Gly Ser
 1               5                  10                  15
```

```
Gly Ser Gly Ser Gly Ser Gly Asp Phe Glu Glu Ile Pro Glu Glu Tyr
            20                  25                  30

Leu Gln

<210> SEQ ID NO 85
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 85

Arg Xaa Gly Thr Leu Asp Leu Asn Thr Pro Val Asp Lys Thr Ser Asn
 1               5                  10                  15

Gly Asp Phe Glu Glu Ile Pro Glu Glu Tyr Leu Gln
            20                  25

<210> SEQ ID NO 86
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 86

Arg Xaa Gly Asn Gly Arg Lys Ile Cys Leu Asp Leu Gln Ala Pro Leu
 1               5                  10                  15

Tyr Lys Lys Ile Ile Lys Lys Leu Leu Glu Ser Gly Asp Phe Glu Glu
            20                  25                  30

Ile Pro Glu Glu Tyr Leu Gln
        35

<210> SEQ ID NO 87
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 87

Arg Xaa Gly Asn Gly Arg Lys Ile Cys Leu Glu Leu Arg Ala Pro Leu
 1               5                  10                  15

Tyr Lys Lys Ile Ile Lys Lys Leu Leu Glu Ser Gly Asp Phe Glu Glu
            20                  25                  30

Ile Pro Glu Glu Tyr Leu Gln
        35

<210> SEQ ID NO 88
<211> LENGTH: 27
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 88

Arg Xaa Gly His His Leu Gly Gly Ala Lys Gln Ala Gly Asp Val Gly
 1               5                  10                  15

Asp Phe Glu Glu Ile Pro Glu Glu Tyr Leu Gln
            20                  25

<210> SEQ ID NO 89
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 89

Arg Xaa Gly Tyr Met Glu Ser Arg Ala Asp Arg Gly Asp Phe Glu Glu
 1               5                  10                  15

Ile Pro Glu Glu Tyr Leu Gln
            20

<210> SEQ ID NO 90
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 90

Arg Xaa Gly Gln Ser His Asn Arg Gly Asp Phe Glu Glu Ile Pro Glu
 1               5                  10                  15

Glu Tyr Leu Gln
            20

<210> SEQ ID NO 91
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Cys Asp Lys Asn Ala Asp Gly Trp Ile Asp Asn Gly Asp Phe Glu Glu
 1               5                  10                  15

Ile Pro Glu Glu Tyr Leu Gln
            20

<210> SEQ ID NO 92
<211> LENGTH: 24
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 92

Gly Gly Asn Ser Gly Val Ser Gly Pro Ile Asn Phe Thr His Lys Val
1               5                   10                  15

His Val Gly Phe Asp Pro Ala Ser
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Asn Ser Gly Val Ser Gly Pro Ile Asn Phe Thr His Lys Val
1               5                   10                  15

His Val Gly Phe Asp
            20

<210> SEQ ID NO 94
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Val Asn Ile Lys Ile Ser Thr Pro Phe Asn Ala Lys His Leu Ala
1               5                   10                  15

His Val Gly Ile Asp Asp Asn Gly
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Val Asn Ile Lys Ile Ser Thr Pro Phe Asn Ala Lys His Leu Ala
1               5                   10                  15

His Val Gly Ile Asp
            20

<210> SEQ ID NO 96
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Asn Phe Thr Gly Leu Pro Asp Thr Trp Lys Ser Leu Leu Gln His
1               5                   10                  15

Ser Lys Ile Thr
            20

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Asn Phe Thr Gly Leu Pro Asp Thr Trp Lys Ser Leu Leu Gln His Ser
 1               5                  10                  15

Lys Ile Thr

<210> SEQ ID NO 98
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 98

Gly Ser Tyr Thr Gly Leu Pro Ile Glu Trp Glu Arg Leu Leu Ser Ala
 1               5                  10                  15

Ser Gly Ile Thr
            20

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Ser Tyr Thr Gly Leu Pro Ile Glu Trp Glu Arg Leu Leu Ser Ala Ser
 1               5                  10                  15

Gly Ile Thr

<210> SEQ ID NO 100
<211> LENGTH: 44
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Gly Gly Asn Ser Gly Val Ser Gly Pro Ile Asn Phe Thr His Lys Val
 1               5                  10                  15

His Val Gly Phe Asp Ser Gly Ser Gly Asn Phe Thr Gly Leu Pro Asp
                20                  25                  30

Thr Trp Lys Ser Leu Leu Gln His Ser Lys Ile Thr
            35                  40

<210> SEQ ID NO 101
<211> LENGTH: 52
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Gly Gly Asn Ser Gly Val Ser Gly Pro Ile Asn Phe Thr His Lys Val

```
                1               5                  10                  15
His Val Gly Phe Asp Arg Lys Ser Leu Thr Ile Tyr Ala Gln Val Gln
                    20                  25                  30

Lys Asn Phe Thr Gly Leu Pro Asp Thr Trp Lys Ser Leu Leu Gln His
        35                  40                  45

Ser Lys Ile Thr
    50

<210> SEQ ID NO 102
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 102

Arg Xaa Gly Arg Lys Ser Leu Thr Ile Tyr Ala Gln Val Gln Lys Gly
1               5                   10                  15

Asp Phe Glu Glu Ile Pro Glu Glu Tyr Leu Gln
            20                  25

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Thr Leu Asp Leu Asn Thr Pro Val Asp Lys Thr Ser Asn
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Ser His Ala Pro Arg Pro Gln Ile His Asn Asp
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Ser Val Val Pro Arg Pro Gln Leu His Asn Asp
1               5                   10

<210> SEQ ID NO 106
<211> LENGTH: 13
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 106

Gly His His Leu Gly Gly Ala Lys Gln Ala Gly Asp Val
  1               5                  10

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Tyr Met Glu Ser Arg Ala Asp Arg
  1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gln Ser His Asn Arg
  1               5

<210> SEQ ID NO 109
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Lys Asn Ala Asp Gly Trp Ile Asp Asn Gly Glu Phe Glu
  1               5                  10

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Asp Lys Asn Ala Asp Gly Trp Ile Asp Asn Gly Asp Phe Glu
  1               5                  10

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Leu Ile Glu Asp Ile Cys Leu Pro Arg Trp Gly Cys Leu Trp Glu Asp
  1               5                  10                  15

<210> SEQ ID NO 112

```
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 112

Arg Xaa Gly Leu Ile Glu Asp Ile Cys Leu Pro Arg Trp Gly Cys Leu
 1               5                  10                  15

Trp Glu Asp Gly Asp Phe Gln Gln Ile Pro Glu Glu Tyr Leu Gln
            20                  25                  30

<210> SEQ ID NO 113
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Ser Gly Asp Phe Glu Glu Ile Pro Glu Glu Tyr Leu Gln
 1               5                  10

<210> SEQ ID NO 114
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Asp Lys Asn Ala Asp Gly Trp Ile Asp Asn Gly Asp Phe Glu Glu
 1               5                  10                  15

Ile Pro Glu Glu Tyr Leu Gln
            20

<210> SEQ ID NO 115
<211> LENGTH: 32
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip
<220> FEATURE:
<221> NAME/KEY: MOD_RES
<222> LOCATION: (7)
<223> OTHER INFORMATION: Tyr or O-phosphotyrosine
<220> FEATURE:
<221> NAME/KEY: MOD_RES
<222> LOCATION: (16)
<223> OTHER INFORMATION: Tyr or O-phosphotyrosine

<400> SEQUENCE: 115

Arg Xaa Gly Ser Pro His Xaa Glu Lys Val Ser Gly Ser Pro His Xaa
 1               5                  10                  15

Glu Lys Val Ser Gly Asp Phe Glu Glu Ile Pro Glu Glu Tyr Leu Gln
            20                  25                  30
```

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Ile Arg Phe Thr Asp Gly Glu Gly
 1               5

<210> SEQ ID NO 117
<211> LENGTH: 197
<212> TYPE: PRT
<213> ORGANISM: Artificial Sequence
<220> FEATURE:
<223> OTHER INFORMATION: Description of Artificial Sequence: Synthetic protein construct

<400> SEQUENCE: 117

Ile Arg Phe Thr Asp Gly Glu Gly Ala Asp Gln Leu Thr Glu Glu Gln
 1               5                  10                  15

Ile Ala Glu Phe Lys Glu Ala Phe Ser Leu Phe Asp Lys Asp Gly Asp
                20                  25                  30

Gly Thr Ile Thr Thr Lys Glu Leu Gly Thr Val Met Arg Ser Leu Gly
            35                  40                  45

Gln Asn Pro Thr Glu Ala Glu Leu Gln Asp Met Ile Asn Glu Val Asp
        50                  55                  60

Ala Asp Gly Asn Gly Thr Ile Asp Phe Pro Glu Phe Leu Thr Met Met
 65                  70                  75                  80

Ala Arg Lys Met Lys Asp Asn Gly Gly Val Lys Leu Ile Pro Ser Trp
                85                  90                  95

Thr Thr Val Ile Leu Val Lys Ser Met Leu Arg Lys Arg Ser Phe Gly
                100                 105                 110

Asn Pro Phe Gly Gly Asp Ser Glu Glu Ile Arg Glu Ala Phe Arg
            115                 120                 125

Val Phe Asp Lys Asp Gly Asn Gly Tyr Ile Arg Ala Ala Glu Leu Arg
130                 135                 140

His Val Met Thr Asn Leu Gly Glu Lys Leu Thr Asp Glu Glu Val Asp
145                 150                 155                 160

Glu Met Ile Arg Glu Ala Asp Ile Asp Gly Asp Gly Gln Val Asn Tyr
                165                 170                 175

Glu Glu Phe Val Gln Met Met Thr Ala Lys Asp Phe Glu Glu Ile Pro
            180                 185                 190

Glu Glu Tyr Leu Gln
        195

<210> SEQ ID NO 118
<211> LENGTH: 99
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Val Pro Gly Val Gly Val Pro Gly Val Gly Val Pro Gly Val Gly Val
 1               5                  10                  15

Pro Gly Val Gly Val Pro Gly Val Gly Val Pro Gly Val Gly Val Pro
                20                  25                  30

```
Gly Val Gly Val Pro Gly Val Gly Val Pro Gly Val Gly Val Pro Gly
            35                  40                  45

Val Gly Val Pro Gly Val Gly Val Pro Gly Val Gly Val Pro Gly Val
 50                  55                  60

Gly Val Pro Gly Val Gly Val Pro Gly Val Gly Val Pro Gly Val Gly
 65                  70                  75                  80

Val Pro Gly Val Gly Val Pro Gly Val Gly Val Pro Gly Val Gly Val
             85                  90                  95

Pro Gly Val

<210> SEQ ID NO 119
<211> LENGTH: 114
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 119

Arg Xaa Gly Val Pro Gly Val Gly Val Pro Gly Val Gly Val Pro Gly
 1               5                  10                  15

Val Gly Val Pro Gly Val Gly Val Pro Gly Val Gly Val Pro Gly Val
             20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
 50                  55                  60

Pro Gly Val Gly Val Pro Gly Val Gly Val Pro Gly Val Gly Val Pro
 65                  70                  75                  80

Gly Val Gly Val Pro Gly Val Gly Val Pro Gly Val Gly Val Pro Gly
             85                  90                  95

Val Gly Val Pro Gly Val Gly Asp Phe Glu Glu Ile Pro Glu Glu Tyr
            100                 105                 110

Leu Gln

<210> SEQ ID NO 120
<211> LENGTH: 100
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Val Pro Gly Val Gly Val Pro Gly Val Gly Val Pro Gly Val Gly
 1               5                  10                  15

Val Pro Gly Val Gly Val Pro Gly Val Gly Val Pro Gly Val Gly Val
             20                  25                  30

Pro Gly Val Gly Val Pro Gly Val Gly Val Pro Gly Val Gly Val Pro
            35                  40                  45

Gly Val Gly Val Pro Gly Val Gly Val Pro Gly Val Gly Val Pro Gly
 50                  55                  60

Val Gly Val Pro Gly Val Gly Val Pro Gly Val Gly Val Pro Gly Val
 65                  70                  75                  80

Gly Val Pro Gly Val Gly Val Pro Gly Val Gly Val Pro Gly Val Gly
             85                  90                  95
```

```
Val Pro Gly Val
            100

<210> SEQ ID NO 121
<211> LENGTH: 118
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Arg Phe Thr Asp Gly Glu Gly Val Pro Gly Val Gly Val Pro Gly
  1               5                  10                  15

Val Gly Val Pro Gly Val Gly Val Pro Gly Val Gly Val Pro Gly Val
             20                  25                  30

Gly Val Pro Gly Val Gly Val Pro Gly Val Gly Val Pro Gly Val Gly
         35                  40                  45

Val Pro Gly Val Gly Val Pro Gly Val Gly Val Pro Gly Val Gly Val
     50                  55                  60

Pro Gly Val Gly Val Pro Gly Val Gly Val Pro Gly Val Gly Val Pro
 65                  70                  75                  80

Gly Val Gly Val Pro Gly Val Gly Val Pro Gly Val Gly Val Pro Gly
                 85                  90                  95

Val Gly Val Pro Gly Val Gly Val Pro Gly Val Gly Asp Phe Glu Glu
            100                 105                 110

Ile Pro Glu Glu Leu Gln
        115

<210> SEQ ID NO 122
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pip

<400> SEQUENCE: 122

Arg Xaa Gly
  1

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Ser Pro His Tyr Glu Lys Val Ser
  1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (5)
<223> OTHER INFORMATION: O-phosphotyrosine

<400> SEQUENCE: 124

Gly Ser Pro His Xaa Glu Lys Val Ser
1               5

<210> SEQ ID NO 125
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Ser Pro His Tyr Glu Lys Val Ser Gly Ser Pro His Tyr Glu Lys
1               5                   10                  15

Val Ser

<210> SEQ ID NO 126
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)
<223> OTHER INFORMATION: O-phosphotyrosine
<220> FEATURE:
<221> NAME/KEY: MOD_RES
<222> LOCATION: (14)
<223> OTHER INFORMATION: O-phosphotyrosine

<400> SEQUENCE: 126

Gly Ser Pro His Xaa Glu Lys Val Ser Gly Ser Pro His Xaa Glu Lys
1               5                   10                  15

Val Ser

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Glu Gln Lys Leu Ile Ser Glu Glu Asp Leu
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Arg Lys Ser Leu Thr Ile Tyr Ala Gln Val Gln Lys
1               5                   10

<210> SEQ ID NO 129
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: O-phosphotyrosine

<400> SEQUENCE: 129

Ser Pro His Xaa Glu Lys Val Ser Gly
  1               5

<210> SEQ ID NO 130
<211> LENGTH: 52
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Asn Ser Gly Phe Pro Gly Pro Ile Asn Phe Thr His Lys Val
  1               5                  10                  15

His Val Gly Phe Asp Arg Lys Ser Leu Thr Ile Tyr Ala Gln Val Gln
             20                  25                  30

Lys Asn Phe Thr Gly Leu Pro Asp Thr Trp Lys Ser Leu Leu Gln His
         35                  40                  45

Ser Lys Ile Thr
     50

<210> SEQ ID NO 131
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Tyr Gly Arg Lys Lys Arg Arg Gln Arg Arg Gly Gly Asn Ser Gly
  1               5                  10                  15

Phe Pro Gly Pro Ile Asn Phe Thr His Lys Val His Val Gly Phe Asp
             20                  25                  30

Arg Lys Ser Leu Thr Ile Tyr Ala Gln Val Gln Lys Asn Phe Thr Gly
         35                  40                  45

Leu Pro
     50

<210> SEQ ID NO 132
<211> LENGTH: 113
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Ser Ser His His His His His His Ser Ser Phe Asn Pro Arg Gly
  1               5                  10                  15

Ser Trp Tyr Tyr Gly Asn Val Thr Arg His Gln Ala Glu Cys Ala Leu
             20                  25                  30

Asn Glu Arg Gly Val Glu Gly Asp Phe Leu Ile Arg Asp Ser Glu Ser
         35                  40                  45
```

```
Ser Pro Ser Asp Phe Ser Val Ser Leu Lys Ala Ser Gly Arg Asn Lys
        50                  55                  60

His Phe Lys Val Gln Leu Val Asp Ser Val Tyr Cys Ile Gly Gln Arg
 65                  70                  75                  80

Arg Phe His Ser Met Asp Glu Leu Val Glu His Tyr Lys Lys Ala Pro
                 85                  90                  95

Ile Phe Thr Ser Glu His Gly Glu Lys Leu Tyr Leu Val Arg Ala Leu
            100                 105                 110

Gln

<210> SEQ ID NO 133
<211> LENGTH: 120
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Ser Ser His His His His His Ser Ser Phe Asn Pro Arg Gly
  1               5                  10                  15

Ser Asp Ala Val Ala Val Tyr His Gly Lys Ile Ser Arg Glu Thr Gly
                 20                  25                  30

Glu Lys Leu Leu Leu Ala Thr Gly Leu Asp Gly Ser Tyr Leu Leu Arg
             35                  40                  45

Asp Ser Glu Ser Val Pro Gly Val Tyr Cys Leu Cys Val Leu Tyr His
         50                  55                  60

Gly Tyr Ile Tyr Thr Tyr Arg Val Ser Gln Thr Glu Thr Gly Ser Trp
 65                  70                  75                  80

Ser Ala Glu Thr Ala Pro Gly Val His Lys Arg Tyr Phe Arg Lys Ile
                 85                  90                  95

Lys Asn Leu Ile Ser Ala Phe Gln Lys Pro Asp Gln Gly Ile Val Ile
            100                 105                 110

Pro Leu Gln Tyr Pro Val Glu Lys
        115                 120

<210> SEQ ID NO 134
<211> LENGTH: 197
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Ser Ser His His His His His Ser Ser Gly Leu Val Pro Arg
  1               5                  10                  15

Gly Ser His Met Gln Thr Ile Lys Cys Val Val Val Gly Asp Gly Ala
                 20                  25                  30

Val Gly Lys Thr Cys Leu Leu Ile Ser Tyr Thr Thr Ser Lys Phe Pro
             35                  40                  45

Ala Asp Tyr Val Pro Thr Val Phe Asp Asn Tyr Ala Val Thr Val Met
         50                  55                  60

Ile Gly Asp Glu Pro Phe Thr Leu Gly Leu Phe Asp Thr Ala Gly Gln
 65                  70                  75                  80

Glu Asp Tyr Asp Arg Leu Arg Pro Leu Ser Tyr Pro Ser Thr Asp Val
                 85                  90                  95

Phe Leu Val Cys Phe Ser Val Ile Ser Pro Ala Ser Phe Glu Asn Val
```

```
            100                 105                 110
Lys Glu Lys Trp Phe Pro Glu Val His His Cys Pro Gly Val Pro
        115                 120                 125

Ile Ile Ile Val Gly Thr Gln Thr Asp Leu Arg Asn Asp Val Ile
    130                 135                 140

Leu Gln Arg Leu His Arg Gln Lys Leu Ser Pro Ile Thr Gln Glu Gln
145                 150                 155                 160

Gly Glu Lys Leu Ala Lys Glu Leu Lys Ala Val Lys Tyr Val Glu Cys
                165                 170                 175

Ser Ala Leu Thr Gln Arg Gly Leu Lys Thr Val Phe Asp Glu Ala Ile
            180                 185                 190

Val Ala Ala Leu Glu
        195

<210> SEQ ID NO 135
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tagcgatact gcgtgggttg gggcgggtag ggccagcagt ctcgt           45

<210> SEQ ID NO 136
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gcgccctaaa ctggtggtgg aatgcgtcat gagggcgc                   38

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Asp Phe Glu Gly Ile Pro Glu Glu Tyr Gln
1               5                   10

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Trp Asp Pro Arg Pro Asn Arg His
1               5

<210> SEQ ID NO 139
<211> LENGTH: 44
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 139

Gly Gly Asn Ser Gly Val Ser Gly Pro Ile Asn Phe Thr His Lys Val
 1               5                  10                  15

His Val Gly Phe Asp Pro Ala Ser Gly Ser Tyr Thr Gly Leu Pro Ile
            20                  25                  30

Glu Trp Glu Arg Leu Leu Ser Ala Ser Gly Ile Thr
        35                  40

<210> SEQ ID NO 140
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Glu Val Asn Ile Lys Ile Ser Thr Pro Phe Asn Ala Lys His Leu Ala
 1               5                  10                  15

His Val Gly Ile Asp Asp Asn Gly Asn Phe Thr Gly Leu Pro Asp Thr
            20                  25                  30

Trp Lys Ser Leu Leu Gln His Ser Lys Ile Thr
        35                  40

<210> SEQ ID NO 141
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Glu Val Asn Ile Lys Ile Ser Thr Pro Phe Asn Ala Lys His Leu Ala
 1               5                  10                  15

His Val Gly Ile Asp Pro Asp Asn Gly Asn Phe Thr Gly Leu Pro Asp
            20                  25                  30

Thr Trp Lys Ser Leu Leu Gln His Ser Lys Ile Thr
        35                  40

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Asn Pro Arg Gly Ser Gly Gly Ser Gly Ser Glu Phe Met
 1               5                  10                  15

<210> SEQ ID NO 143
<211> LENGTH: 63
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Tyr Gly Arg Lys Lys Arg Arg Gln Arg Arg Gly Gly Asn Ser Gly
```

-continued

```
  1               5              10              15
Phe Pro Gly Pro Ile Asn Phe Thr His Lys Val His Val Gly Phe Asp
            20                  25                  30

Arg Lys Ser Leu Thr Ile Tyr Ala Gln Val Gln Lys Asn Phe Thr Gly
        35                  40                  45

Leu Pro Asp Thr Trp Lys Ser Leu Leu Gln His Ser Lys Ile Thr
    50                  55                  60
```

BIVALENT THROMBIN BINDING MOLECULES COMPRISING LINKERS

This application is a National Stage application of PCT Application PCT/CA2003/000951 filed Jun. 20, 2005 which claims benefit of U.S. Provisional Application 60/581,703 filed Jun. 23, 2004.

FIELD OF THE INVENTION

The invention relates to the field of multivalent binding molecules containing polymeric linkers.

BACKGROUND TO THE INVENTION

Strategies of linking weak-binding molecular fragments together to produce a significantly stronger ligand molecule have been implemented in drug discovery. Tweezer-like molecules have also been designed recently in the area of host-guest chemistry to control the specific complexation of artificial receptors (hosts) with small molecules (guests). In these applications, the linking bridge is normally optimized and often rigidified to achieve maximal affinity of the bivalent molecule. Bivalent and polyvalent ligands have been reported that incorporate multiple copies of a single binding moiety on a polymer backbone.

It is an object of the invention to provide multivalent binding molecules containing linkers through which binding can be modulated.

SUMMARY OF THE INVENTION

There is disclosed herein an approach combining independent binding moieties in a single molecular structure, which couples binding affinity to an on/off or modulatable switch. This molecular organization provides responsiveness of the inherent ligand (effector/inhibitor) potency to an external triggering signal. A principle of such a molecular structure is the design of the ligand in a bivalent or otherwise multivalent fashion, termed "biomolecular tweezers", which contain two or more binding moieties (or "heads") linked by a structurally flexible bridge (FIG. 1). Each binding moiety in isolation preferably has only low-affinity and transient interactions with an intrinsic dissociation constant preferably less than 1 M for its specific binding site on a target biomacromolecule. When linked together, the resulting bivalent or multivalent ligand makes a substantially stable complex with the target, achieving enhancement of preferably at least two (2) fold in overall binding affinity as compared to the highest affinity of the constituent monovalent ligands. To achieve control of binding, a change (normally, decrease) in the flexibility of the linker can be induced by an external trigger to disrupt the molecule's ability to bind in a bivalent or multivalent high-affinity mode. Vise versa, removal of constraints imposed on the linker would preferably restore the high-affinity binding of the freed bivalent or multivalent ligand. Where the binding sites are known to occur in a defined spatial relationship, it may in some instances be desirable to select a linker which is substantially rigid in the environment in which binding is desired and has a conformation when rigid that places the ligands in preferred positions for binding.

In an embodiment of the invention there is provided a multivalent binding molecule and uses thereof. The molecule is useful in binding a target under certain conditions and releasing it under other conditions. The molecule has the general formula (I) of $$BM1-L-(BM2)_n \quad (1)$$

wherein,
BM1 is a binding moiety 1 having an affinity for site 1 on the target,
BM2 is a binding moiety 2 having an affinity for a site other than site 1 on the target, n is 1 or greater, and
L is a linker joining BM1 and BM2, said linker being adapted to respond to a change in its environment with a change in conformation and/or flexibility, wherein BM1 and BM2 may be the same or different, and when n>1, different BM2 moieties may have affinities for different binding sites on the target. BM1 and BM2 are selected such that in use each of the BM1 and BM2 existing separately has a lower binding affinity then the complex of BM1 and BM2 does when they are linked to form the molecule. BM1 and/or BM2 may each have a single binding region or multiple binding regions with affinity for the target. The binding affinity of BM1 or BM2 to the target alone is no more than ½ the binding affinity of the molecule of formula 1. The molecule of formula 1 can be constructed using an oligomeric or polymeric linker, such as a polypeptide sequence. Such molecules can be useful in the delayed release of drugs, in screening assays, for stabilizing enzymes such as proteases, and for controlling reactions such as blood clotting.

In an embodiment of the invention there is provided a molecule of formula I wherein the amino acid sequence is selected from at least one of SEQ. ID. NO. 8, 12, 17, 24, 27, 28, 37-47, 48, 49, 50-56, 57, 58, 59-60, 124-126, 127, or 128.

In an embodiment of the invention there is provided a molecule of formula I wherein BM1 comprises an amino acid sequence selected from: SEQ. ID. NO. 6, 9, 15, 19, 35, 68, 69-71, 72, 93, 92, 94-95, 116, 122 or linked sequences SEQ. ID. NO. 15 and SEQ. ID. NO. 16.

In an embodiment of the invention there is provided a molecule of formula I wherein BM2 comprises an amino acid sequence selected from SEQ. ID. NO. 1, 20, 36, 96-99.

In an embodiment of the invention there is provided a molecule of formula I comprising at least one amino acid sequence selected from SEQ. ID. NO. 2, 9, 10, 11, 13, 14, 16, 21, 22, 23, 25, 29, 32, 33, 34, 73, 74, 75, 76, 77, 78, 79, 80, 82, 83, 84, 85, 86, 87, 88, 89, 90, 91, 100, 101, 102, 112, 115, 117, 119, 121, or 117, or an amino acid sequence at least 90% identical thereto.

In an embodiment of the invention there is provided an isolated or substantially isolated amino acid sequence of no more than 100 amino acids, said sequence comprising a series of contiguous amino acids having at least 80%, 90% or 95% sequence identity to at least one of SEQ. ID. NO. 8, 12, 17, 24, 27, 28, 37, 38, 39, 40, 41, 42, 43, 44, 45, 46, 47, 48, 49, 50, 51, 52, 53, 54, 55, 56, 57, 58, 59, 60, 128, 62, 63, 64, 65, 66, 67, 103, 104, 105, 106, 107, 108, 109, 110, 111, 118, 120, 123, 124, 125, 126, 127, 128, SEQ. ID. NO. 2, 9, 10, 11, 13, 14, 16, 21, 22, 23, 25, 29, 32, 33, 34, 73, 74, 75, 76, 77, 78, 79, 80, 82, 83, 84, 85, 86, 87, 88, 89, 90, 91, 100, 101, 102, 112, 115, 117, 119, 121, 117, SEQ. 37, 38, 92, 93, 94, 95, 100, or 101. In an embodiment of the invention there is provided an isolated or substantially isolated nucleic acid sequence encoding one or more of the above amino acid sequences. In an embodiment of the invention there is provided a nucleic acid sequence substantially or completely complementary to at least one nucleic acid sequence described above. In an embodiment of the invention there is provided vectors comprising one or more of the nucleic acid sequence described above.

In an embodiment of the invention there is provided a pharmaceutical composition comprising a molecule of formula 1 with a carrier. Also provided is a method of delivering a compound of interest for preferential release at a biological site of interest, comprising obtaining a molecule of formula 1 wherein BM1 and BM2 have binding affinities for the compound of interest and the linker is selected to undergo a conformational change in under conditions present or inducible at the biological site of interest so as to reduce multivalent binding f the compound by the molecule of formula 1 at the biological site of interest.

Figure 2A:
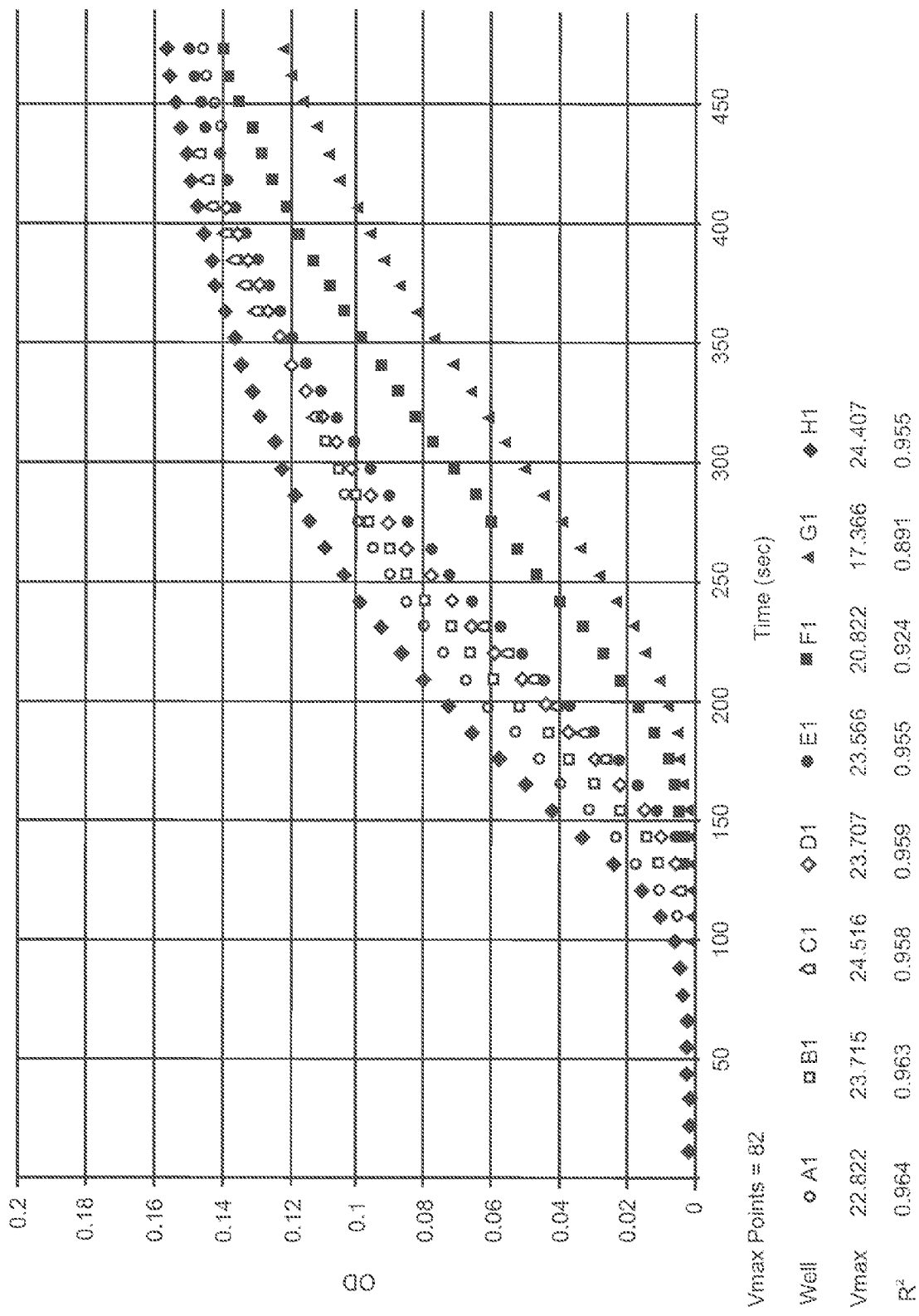
Figure 2B:
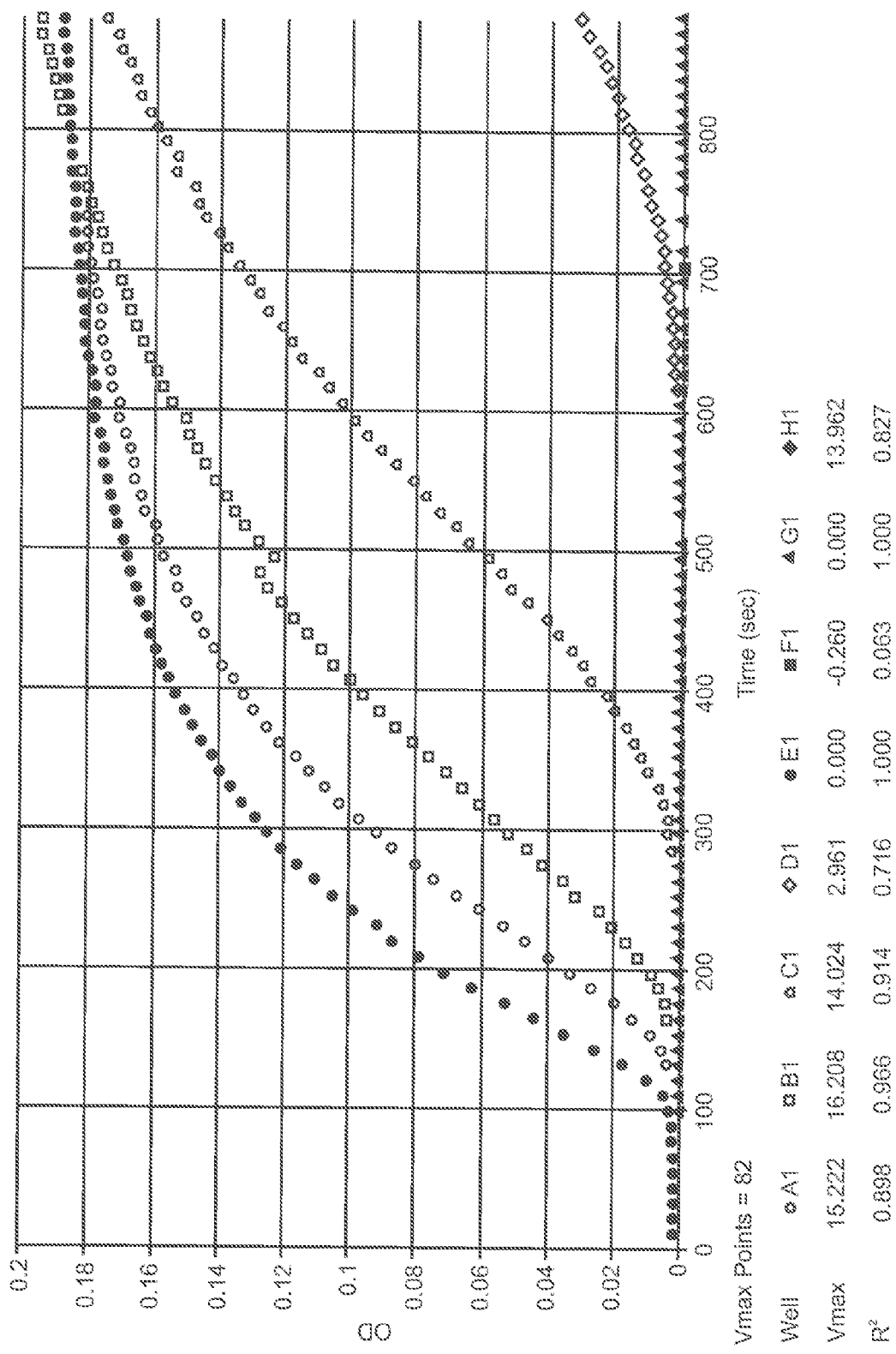
Figure 2C:
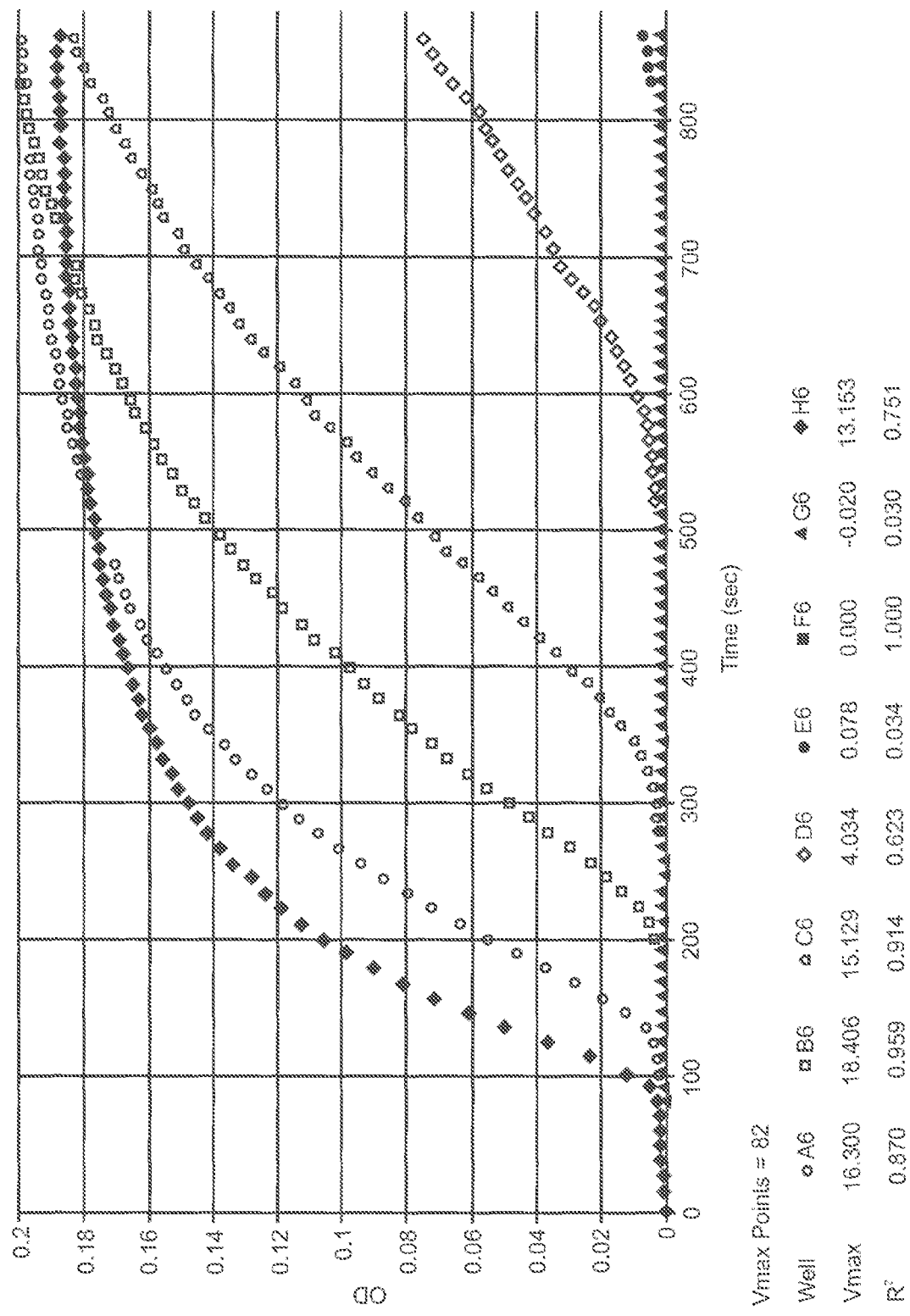
Figure 2D:
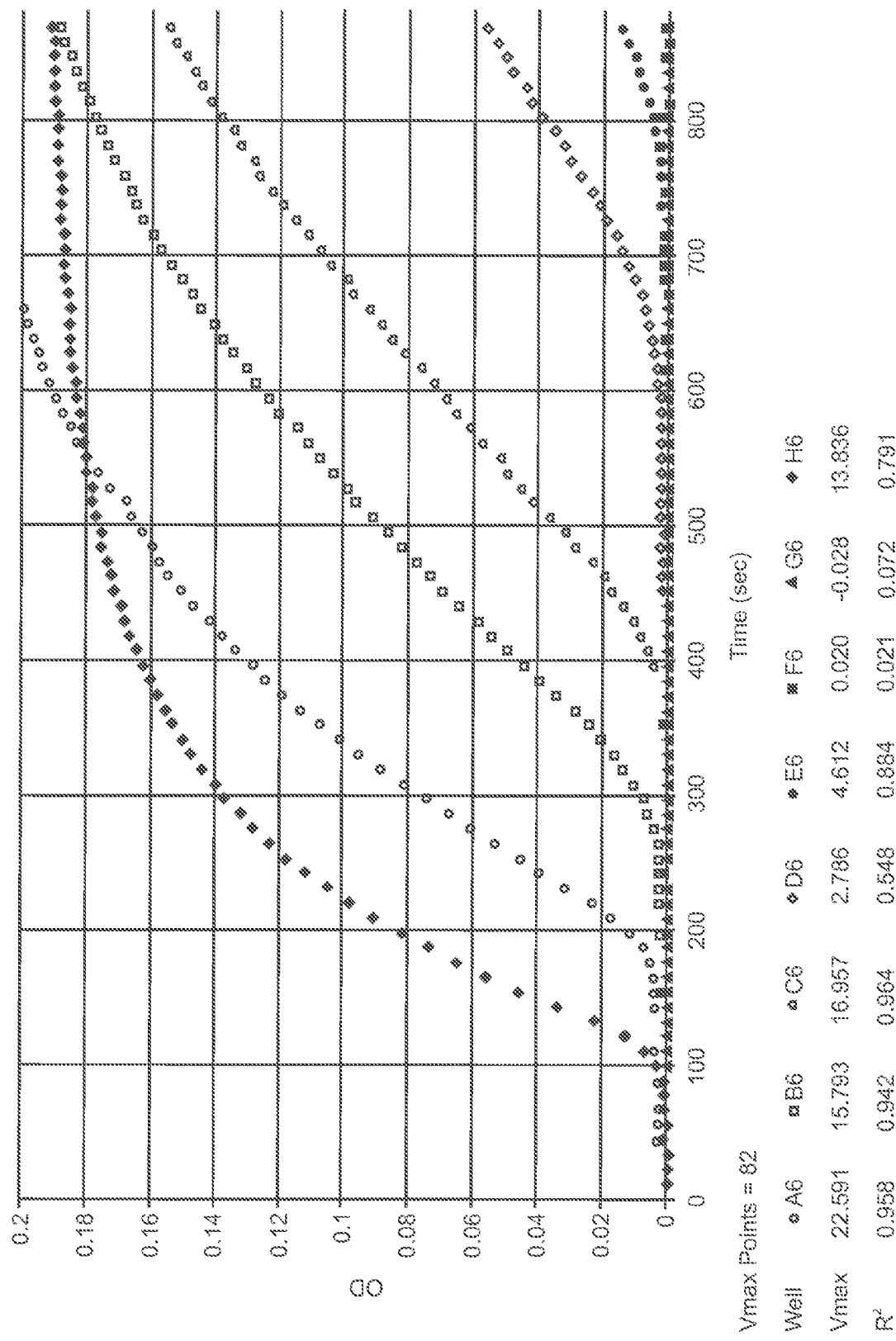

In an embodiment of the invention there is provided a method to screen a population of molecules to identify a ligand of interest. The method comprises: a) selecting a target of interest with a known affinity for a component; b) selecting a second molecule having a known affinity for the component of step (b), the second molecule binding a different region of the component from the region bound by the target; c) connecting the target and the second molecule with a suitable linker to create a bivalent structure; d) monitoring binding of the bivalent structure to the component in the presence of ligands; and, e) identifying a ligand which reduces the level of bivalent binding.

In an embodiment of the invention there is provided a method of assaying for the presence of a substance of concern in a sample. The method comprises: a) identifying a first target region known to be present on the substance of concern and less common within sample material which does not contain the substance; b) identifying a second target region known to be present on the substance of concern; c) obtaining a plurality of molecules comprising a first binding region having affinity for the first target region connected by way of a linker to a second binding region having affinity for the second target region, wherein the linker undergoes an assayable conformational change during the transition between bivalent and monovalent binding; d) combining molecules from step (c) with the sample; and e) assaying for bivalent binding.

In an embodiment of the invention there is provided a method of identifying conditions affecting a structural characteristic of a polymeric molecule of interest. The method comprises: (a) obtaining a molecule according to claim 1 wherein the linker comprises the polymeric molecule of interest and binding moieties 1 and 2 are adapted to bind a known target when the linker has a first structural condition such that bivalent binding of binding moiety 1 and binding moiety 2 to the target causes a change in an assayable characteristic of the target; (b) permitting interaction between the molecule of step (a) and the target; (c) altering the conditions under which the interaction of step (b) occurs; and (d) assaying the effect of changes of conditions on the characteristic of the target.

In an embodiment of the invention there is provided method to enhance the stability of an enzyme. The method comprises reducing functional activity of the enzyme by binding to it a molecule of formula 1 having first and second binding moieties with affinity for the enzyme. Also provided is this method with a further step of releasing bivalent binding of the molecule of formula 1 by inducing a change in the structure and/or flexibility of the linker so as to allow an increase in functional activity of the enzyme. In some instances the enzyme is a protease.

In an embodiment of the invention there is provided a method of manufacture of a device capable of activation by an electromagnetic field. The method comprises: (a) obtaining a molecule of claim 1 wherein BM1 And BM2 bind to a target and L binds to an antidote which causes a change in the linker sufficient to reduce bivalent binding of the molecule to the target; (b) conjugating the antidote with a metal nanoparticle; (c) allowing interaction between the antidote and the target such that bivalent binding occurs. Also provided is a method of activating a device manufactured according to the method above comprising releasing the ligand by heating the metal nanoparticle by means of electromagnetic radiation.

In an embodiment of the invention there is provided a method for the purification of a target. The method comprises: (a) immobilizing onto a solid support a molecule of claim 1 capable of binding to the target via BM1 and BM2; (b) allowing the target to bind the molecule of step (a); (c) eluting unbound materials; and, (d) eluting the target by inducing a condition which causes a change in structure and/or flexibility of the molecule of step (a) such that bivalent binding of the target by the molecule is reduced.

In an embodiment of the invention there is provided a method to obtain a molecule of formula 1 with high affinity to a protein target, said method comprising steps of: (a) obtaining at least two binding peptide moieties each having a binding affinity for a distinct binding site on the target based on already existing polypeptide ligands with high affinity; (b) establishing a weaker binding peptide moiety using NMR titration or NMR relaxation dispersion spectroscopy; (c) connecting the peptide moieties with a flexible linker; (d) increasing the bivalent affinity by sequence optimization of the weaker moiety by means of phage display.

In an embodiment of the invention there is provided a method to prolong the lifetime of a protease said method comprising the steps of: (a) Inhibiting the protease with a bivalent protease inhibitor containing a controllable linker; (b) Releasing and activating the protease with an appropriate linker-targeted antidote. In some instances the protease is thrombin. In some instances thrombin is a component of a fibrin sealant kit.

In an embodiment of the invention there is provided a method to detect an agent modifying the properties of the linker in a molecule of formula 1. The method comprises: (a) obtaining a multivalent ligand with the general structure of formula 1 having multivalent binding affinity for an enzyme catalyzing a detectable chemical reaction, for which the ligand is an inhibitor or an activator; (b) bringing the ligand and the enzyme in contact so as to form a complex with the ligand bound to the enzyme; and (c) carrying out an enzymatic assay of the complex wherein the course of the detectable enzymatic reaction is compared in the presence and absence of conditions modifying the properties of the linker in the bivalent ligand. In some instances the linker includes at least two residues, selected from the group of tyrosine; serine; threonine; histidine; phosphotyrosine; phosphoserine; phoshothreonine; and, phosphohistidine.

BRIEF DESCRIPTION OF THE FIGURES

FIG. 1. Depicts an embodiment of a biomolecular tweezer structure (A) in which a ligand is designed in a bivalent fashion, containing two binding moieties ("heads"), and linked by a structurally polymeric linker. (B) Depicts a proposed thermodynamic principle of linker-mediated control of bivalent ligands.

FIG. 2. Inhibition of fibrinogen clotting assays for embodiments of thrombin inhibitors of the general formula Bbs-R-(D-Pip)-linker-GDFEEIPEEYLQ (SEQ ID NO: 2).

FIG. 2*a*. Inhibition of fibrinogen clotting by the thrombin inhibitor Bbs-R-(D-Pip)-$(GS)_2$-GDFEEIPEEYLQ (SEQ ID NO: 73).

FIG. 2*b*. Inhibition of fibrinogen clotting by the thrombin inhibitor Bbs-R-(D-Pip)-$(GS)_4$-GDFEEIPEEYLQ (SEQ ID NO: 74).

FIG. 2*c*. Inhibition of fibrinogen clotting by the thrombin inhibitor Bbs-R-(D-Pip)-$(GS)_6$-GDFEEIPEEYLQ (SEQ ID NO: 75).

FIG. 2d. Inhibition of fibrinogen clotting by the thrombin inhibitor Bbs-R-(D-Pip)-(GS)$_8$-GDFEEIPEEYLQ (SEQ ID NO: 76).

Figure 2E:
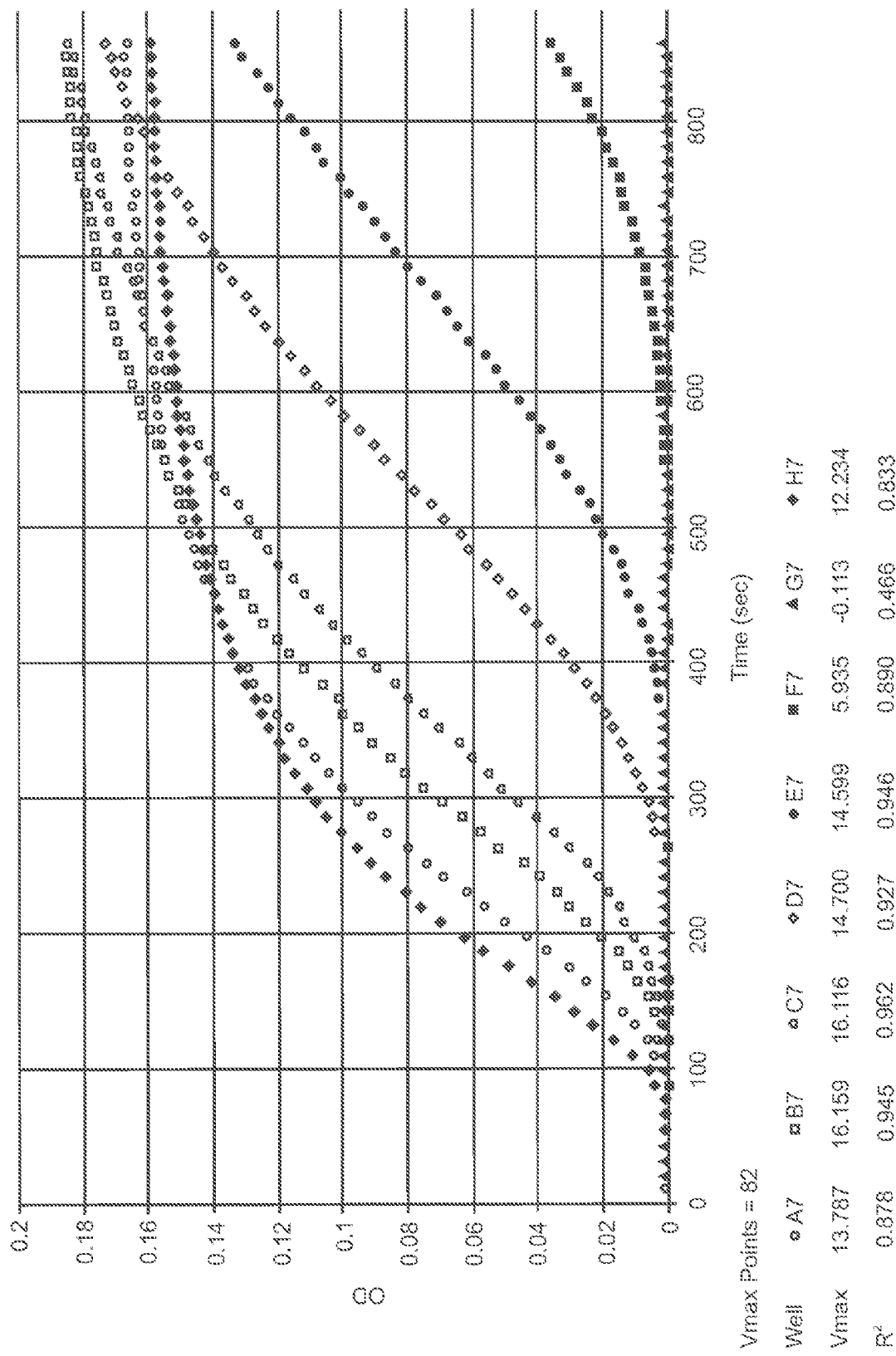

FIG. 2e. Inhibition of fibrinogen clotting by the thrombin inhibitor Bbs-R-(D-Pip)-(GS)$_{10}$-GDFEEIPEEYLQ (SEQ ID NO: 77).

Figure 2F:
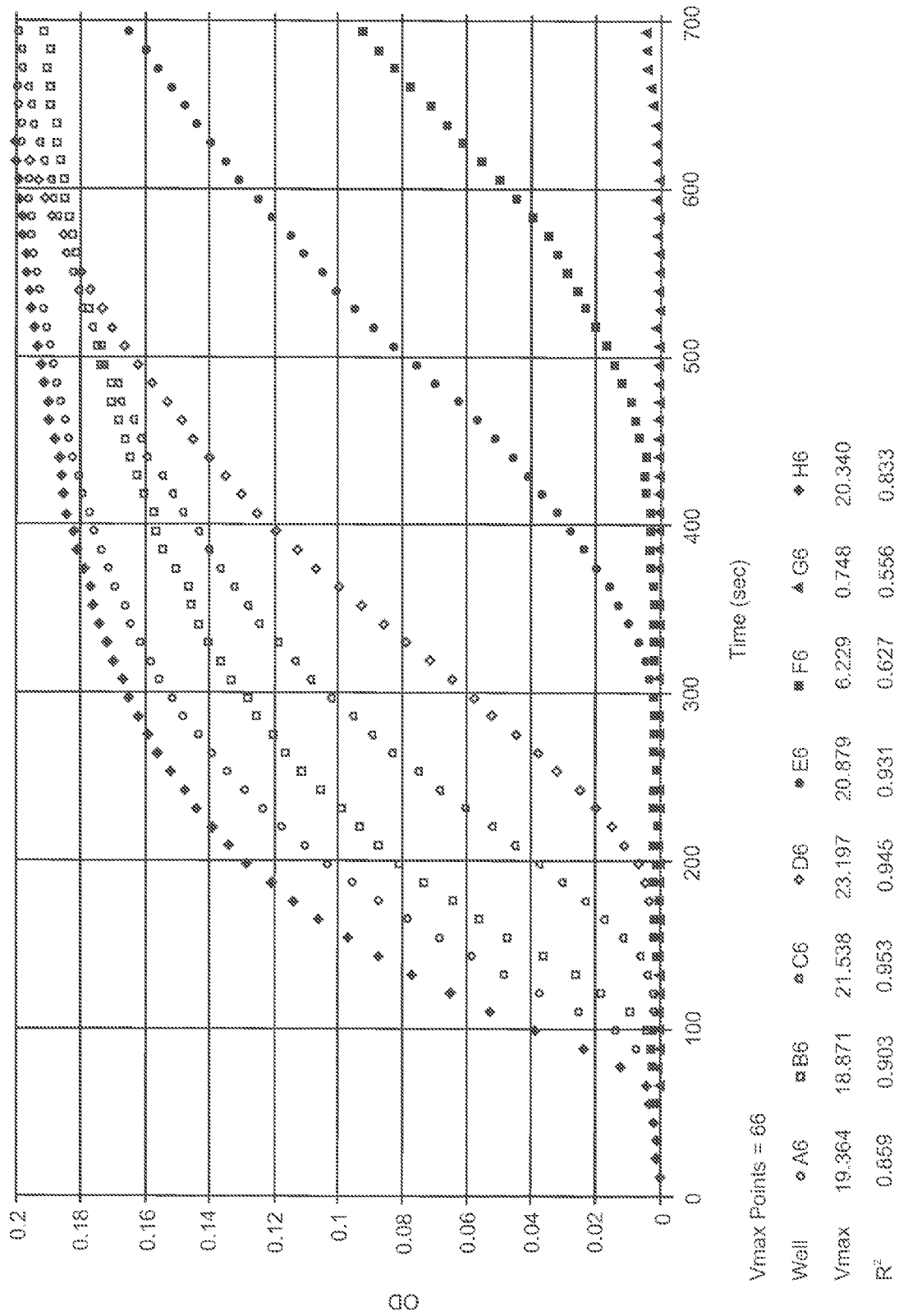

FIG. 2f. Inhibition of fibrinogen clotting by the thrombin inhibitor Bbs-R-(D-Pip)-(GS)$_{12}$-GDFEEIPEEYLQ (SEQ ID NO: 78).

Figure 2G:
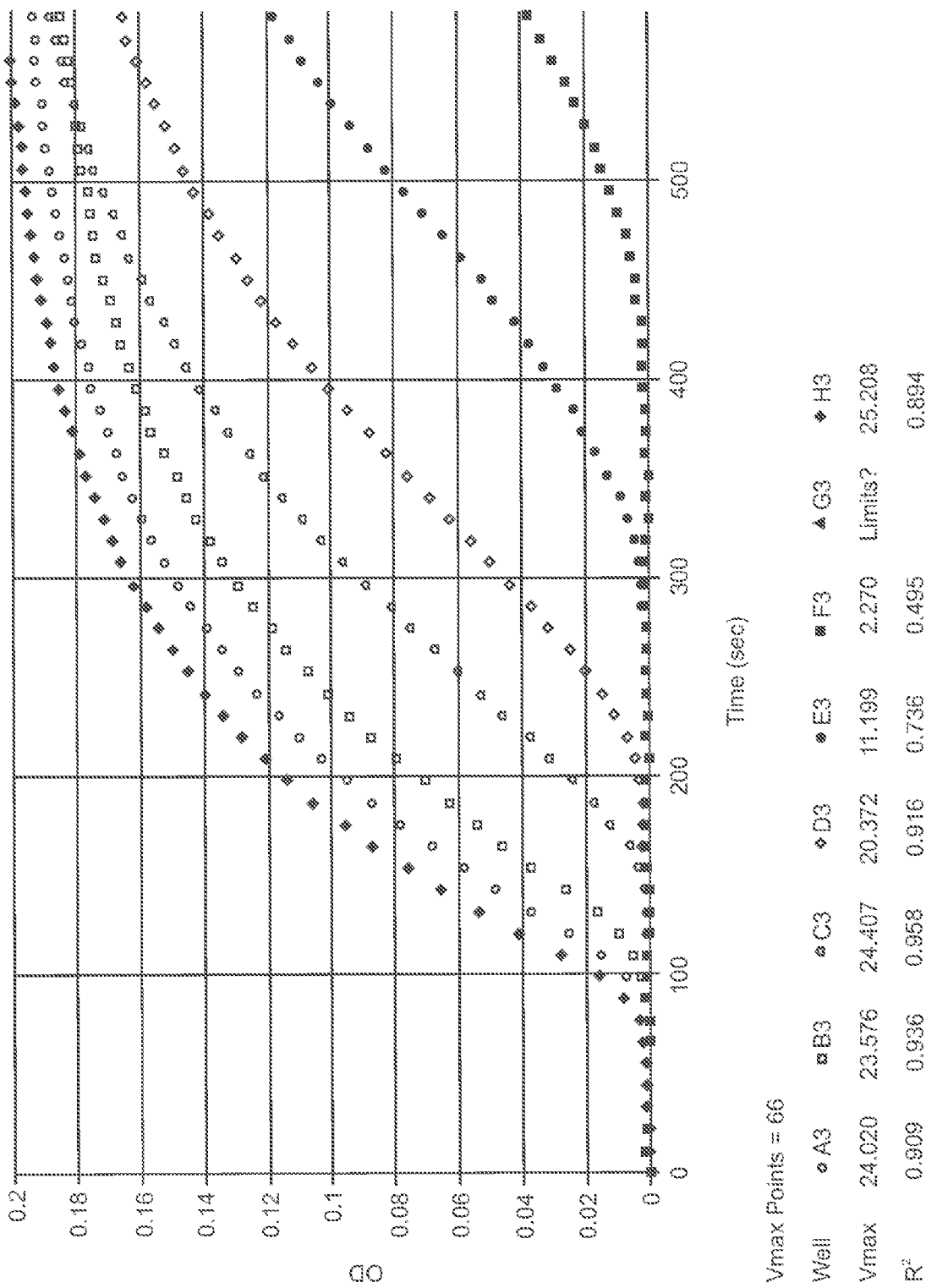

FIG. 2g. Inhibition of fibrinogen clotting by the thrombin inhibitor Bbs-R-(D-Pip)-(GS)$_{14}$-GDFEEIPEEYLQ (SEQ ID NO: 79).

Figure 2H:
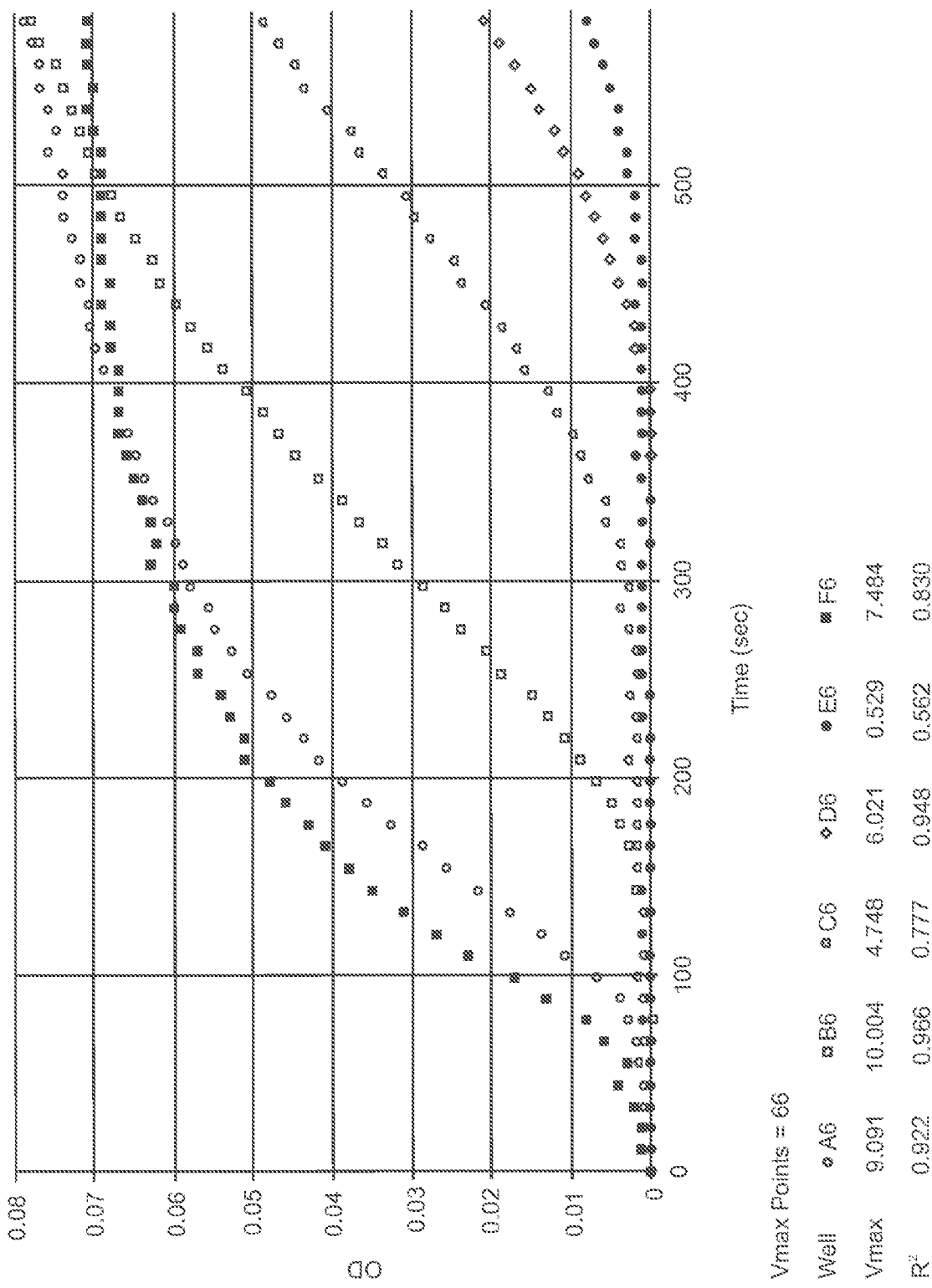

FIG. 2h. Inhibition of fibrinogen clotting by the thrombin inhibitor Bbs-R-(D-Pip)-Gly-Cys . . . Cys-(Gly-Ser)$_8$-Gly-DFEEIPEEYLQ (SEQ ID NO: 83).

Figure 2I:
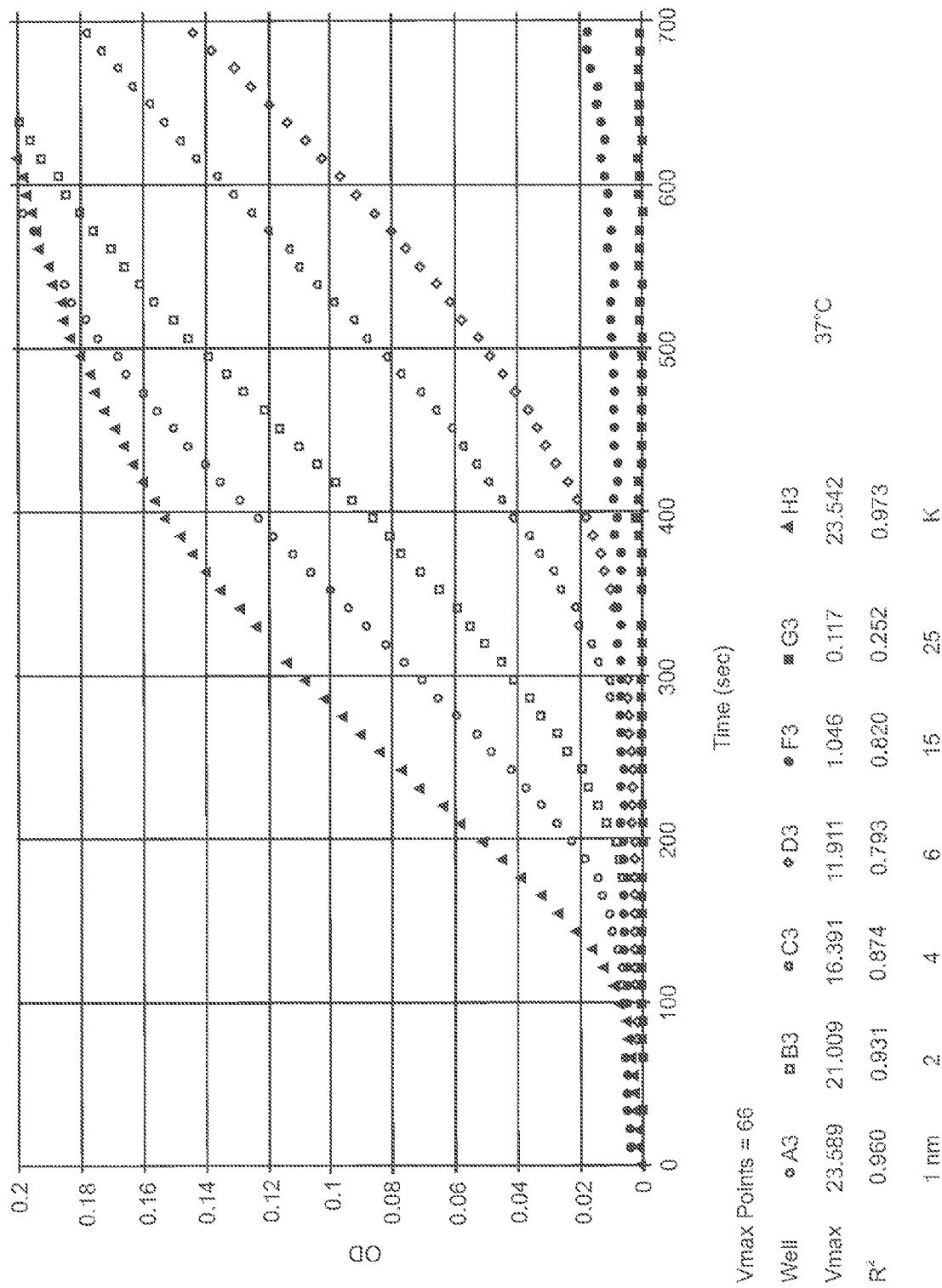

FIG. 2i. Inhibition of fibrinogen clotting by the thrombin inhibitor Bbs-R-(D-Pip)-GTLDLNTPVDKTSN-GDFEE-IPEEYLQ (SEQ ID NO: 85).

Figure 2J:
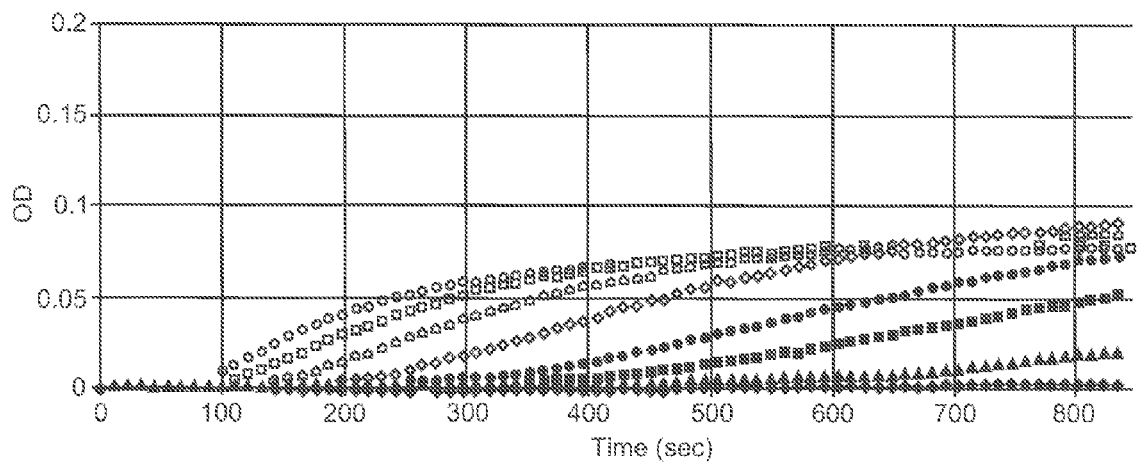

FIG. 2j. Inhibition of fibrinogen clotting by the thrombin inhibitor Bbs-R-(D-Pip)-GSGSGSGSGKGSGSGSGSGS-GDFEEIPEEYLQ (SEQ ID NO: 84).

Figure 2K:
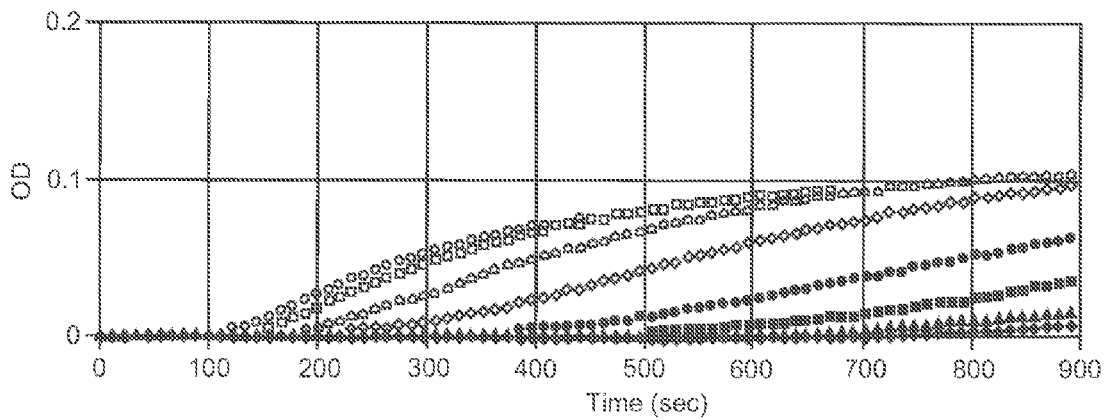

FIG. 2k. Inhibition of fibrinogen clotting by the thrombin inhibitor Bbs-R-(D-Pip)-GSWPRPQLHND-GDFEE-IPEEYLQ (SEQ ID NO: 32).

Figure 2L:
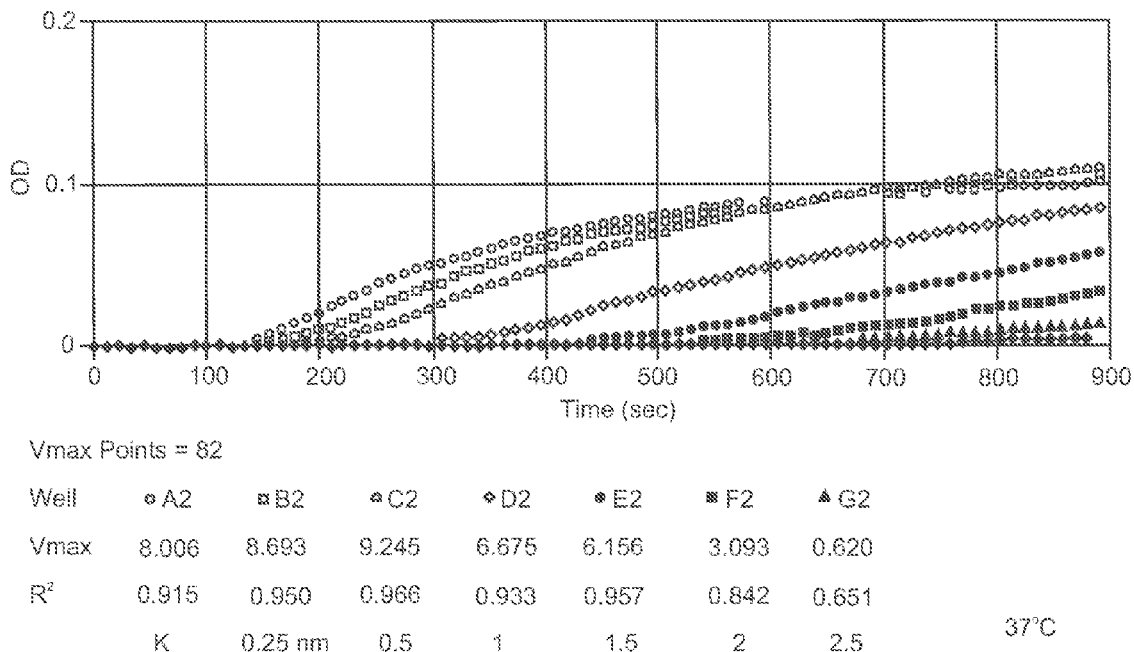

FIG. 2l. Inhibition of fibrinogen clotting by the thrombin inhibitor Bbs-R-(D-Pip)-GSHAPRPQIHND-GDFEE-IPEEYLQ (SEQ ID NO: 33).

Figure 2M:
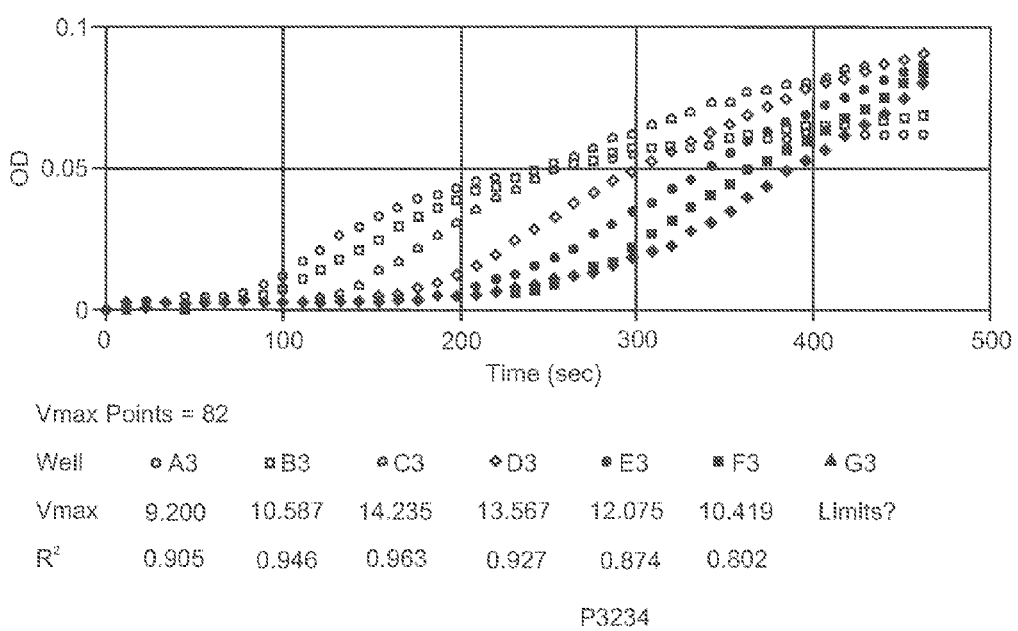

FIG. 2m. Inhibition of fibrinogen clotting by the thrombin inhibitor Bbs-R-(D-Pip)-GHHLGGAKQAGDV-GDFEE-IPEEYLQ (SEQ ID NO: 88).

Figure 2N:
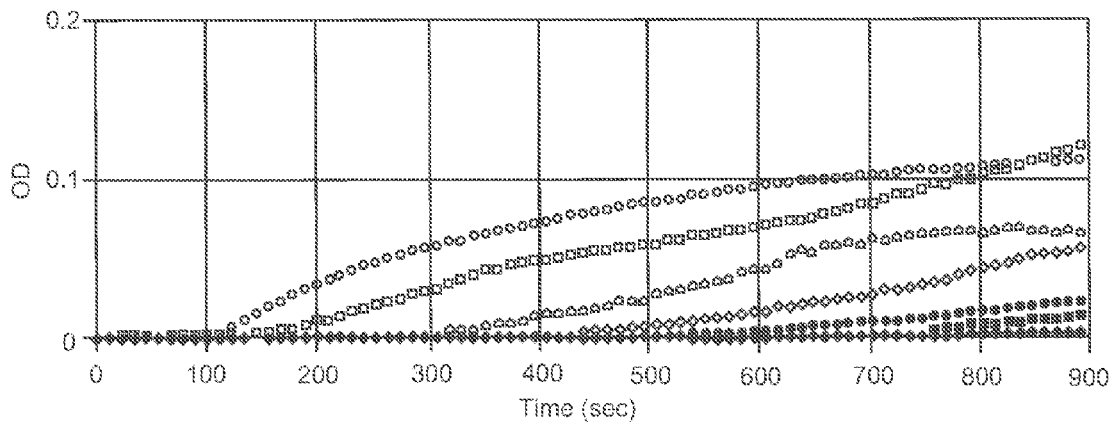

FIG. 2n. Inhibition of fibrinogen clotting by the thrombin inhibitor Bbs-R-(D-Pip)-GYMESRADR-GDFEEIPEEYLQ (SEQ ID NO: 89).

Figure 2O:
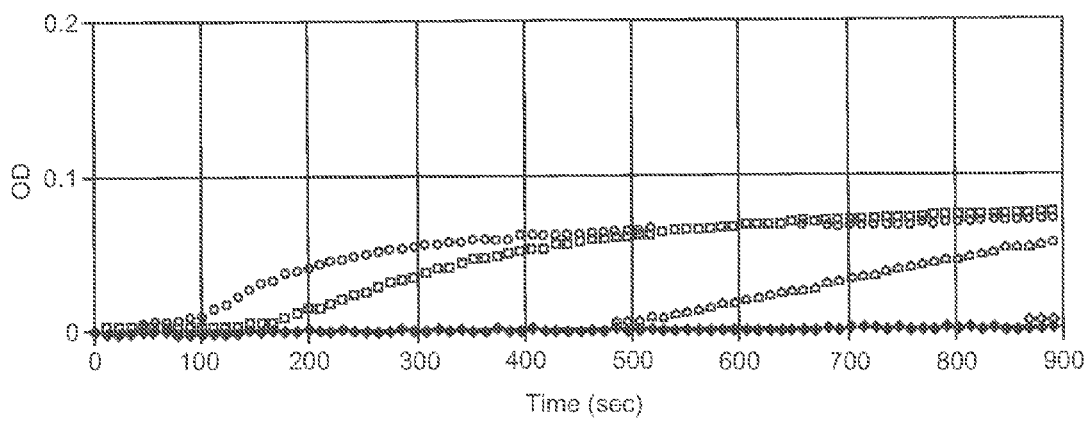

FIG. 2o. Inhibition of fibrinogen clotting by the thrombin inhibitor Bbs-R-(D-Pip)-GQSHNR-GDFEEIPEEYLQ (SEQ ID NO: 90).

FIG. 3. Inhibition of fibrinogen clotting assays for embodiments of thrombin inhibitors of the general formula Bbs-R-(D-Pip)-G-(SPH(B)EKVSG)$_n$-DFEEIPEEYLQ (SEQ ID NO: 9).

Figure 3A:
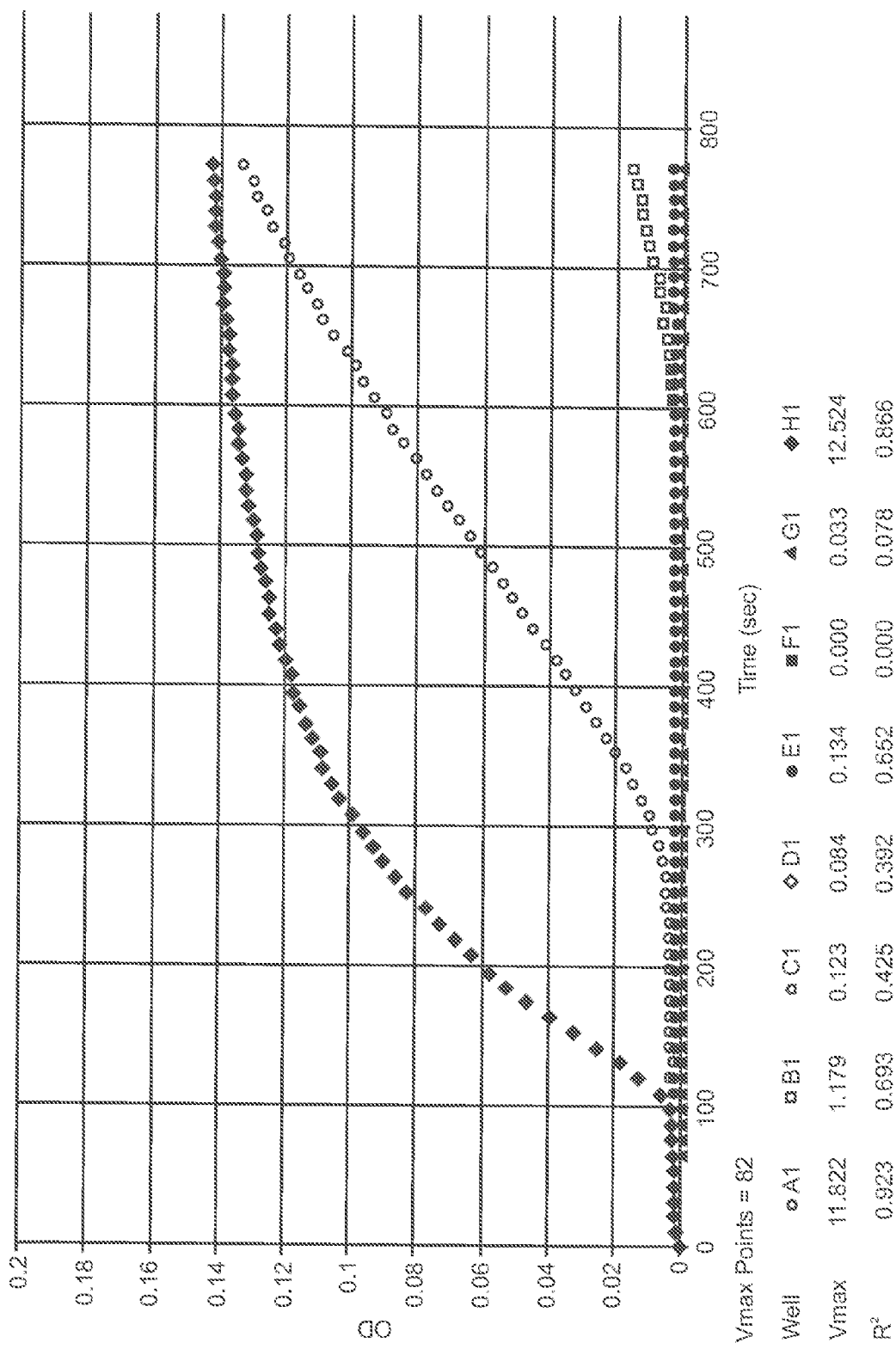

FIG. 3a. Inhibition of fibrinogen clotting by the thrombin inhibitor Bbs-Arg-(D-Pip)-Gly-(Ser-Pro-His-Tyr-Glu-Lys-Val-Ser-Gly)-Asp-Phe-Glu-Glu-Ile-Pro-Glu-Glu-Tyr-Leu-Gln (SEQ ID NO: 80).

Figure 3B:
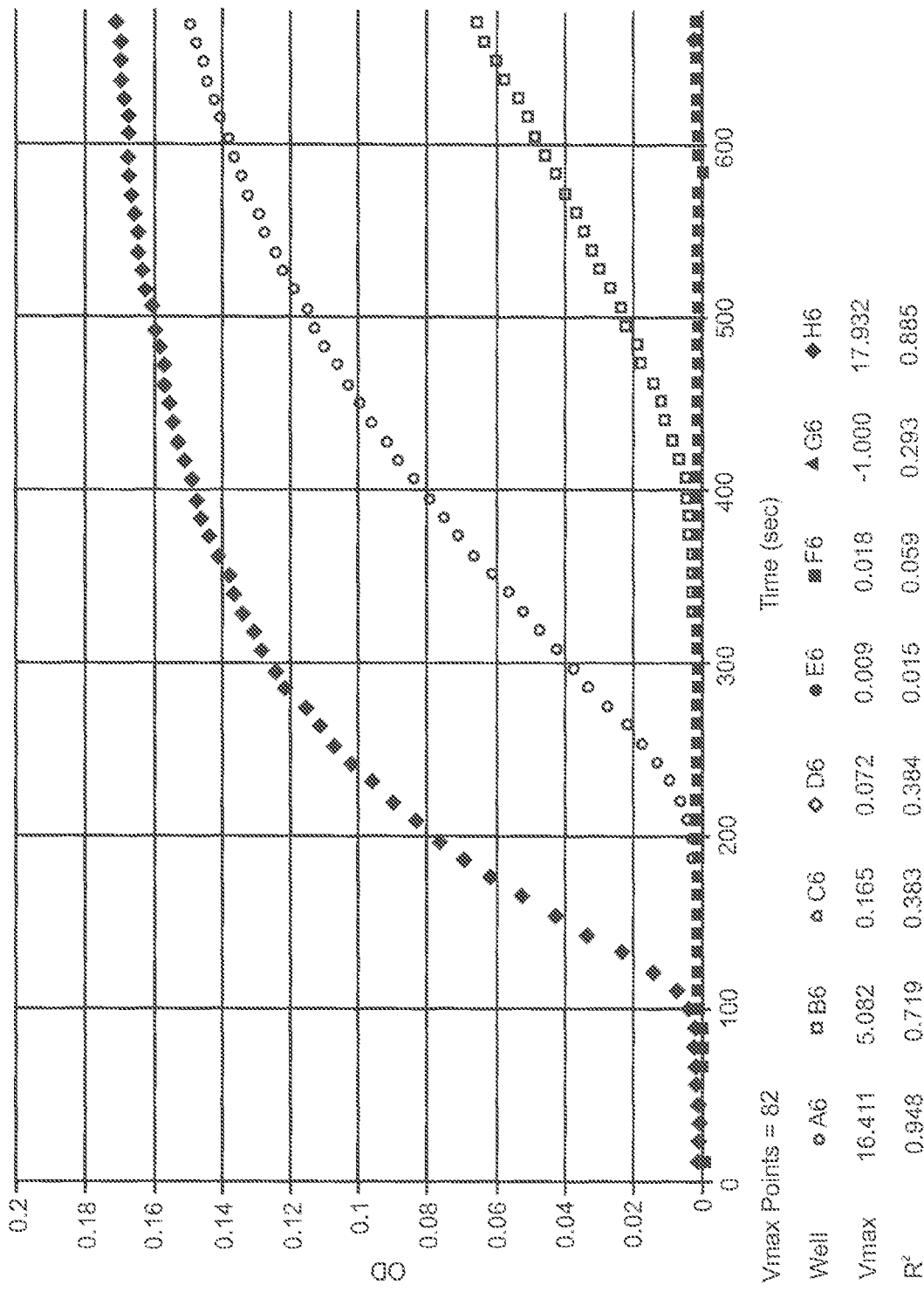

FIG. 3b. Inhibition of fibrinogen clotting by the thrombin inhibitor Bbs-Arg-(D-Pip)-Gly-(Ser-Pro-His-Tyr(P)-Glu-Lys-Val-Ser-Gly)-Asp-Phe-Glu-Glu-Ile-Pro-Glu-Glu-Tyr-Leu-Gln (SEQ ID NO: 82).

Figure 3C:
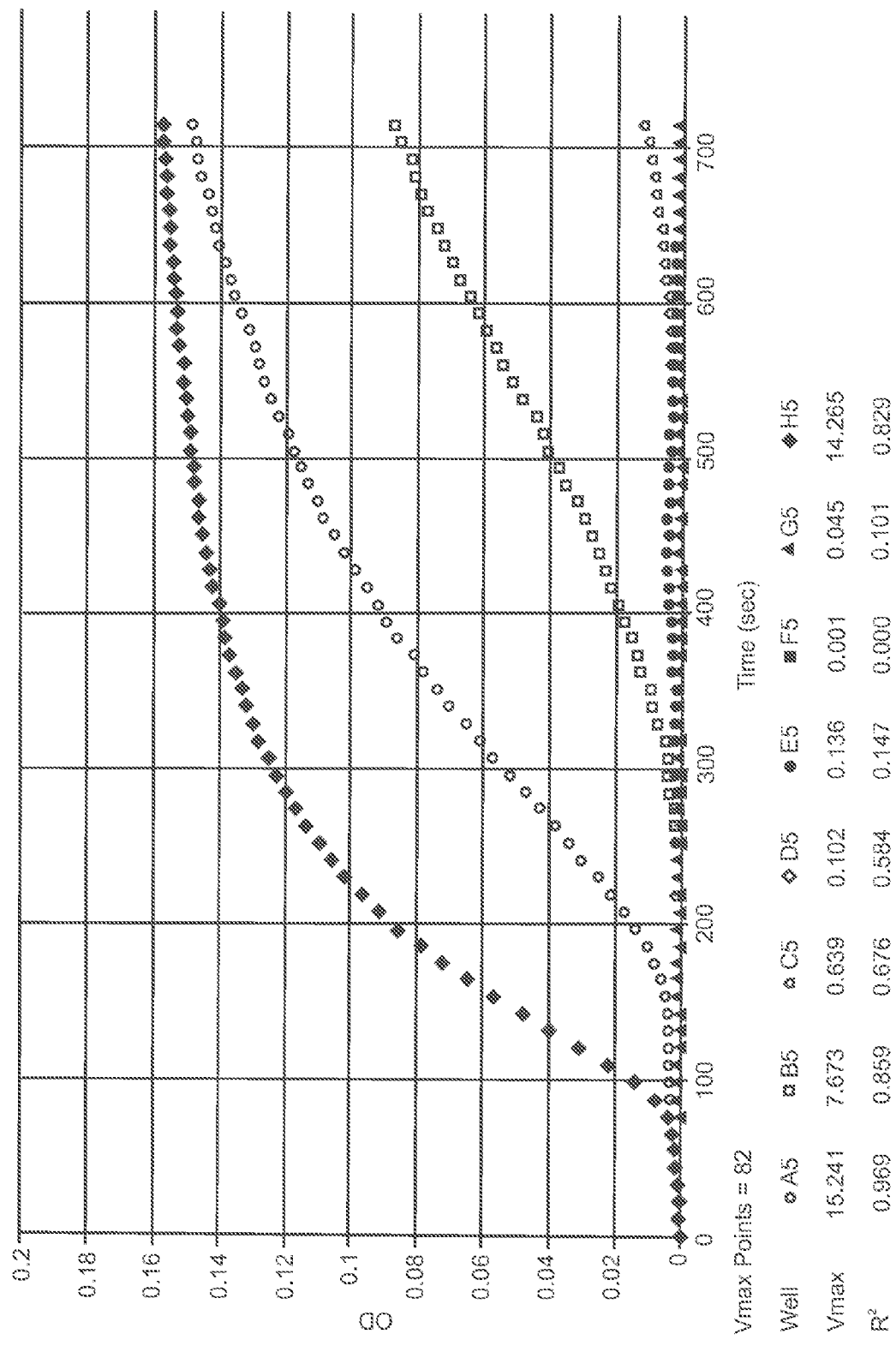

FIG. 3c. Inhibition of fibrinogen clotting by the thrombin inhibitor Bbs-Arg-(D-Pip)-Gly-(Ser-Pro-His-Tyr-Glu-Lys-Val-Ser-Gly)$_2$-Asp-Phe-Glu-Glu-Ile-Pro-Glu-Glu-Tyr-Leu-Gln (SEQ ID NO: 81).

Figure 3D:
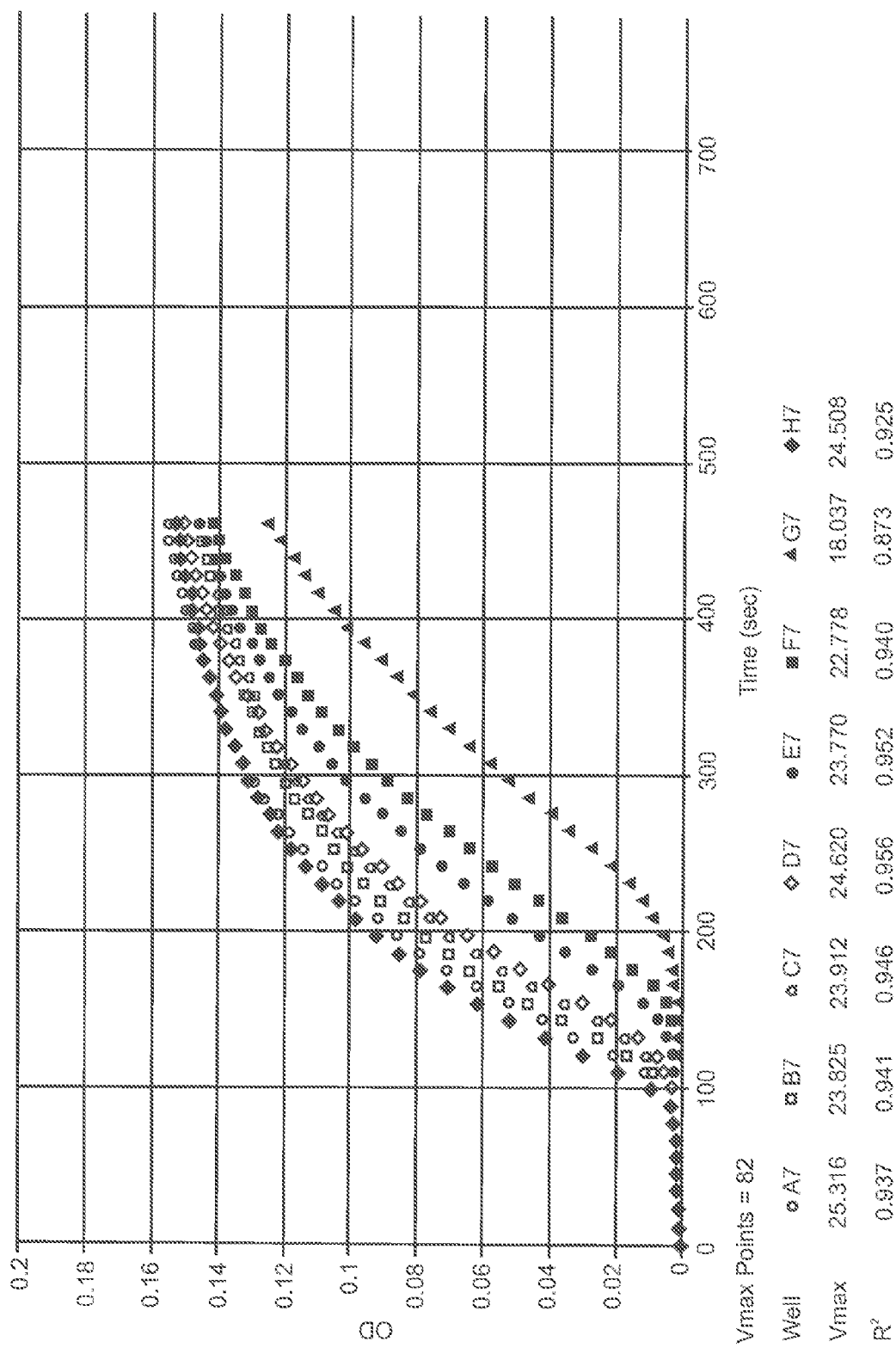

FIG. 3d. Inhibition of fibrinogen clotting by the thrombin inhibitor Bbs-Arg-(D-Pip)-Gly-(Ser-Pro-His-Tyr(P)-Glu-Lys-Val-Ser-Gly)$_2$-Asp-Phe-Glu-Glu-Ile-Pro-Glu-Glu-Tyr-Leu-Gln (SEQ ID NO: 82).

FIG. 4. Inhibition of fibrinogen clotting assays for thrombin inhibitors of the general formula Bbs-R-(D-Pip)-G-(SPH(B)EKVSG)$_n$-DFEEIPEEYLQ (SEQ ID NO: 9) in the presence and absence of an SH2 domain from the Grb4 adaptor protein.

Figure 4A:
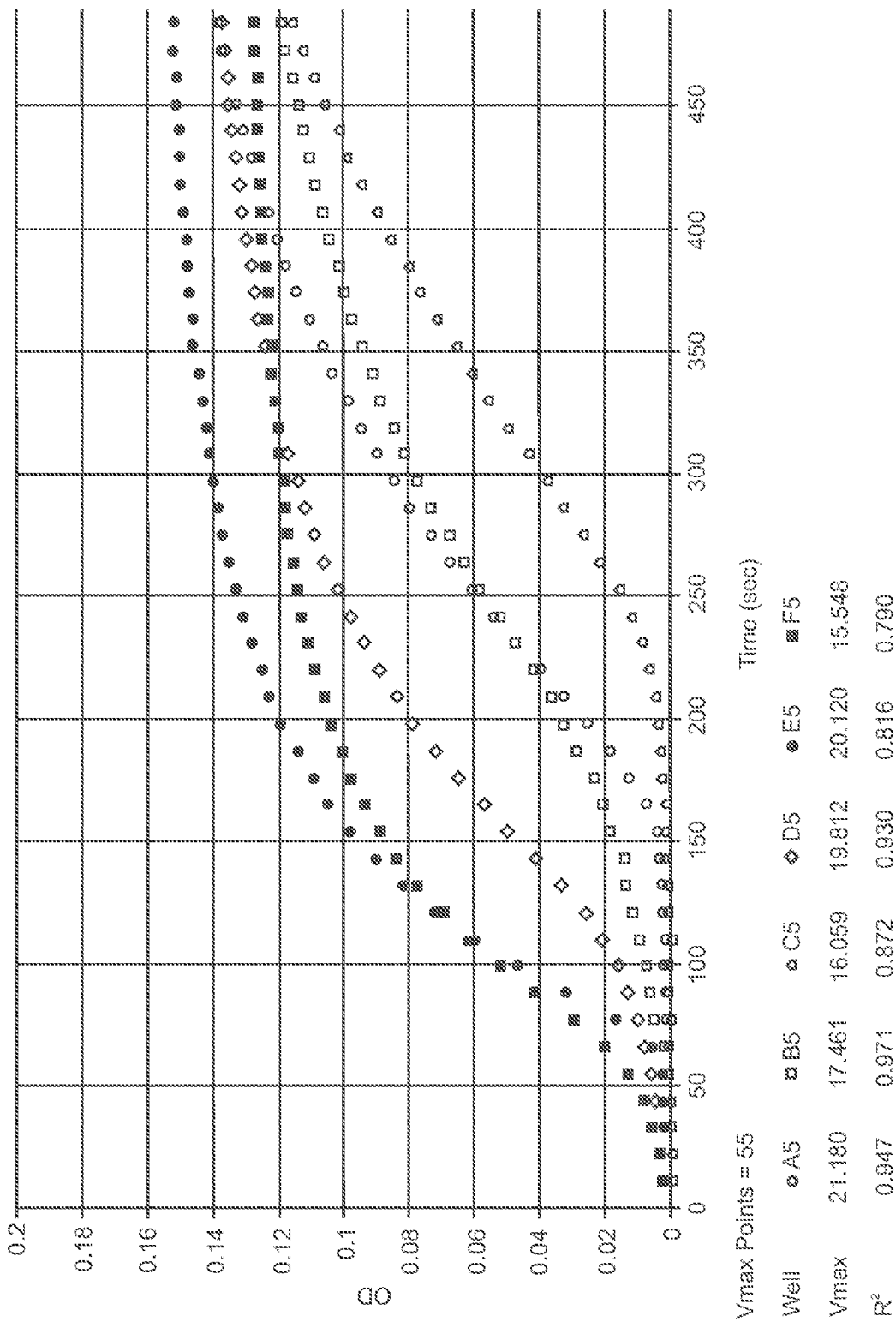

FIG. 4a. Inhibition of fibrinogen clotting by the thrombin inhibitors Bbs-R-(D-Pip)-G-(SPH-B-EKVSG)$_2$-DFEE-IPEEYLQ (SEQ ID NO: 115) in the presence and absence of an SH2 domain from the Grb4 adaptor protein.

Figure 4B:
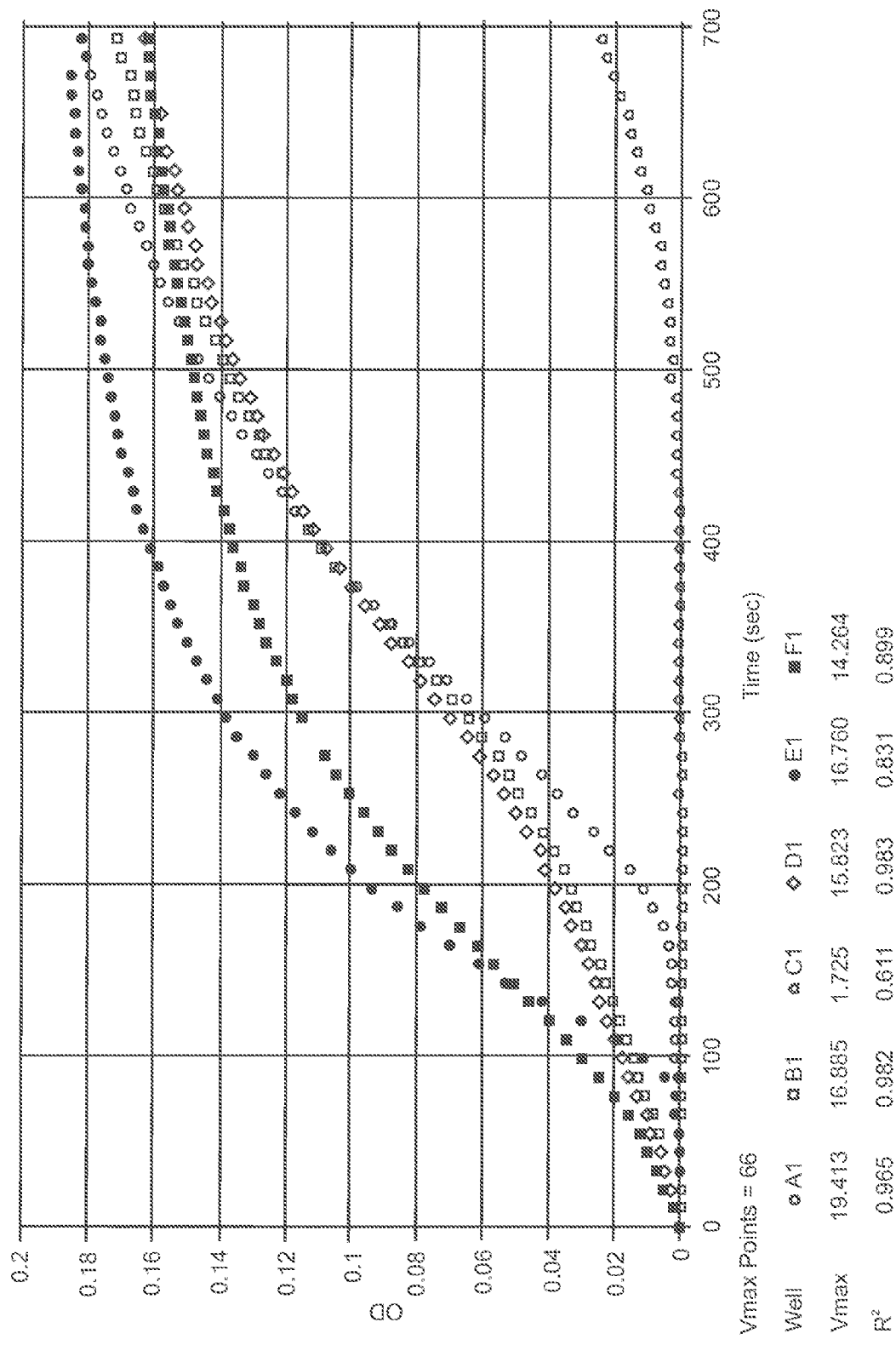

FIG. 4b. Inhibition of fibrinogen clotting by the thrombin inhibitors Bbs-R-(D-Pip)-G-(SPH-B-EKVSG)-DFEE-IPEEYLQ (SEQ ID NO: 9 where n=1) in the presence and absence of an SH2 domain from the Grb4 adaptor protein.

Figure 5:
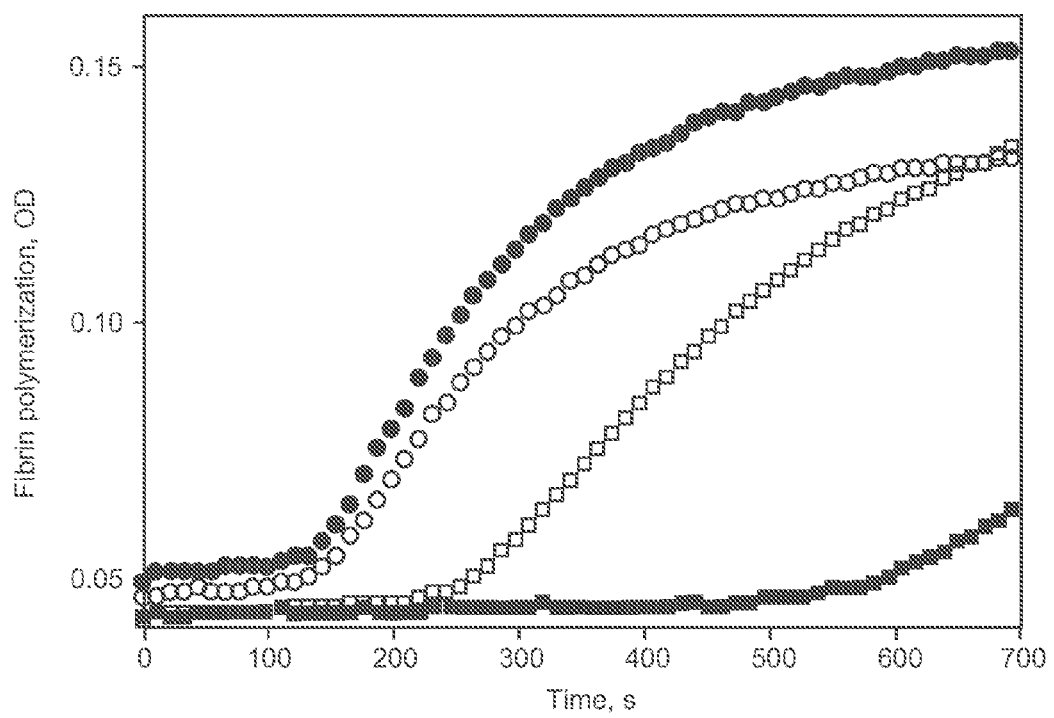

FIG. 5. Inhibition of fibrinogen clotting assays for thrombin inhibitor of the formula Bbs-R-(D-Pip)-GEQKLI-SEEDLG-DFEEIPEEYLQ (SEQ ID NO: 13) in the presence and absence of the anti-c-myc antibody 9E10 (Sigma).

FIG. 6. Effect of calcium on the NMR spectra of calcium-binding linkers.

Figure 6A:
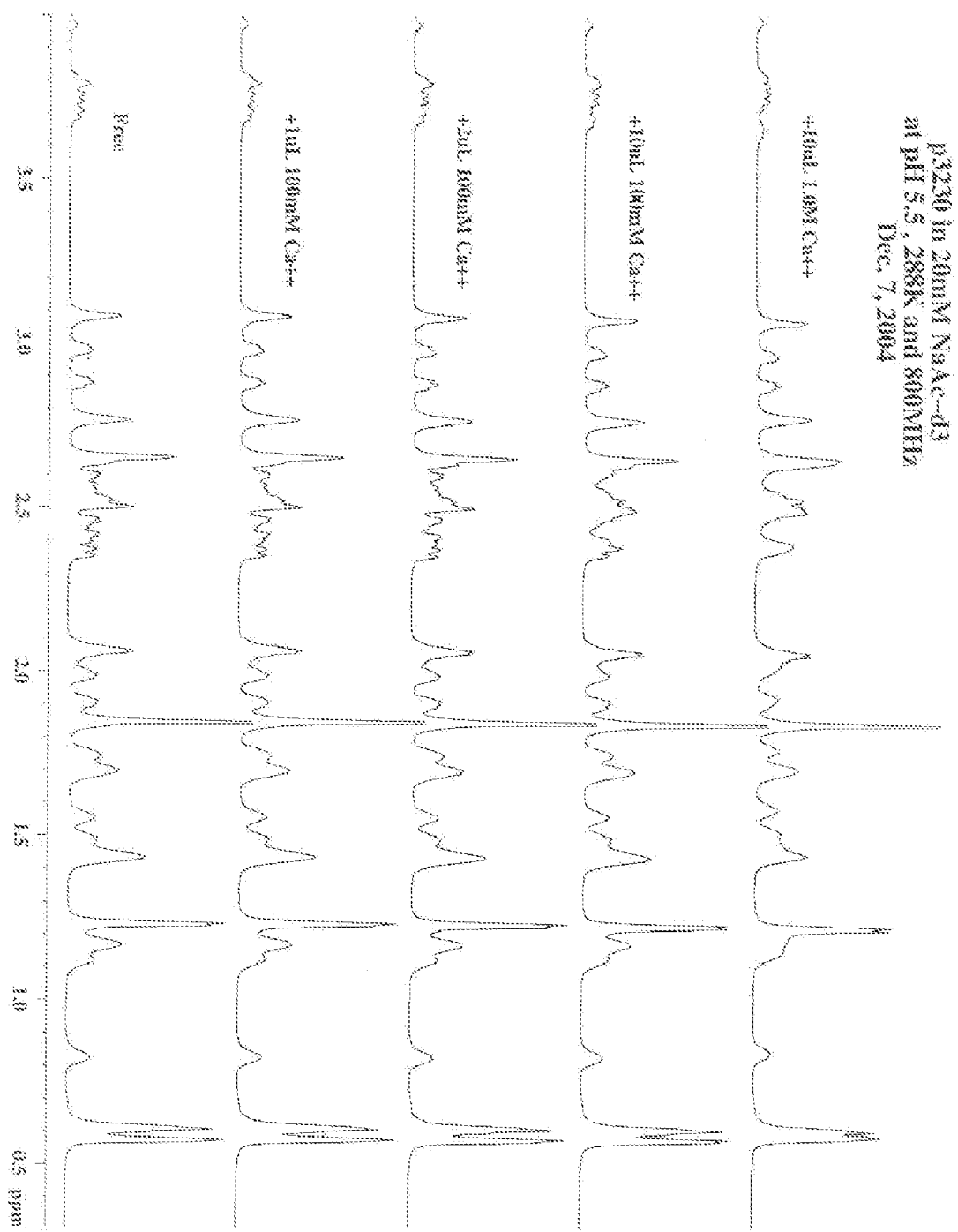

FIG. 6a. Changes in the proton NMR spectra of Ac-Asp-Lys-Asn-Ala-Asp-Gly-Trp-Ile-Asp-Asn-Gly-Glu-Phe-Glu-NH$_2$ (SEQ ID NO: 109) upon the addition of CaCl$_2$.

Figure 6B:
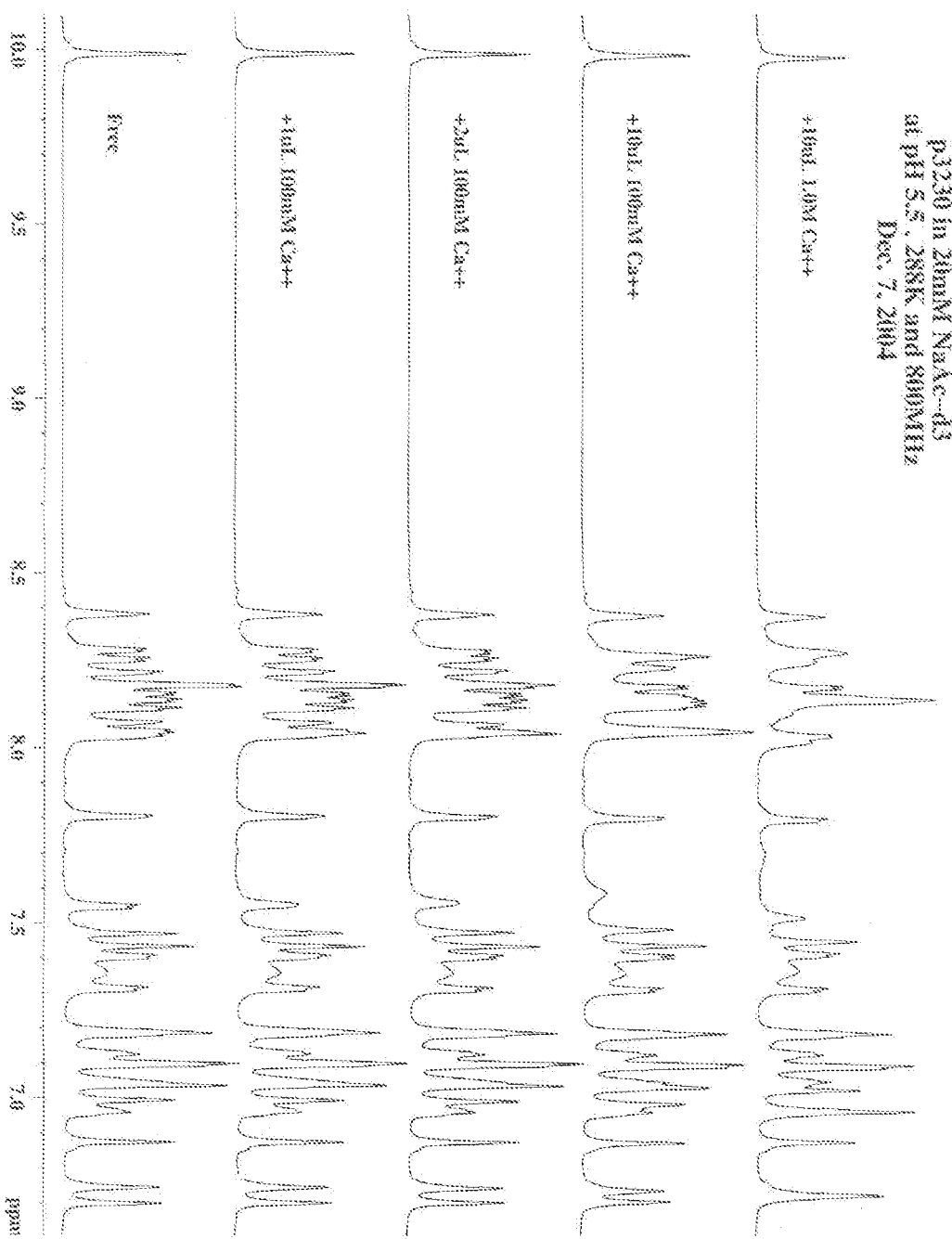

FIG. 6b. Changes in the proton NMR spectra of Ac-Asp-Lys-Asn-Ala-Asp-Gly-Trp-Ile-Asp-Asn-Gly-Glu-Phe-Glu-NH$_2$ (SEQ ID NO: 109) upon the addition of CaCl$_2$.

Figure 6C:
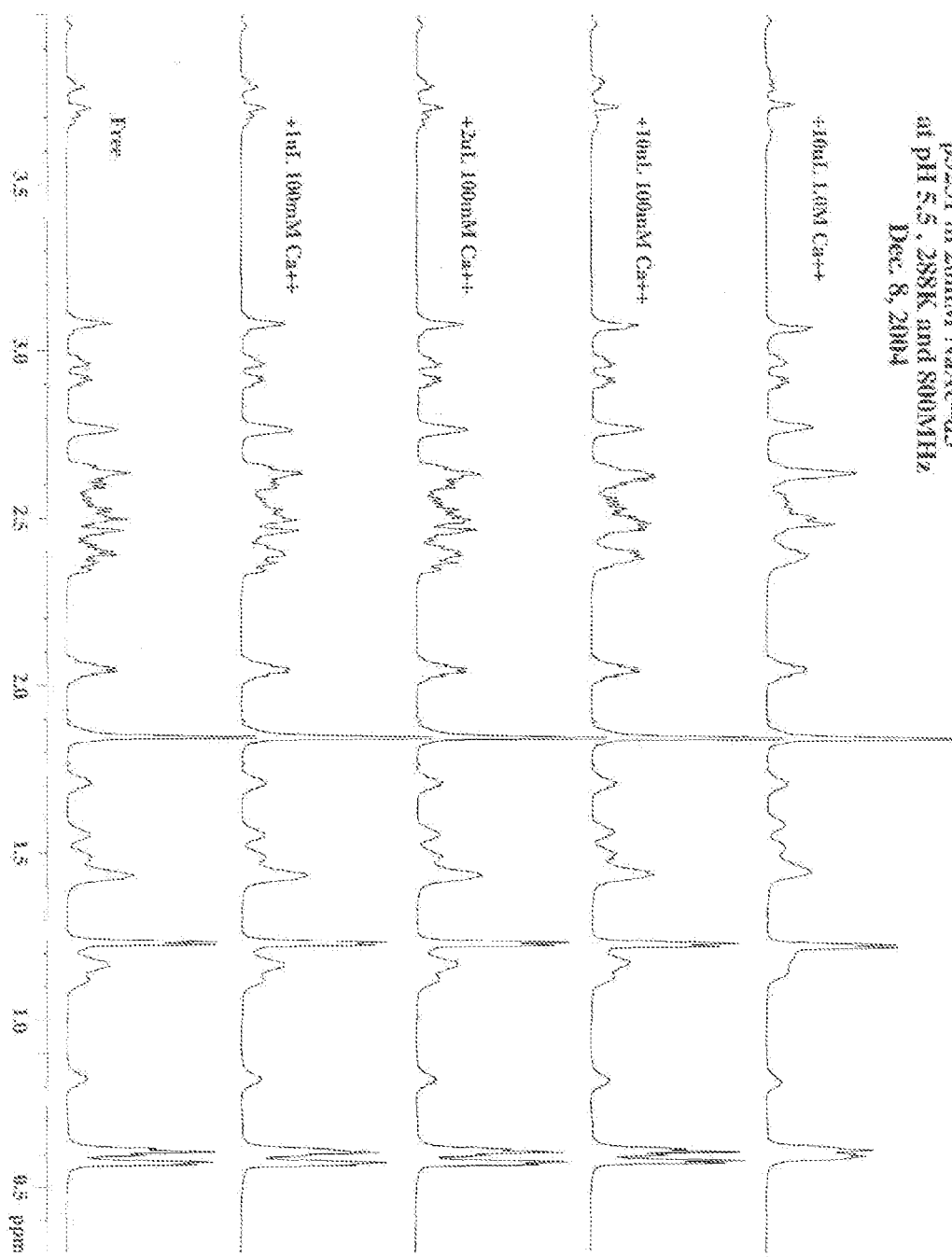

FIG. 6c. Changes in the proton NMR spectra of Ac-Asp-Lys-Asn-Ala-Asp-Gly-Trp-Ile-Asp-Asn-Gly-Asp-Phe-Glu-NH$_2$ (SEQ ID NO: 109) upon the addition of CaCl$_2$.

Figure 6D:
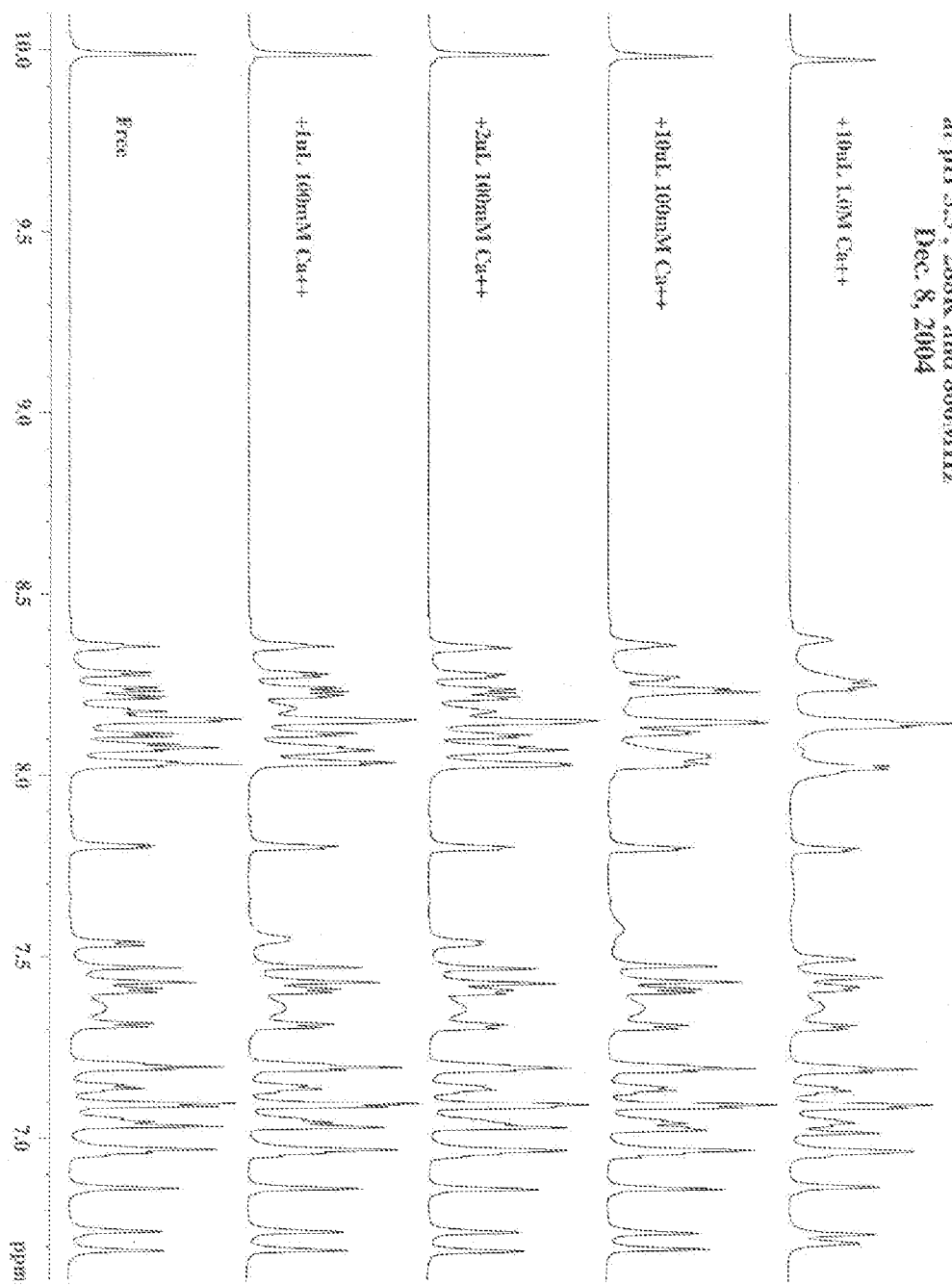

FIG. 6d. Changes in the proton NMR spectra of Ac-Asp-Lys-Asn-Ala-Asp-Gly-Trp-Ile-Asp-Asn-Gly-Asp-Phe-Glu-NH$_2$ (SEQ ID NO: 109) upon the addition of CaCl$_2$.

Figure 6E:
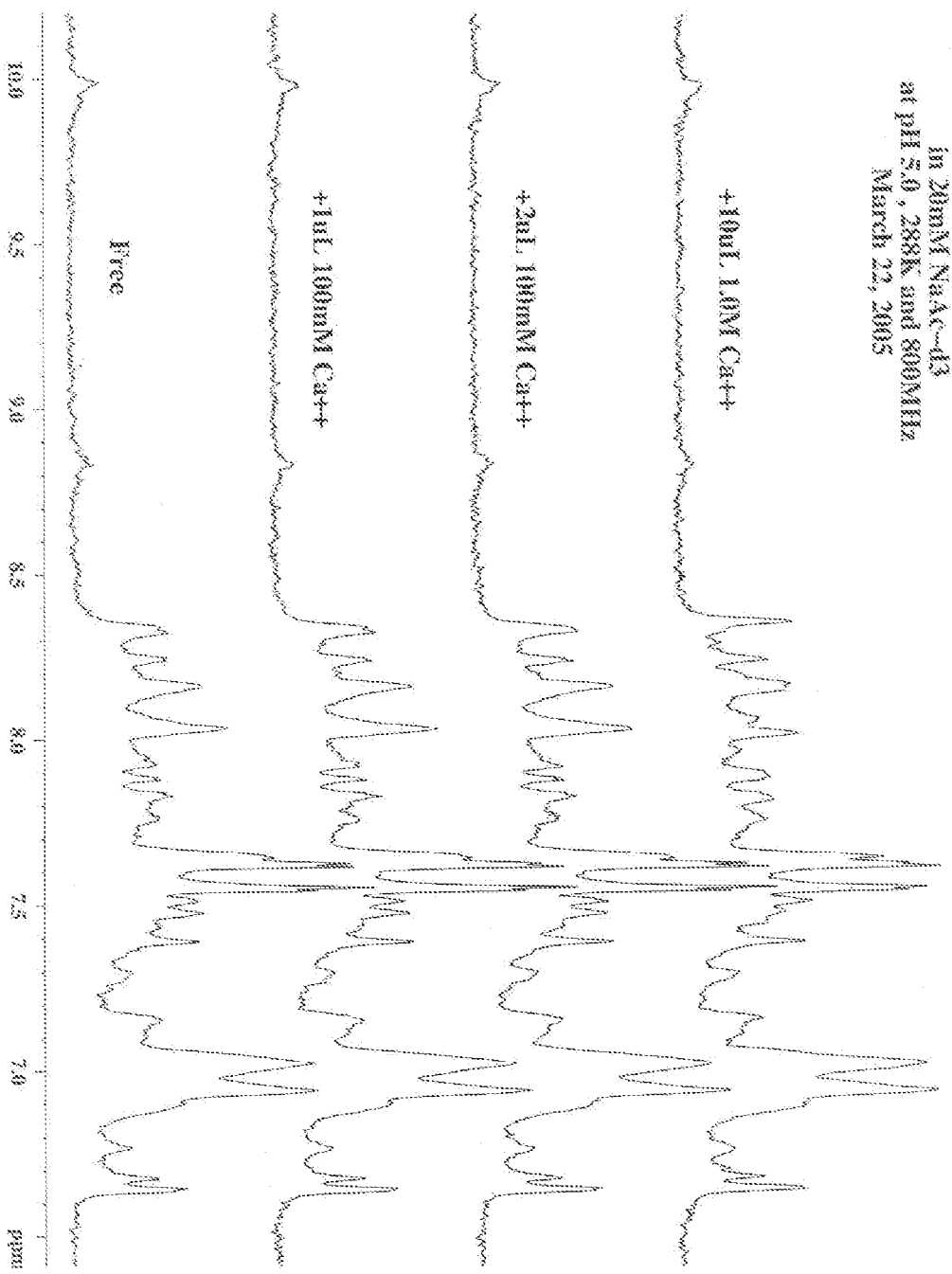

FIG. 6e. Changes in the proton NMR spectra of Bbs-Arg-(D-Pip)-Gly-Cys . . . Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ ID NO: 16) upon the addition of CaCl$_2$.

Figure 6F:
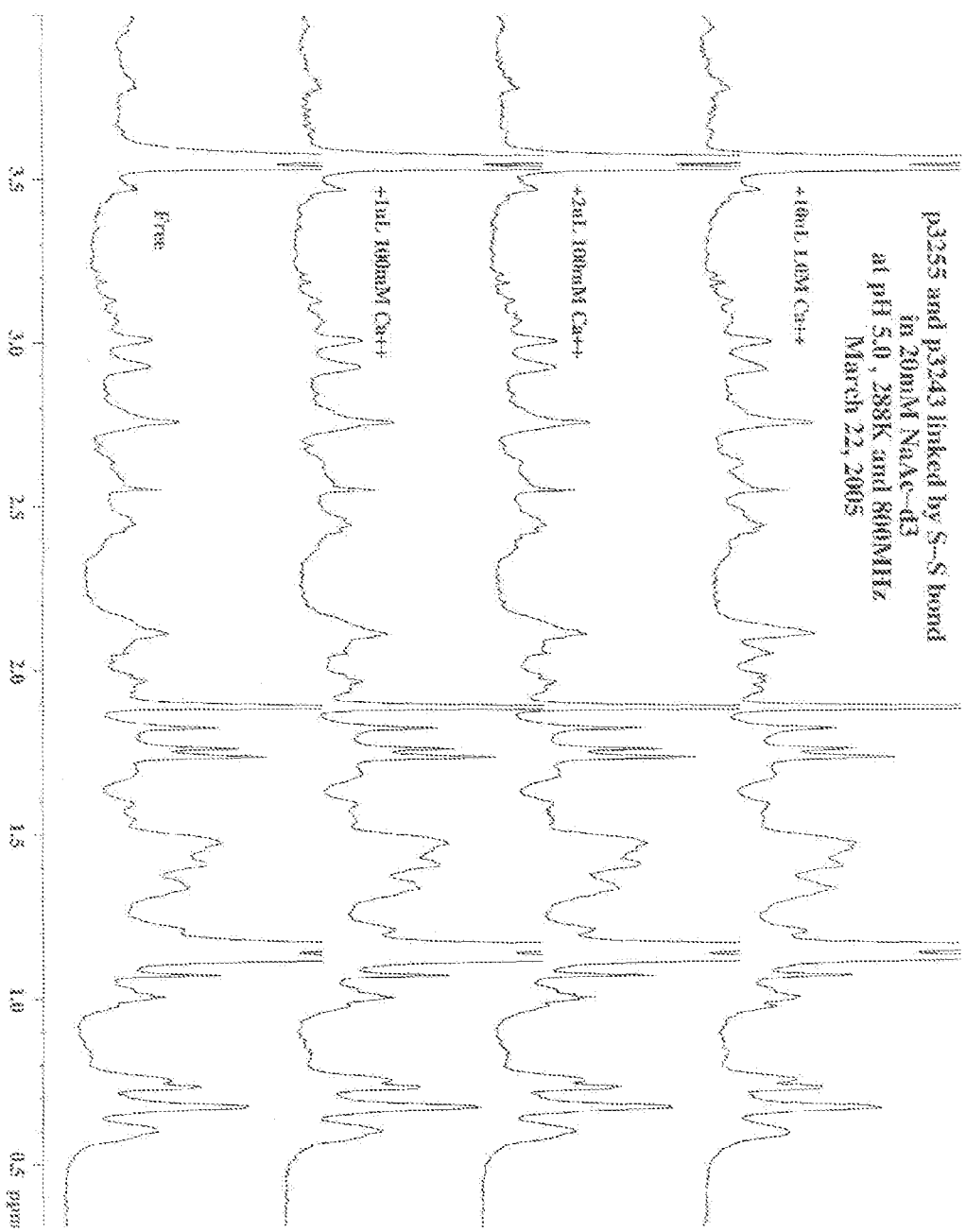

FIG. 6f. Changes in the proton NMR spectra of Bbs-Arg-(D-Pip)-Gly-Cys . . . Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ ID NO: 16) upon the addition of CaCl$_2$.

Figure 7:
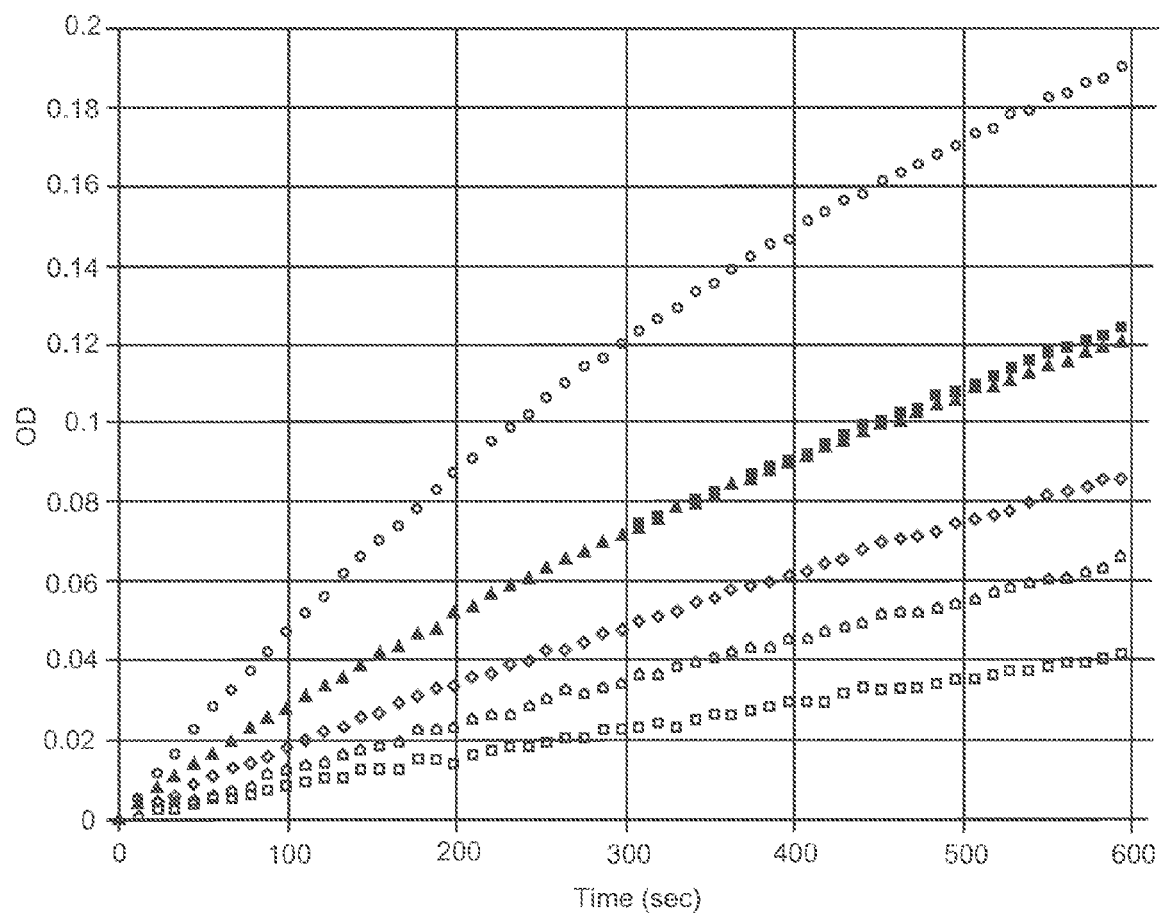

FIG. 7. Effect of calcium on the inhibition of the amidolydic activity of thrombin by Bbs-Arg-(D-Pip)-Gly-Cys . . . Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ ID NO: 16).

Figure 8A:
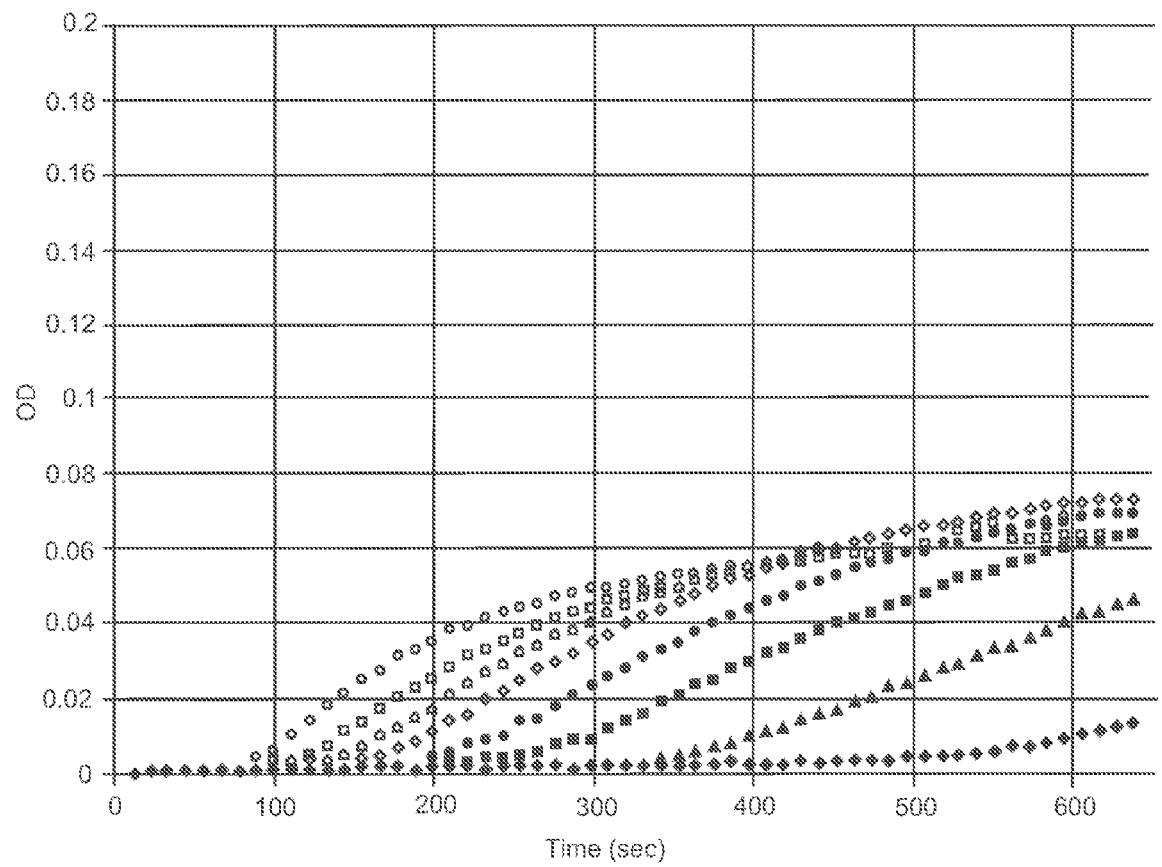

FIG. 8. Depicts the inhibition of fibrinogen clotting assays by mini-hirudin 1 and mini-hirudin 2. See further descriptions below:

FIG. 8a. Inhibition of fibrinogen clotting by the thrombin inhibitor mini-hirudin 1.

Figure 8B:
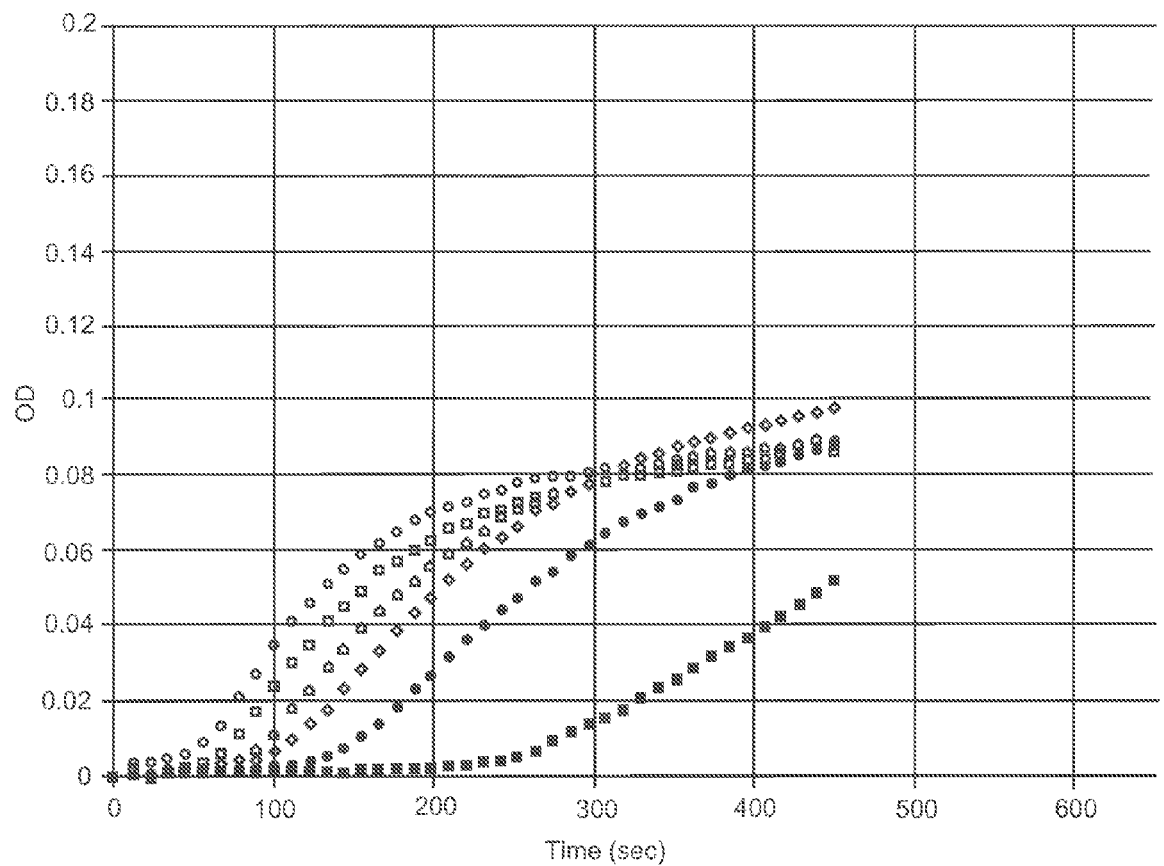

FIG. 8b. Inhibition of fibrinogen clotting by the thrombin inhibitor mini-hirudin 2.

Figure 8C:
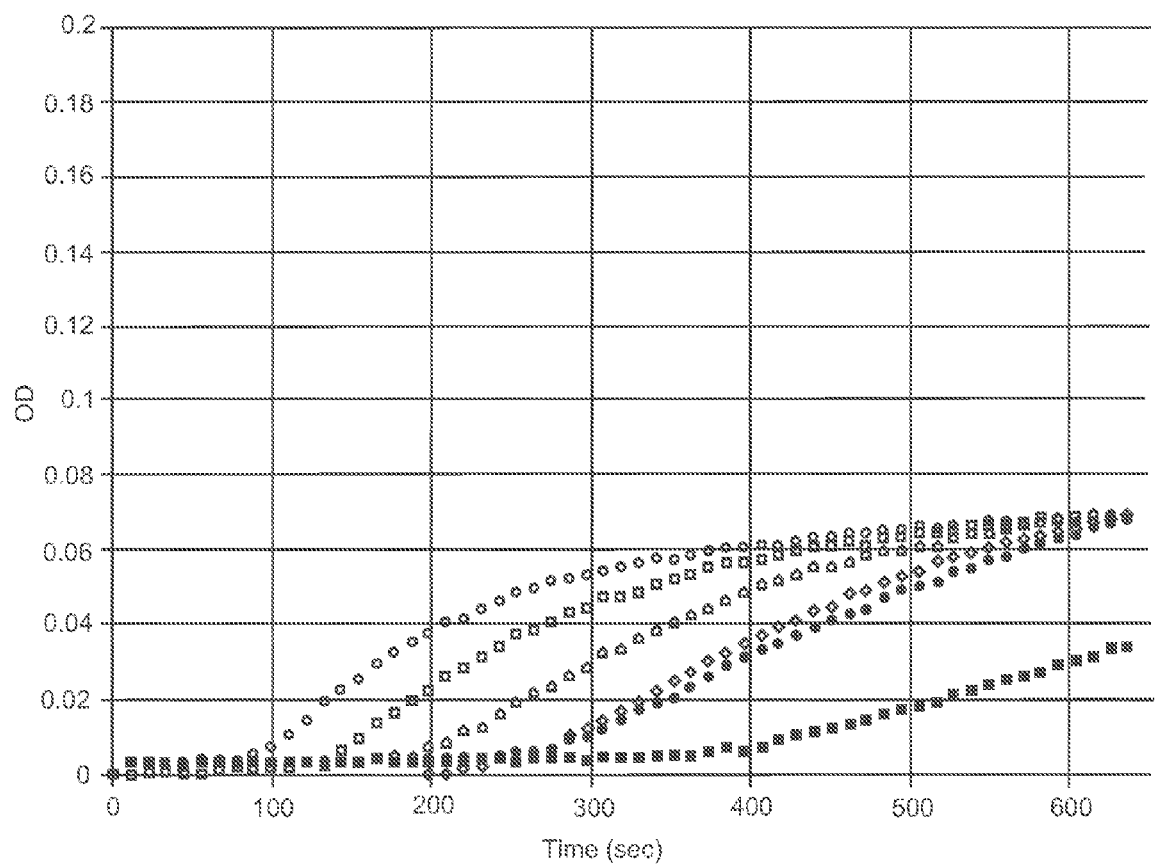

FIG. 8c. Inhibition of fibrinogen clotting by the thrombin inhibitor mini-hirudin 3.

FIG. 9. Amino acid sequences of the CaM-DTI (SEQ ID NO: 21) and CaM-DTI2 (SEQ ID NO: 117) protein(s).

FIG. 10. (A) Inhibition of the amidolydic activity of thrombin by CaM-DTI in the absence of Ca$^{2+}$ (circle) and in the presence of 5 mM Ca$^{2+}$ (square). (B) Inhibition of the amidolytic activity of thrombin by CaM-DTI2.

Figure 11:
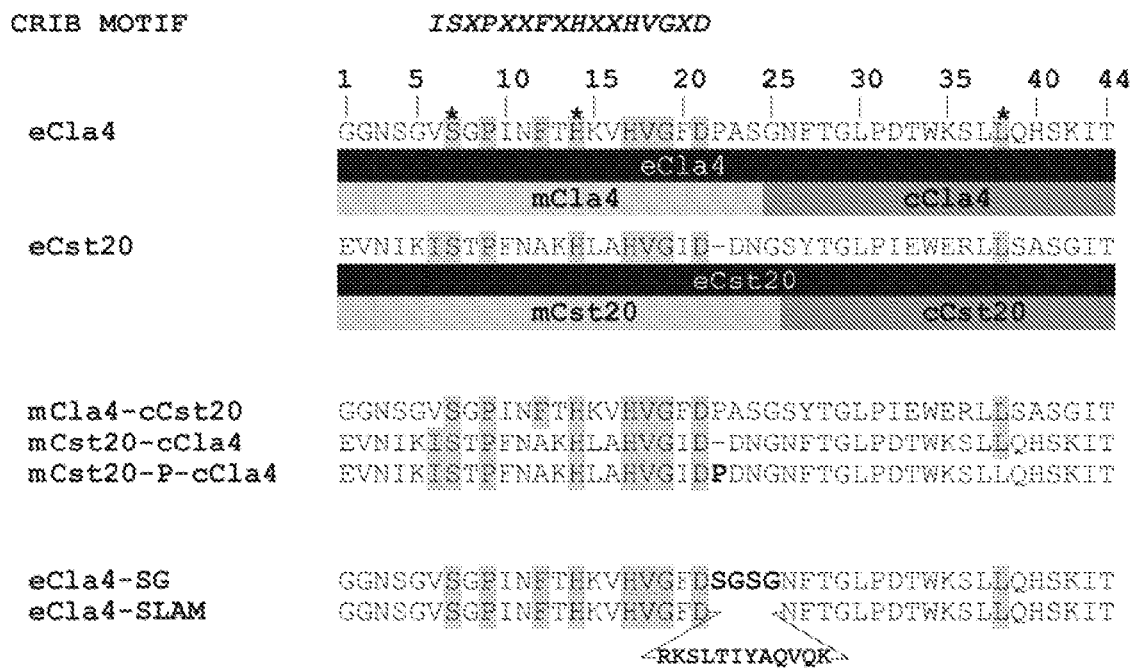

FIG. 11. Depicts a summary of the CRIB-containing peptide fragments and their hybrids—CRIB MOTIF (SEQ ID NO: 26), eCla4 (SEQ ID NO: 37), eCst20 (SEQ ID NO: 38), mCla4-cCst20 (aa 1-25 of SEQ ID NO: 37 fused to aa 25-43 of SEQ ID NO: 38), mCst20-cCla4 (aa 1-24 of SEQ ID NO: 38 fused to aa 26-44 of SEQ ID NO: 37), mCst20-cCla4 (aa 1-24 of SEQ ID NO: 38 fused to aa 26-44 of SEQ ID NO: 37 through P), eCla4-SG (SEQ ID NO: 37 with the reverse of SEQ ID NO: 50 inserted between aa's 21 and 22), and eCla4-SLAM (SEQ ID NO: 130).

Figure 12:
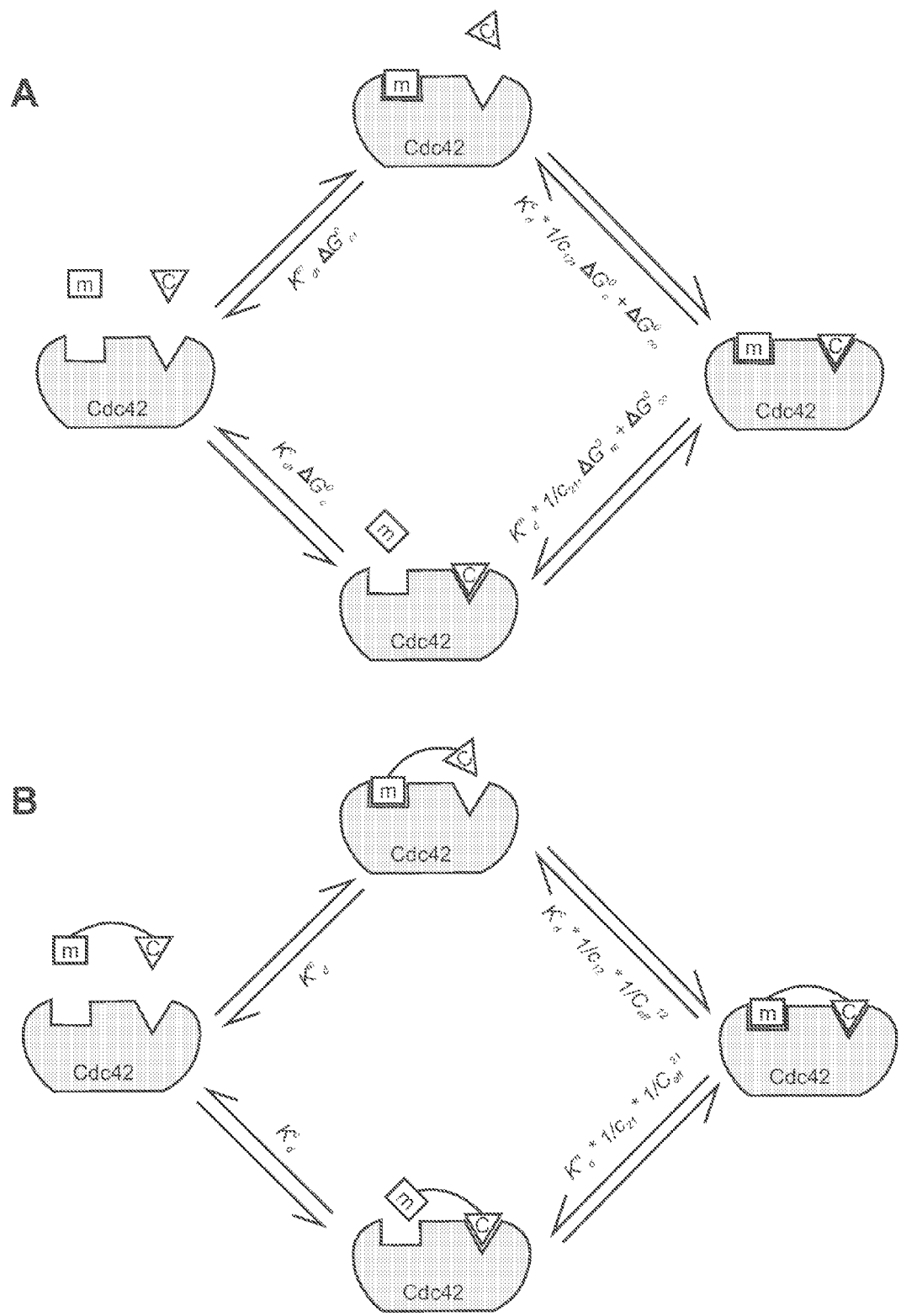

FIG. 12. Depicts a bivalency model for two-site binding between extended CRIB peptides and Cdc42.

Figure 13:
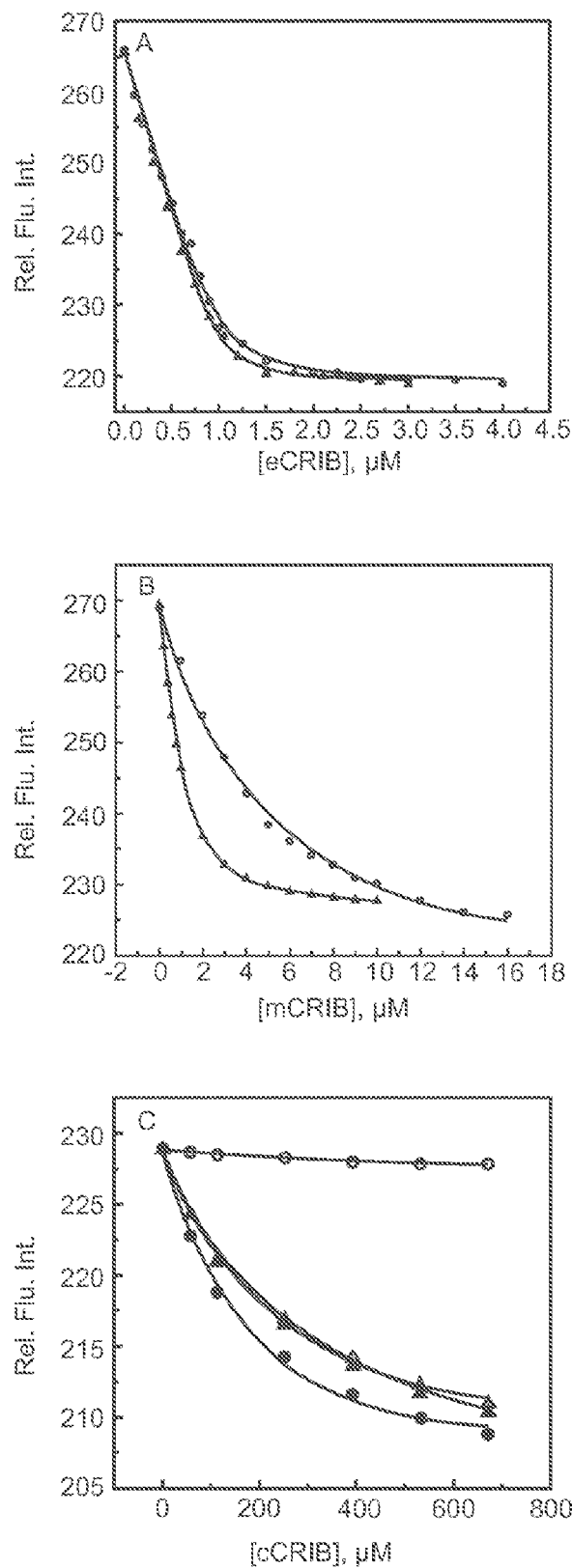

FIG. 13. Depicts fluorescence titration of sNBD-labeled and GMPPCP-loaded CaCdc42 (R150K) with different CRIB peptides.

FIG. 14. FIGS. 14A and 14B depict fluorescence titration assays of a SLAM-binding SH12 with an extended CRIB peptide containing the SLAM sequence as linker. FIGS. 14C, 14D and 14E depict inhibition of fibrinogen clotting assays for a bivalent thrombin inhibitor containing the SLAM peptide sequence as linker.

FIG. 15. Depicts an embodiment of the preparation of conjugated stable complexes between Cdc42 and some extended CRIB peptides.

Figure 15A:
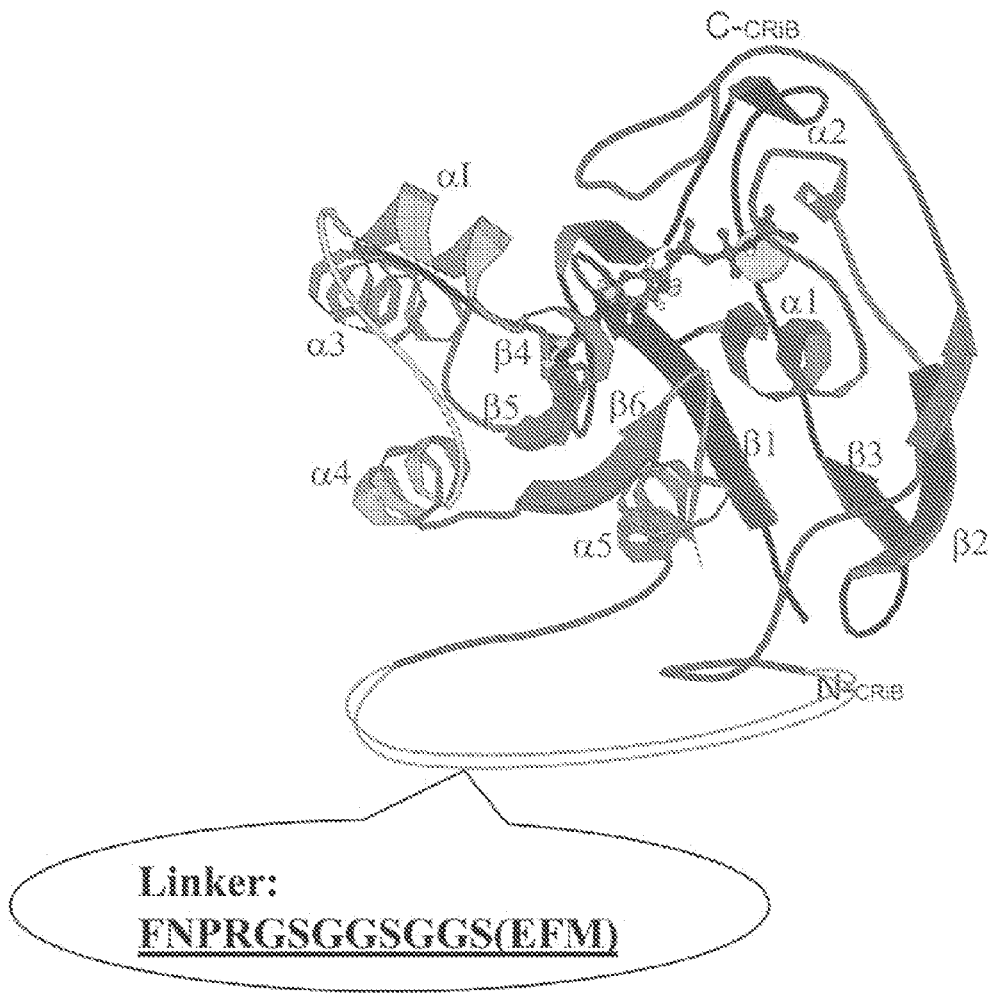
Figure 15B:
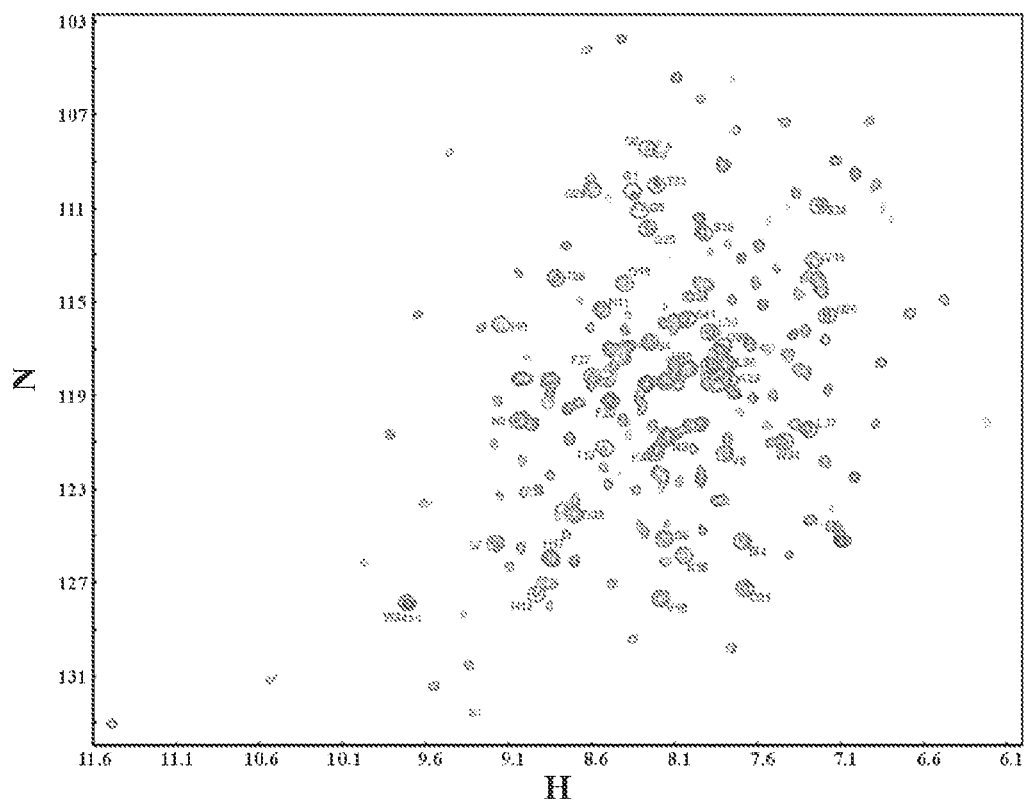

FIG. 15b. Proton-15N NMR HSQC spectrum of the conjugated eCla4-CaCdc42 complex

Figure 15C:
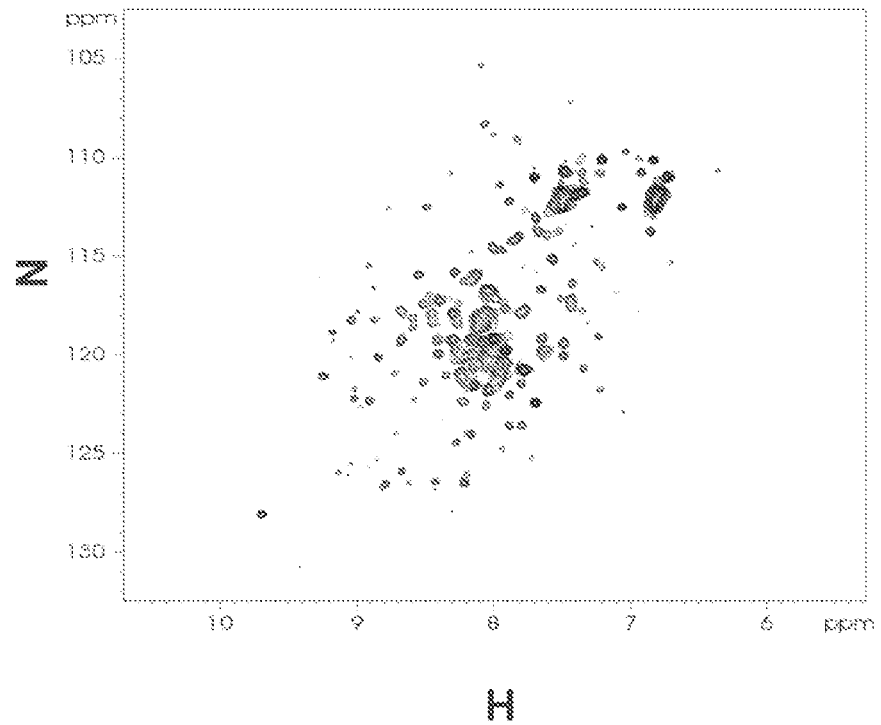

FIG. 15c. Proton-15N NMR HSQC spectrum of the conjugated eCst20-CaCdc42 complex

Figure 15D:
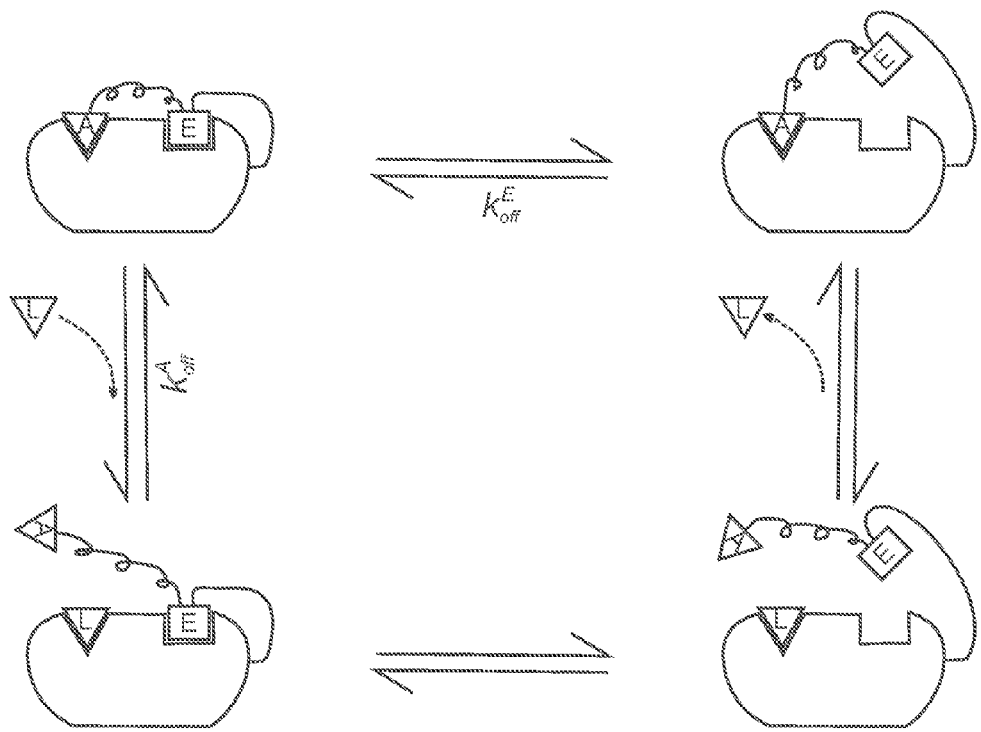

FIG. 15d. Local dissociation of a bivalent ligand conjugated to the binding protein by a monovalent (L) molecule FIG. 16. Depicts a utility of a bivalent polypeptide with a controllable polymeric linker in the fabrication of biomolecular devices remotely activatable by radio frequency magnetic fields (RFMF).

FIG. 16b. Activation of a bivalent ligand by localized heating of the conjugated binding protein FIG. 16c. Activation of a bivalent ligand by localized heating of the linker moiety FIG. 17. Is a schematic depiction of a utility of a bivalent polypeptide with a controllable polymeric linker in the dissection of cell-signaling pathways.

Figure 18:
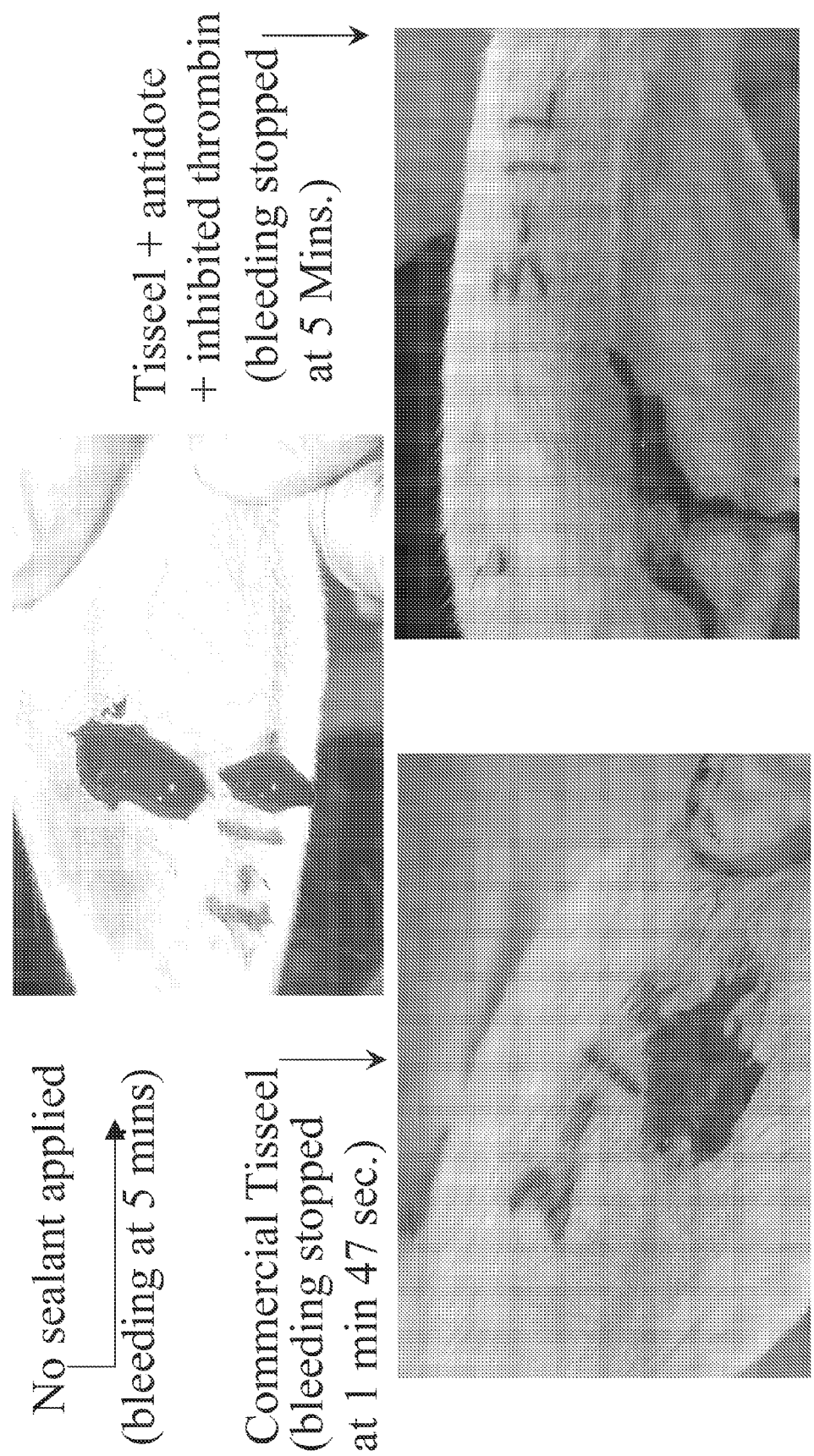

FIG. 18. Depicts photographic data relating to the arrest of arterial bleeding facilitated by fibrin glue application.

DETAILED DESCRIPTION OF THE PREFERRED EMBODIMENTS

Figure 1B:
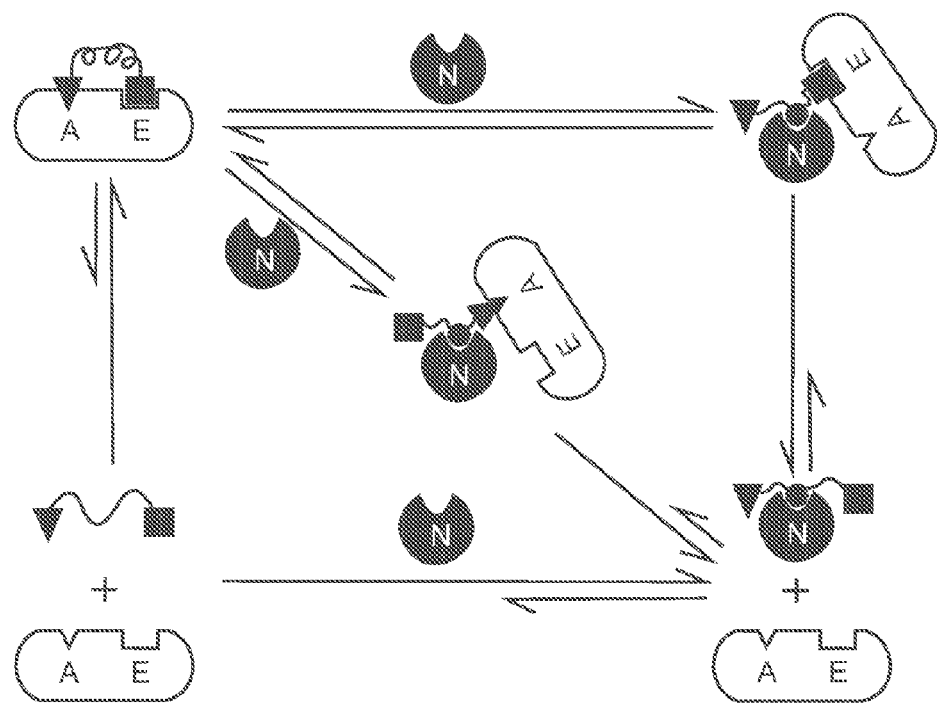

There is disclosed herein an approach combining independent binding moieties in a single molecular structure, which couples binding affinity to an on/off or modulatable switch. There is provided a molecule which contains two or more binding moieties (or "heads") (FIG. 1) joined by a linker. Looking at the embodiment of FIG. 1, each binding moiety in isolation provides only moderate to weak binding affinity (typically up to hundreds of millimolar in dissociation constants) to its specific binding site on a biomolecular target as compared to binding affinity in a bivalent or multivalent complex. When linked together a resulting bivalent ligand binds to its target with a significantly increased affinity (in some instances at least about twice the affinity, in some instances at least about three times, in some instances at least about five times, in some instances at least about ten times.). A change in flexibility of the linker caused by its non-covalent binding to a linker-specific molecule, covalent modification of the linker, or ambient environmental change leads to a decrease or complete disruption of the molecule's ability to bind the target in a bivalent or multivalent mode (FIG. 1). Vise versa, removal of constraints imposed on the linker can restore the high-affinity binding of the freed bivalent ligand. From a thermodynamic point of view, binding of a linker-specific well-structured protein (labelled by "N") confers on the polymeric linker a well-defined conformation enabling for the interaction, which substantially prevents the ligand from acting in a bivalent fashion (FIG. 1B). Each binding moiety in isolation preferably has only low-affinity and transient interactions with an intrinsic dissociation constant up to the high millimolar range for its specific binding site on a target biomacromolecule. When linked together, the resulting bivalent or multivalent molecule makes a substantially stable complex with the target, achieving enhancement of preferably a minimum of two (2) fold in overall binding affinity as compared to the highest affinity of the constituent monovalent ligands. In the design disclosed herein, a polymeric linker is preferably used, such that on one hand, it allows both binding heads to settle freely in their binding sites on a macromolecular target, thereby improving the stability of the complex upon simultaneous occupation of the two individual binding sites. The linker can also be optimized to be selectively responsive to each or a combination of external signals. Since the specifics of the molecular structure of the polymeric linker would not be crucial for the binding association between the bivalent ligand and the target, the linkers and the pairs of binding "heads" are in principle interchangeable, allowing for a number of practical applications. It would be apparent to one skilled in the art, in light of the disclosure herein, how to select a suitable linker and binding heads for a specific purpose.

Feasibility and generality of this approach are assured by the abundance of pharmaceutically important proteins with multiple or forming large binding surface areas, e.g. thrombin and Cdc42. In addition, many of these proteins bind unfolded polypeptides, the latter becoming structured only when in complex with target proteins. These target proteins in particular are suitable for binding bivalent/multivalent ligands or serve as switching or modulating devices through binding to the polymeric linkers in tweezer-like bivalent or multivalent ligands.

As used herein the term "polymeric linker" includes an oligomeric or a polymeric linker without a well-defined three-dimensional structure in the free state of a ligand. Such linkers are capable of connecting a variety of binding moieties and have sufficient length and flexibility to allow simultaneous binding of the individual moieties, enabling a higher binding affinity to the desired molecular target than the affinity of each moiety taken alone. As used herein, the term "controllable polymeric linker" refers to a polymeric linker which allows external control of its flexibility or conformation. The loss or decrease of flexibility or change in conformation of the linker preferably impedes simultaneous binding of the binding moieties, thus producing a reversing effect on the enhanced affinity. Accordingly, the linker will generally be chosen and optimized for the affinity-reversing external signal instead of being optimized to achieve the highest affinity of binding of the ligand to its target.

In an embodiment of the invention the controllable linker is a flexible peptide or peptide bound to another material. The linker will sometimes preferably also be a ligand to a well-structured macromolecular species, or an antidote. For example, many signaling proteins, or their subdomains are known to bind flexible peptides (Pawson and Linding, 2005, 1808-1814; Pawson and Nash, 2003, 445-452; Puntervoll and others, 2003, 3625-3630) conferring upon the latter a structure required for antidote effects. Once bound, such structured linkers will generally produce spatial orientation of binding moieties that will preclude simultaneous binding of the latter to the original target. Occasionally, the linkers may exhibit some molecular interactions with the targets. In some other cases, linker-bound antidotes may produce steric hindrance of their own with the targets in conflicts with a potential bivalent mode of ligand binding. In some cases, an antidote may bind to both the polymeric linker and to a binding moiety. These influences can make additional contributions to reversing the bivalent binding upon antidote complexation. Regardless, in all these cases the linker can still be optimized according to its interaction with the antidote to achieve the desired affinity-reversing effect.

Approaches Taken in the Specific Examples

Tolerance of the bivalent mode of inhibition to the properties of the linking sequences is shown in the examples by a series of inhibitors of thrombin containing an active site binding moiety Bbs-Arg-(D-Pip)-Gly [H1, Bbs=4-tert-butyl-benzenesulfonyl, D-Pip=D-pipecolic acid, $K_I$ in low μM range (Slon-Usakiewicz and others, 2000, 2384-2391)] and an exosite 1 binding moiety Gly-Asp-Phe-Glu-Glu-Ile-Pro-Glu-Glu-Tyr-Leu-Gln (SEQ. ID. NO. 1) derived from the C-terminal tail of hirudin (H2, $K_I$ in low µM range). The H1 and H2 heads are linked by a variety of flexible sequences producing bivalent thrombin inhibitors with a general formula of Bbs-Arg-(D-Pip)-linker-Gly-Asp-Phe-Glu-Glu-Ile-Pro-Glu-Glu-Tyr-Leu-Gln (SEQ. ID. NO. 2), where the linker is an amino acid sequence. With the wide range of linker lengths $IC_{50}$ values of the bivalent inhibitors in fibrinogen clotting assays catalyzed by thrombin remained between 0.3 and 3 nM (Table 1 and FIG. 2), which are sufficient for peptide-based antithrombotic agents, and much lower than the $K_I$ values of the constituent binding moieties. In these specific examples, the C-terminal portion of the bivalent peptides consisted of only natural amino acids and included the polymeric linker plus the H2 moiety [-linker-Gly-Asp-Phe-Glu-Glu-Ile-Pro-Glu-Glu-Tyr-Leu-Gln] (SEQ. ID. NO. 3), which can be produced using recombinant methods. Linking of the H1 moeity, containing unnatural amino acids, with the rest of the peptide was performed using standard disulfide coupling techniques. For example, peptides with amino acid sequences of Bbs-Arg-(D-Pip)-Gly-Cys (SEQ. ID. NO. 4) and Cys-(Gly-Ser)$_8$-Gly-Asp-Phe-Glu-Glu-Ile-Pro-Glu-Glu-Tyr-Leu-Gln (SEQ. ID. NO. 5) were synthesized and purified. A product of disulfide-bonded linkage between peptides Bbs-Arg-(D-Pip)-Gly-Cys (SEQ. ID. NO. 6) and Cys-(Gly-Ser)$_8$-Gly-Asp-Phe-Glu-Glu-Ile-Pro-Glu-Glu-Tyr-Leu-Gln (SEQ. ID. NO. 7) was tested for $IC_{50}$ in the fibrinogen clotting assay. It was established that the two-chain peptide was potent and therefore bivalent with an $IC_{50}$ of 1.1±0.2 nM (FIG. 2). A variety of amino acid sequences with high complexity, originating from naturally-occurring proteins, or binding to naturally-occurring macromolecules, was introduced between the two binding heads producing potent inhibitors. It is noted that the use of only natural amino acids is not essential and non-natural amino acids and chemically modified amino acids (natural or non-natural) are also specifically contemplated for use in the design of controllable bivalent peptides.

Looking at the results of FIG. 2, the assay employs bovine plasma fibrinogen dissolved at 0.1% in 50 mM Tris-Cl, 100 mM NaCl, 0.1% PEG-8000 at pH 7.6. Curves represent $OD_{420}$ time course after the addition of 0.6 nM thrombin in the presence of (♦) 0 nM; (○) 0.5 nM; (□) 1 nM; (Δ) 1.5 nM; (◇) 2.5 nM; (●) 3.75 nM; (■) 6.25 nM; and (▲) 12.5 µM of the inhibitor with linker (GS)$_n$ and n=2 (SEQ. ID. NO. 50) (a); n=4 (SEQ. ID. NO. 51) (b); n=6 (SEQ. ID. NO. 52) (c); n=8 (SEQ. ID. NO. 53) (d); n=10 (SEQ. ID. NO. 54) (e); and in the presence of (♦) 0 nM; (○) 1 nM; (□) 2 nM; (Δ) 4 nM; (◇) 6 nM; (●) 10 nM; (■) 15 nM; and (▲) 25 nM of the inhibitor with linker (GS)$_n$ and n=12 (SEQ. ID. NO. 55) (f); n=14 (SEQ. ID. NO. 56) (g), at 37° C. The onset clotting time was determined as an intersection of the baseline and the extrapolated linear portion of the OD change curve. Extracted $IC_{50}$ values are shown in Table 1. Curves (h) represent $OD_{420}$ time course in the presence of (■) 0 nM; (○) 1 nM; (□) 3 nM; (Δ) 5 nM; (◇) 7 nM; and (●) 9 nM of a product of disulfide-bonded linkage between peptides Bbs-Arg-(D-Pip)-Gly-Cys and Cys-(Gly-Ser)$_8$-Gly-Asp-Phe-Glu-Glu-Ile-Pro-Glu-Glu-Tyr-Leu-Gln (SEQ. ID. NO. 83), at 37° C. Curves (i) represent $OD_{420}$ time course in the presence of (A) 0 nM; (○) 1 nM; (□) 2 nM; (Δ) 4 nM; (◇) 6 nM; and (●) 15 nM of the inhibitor with linker GTLDLNTPVDKTSN (SEQ. ID. NO. 103), at 37° C. Curves (o) represent $OD_{420}$ time course in the presence of (○) 0 nM; (□) 2 nM; (Δ) 4 nM; (◇) 6 nM; (●) 8 nM; (■) 10 nM; (▲) 12 nM; and (♦) 15 nM; of the inhibitor with linker GSGSGSGSGKGSGSGSGSGS (SEQ. ID. NO. 58) at 25° C. Curves (k) represent $OD_{420}$ time course in the presence of (○) 0 nM; (□) 0.5 nM; (Δ) 1 nM; (◇) 2 nM; (●) 3 nM; (■) 4 nM; (▲) 5 nM; and (♦) 6 nM; of the inhibitor with linker GSVVPRPQLHND (SEQ. ID. NO. 105) at 37° C. Curves (I) represent $OD_{420}$ time course in the presence of (○) 0 nM; (□) 0.25 nM; (Δ) 0.5 nM; (◇) 1 nM; (●) 1.5 nM; (■) 2 nM; and (▲) 2.5 nM; of the inhibitor with linker GSHAPRPQIHND (SEQ. ID. NO. 104) at 37° C. Curves (m) represent $OD_{420}$ time course in the presence of (○) 0 nM; (□) 2 nM; (Δ) 4 nM; (◇) 6 nM; (●) 8 nM; (▲) 10 nM; and (A) 12 nM; of the inhibitor with linker GHHLGGAKQAGDV (SEQ. ID. NO. 106) at 37° C. Curves (n) represent $OD_{420}$ time course in the presence of (○) 0 nM; (□) 1 nM; (Δ) 2 nM; (◇) 3 nM; (●) 4 nM; (■) 5 nM; (▲) 6 nM; and (♦) 7 nM; of the inhibitor with linker GYMESRADR (SEQ. ID. NO. 107) at 37° C. Curves (o) represent $OD_{420}$ time course in the presence of (○) 0 nM; (□) 4 nM; and (Δ) 8 nM; of the inhibitor with linker GQSHNR (SEQ. ID. NO. 108) at 37° C.

For some peptide-based linkers, modifications of amino acid side chains (such as tyrosine, serine or threonine phosphorylation by kinases, or dephosphorylation by phosphatases) will turn these peptides into binding ligands for signaling proteins and signaling protein subdomains or interrupt their specific interactions. The peptide sequence Cys-Pro-His-Tyr-Glu-Lys-Val-Ser-Gly (SEQ. ID. NO. 8) derived from the ephrinB cytoplasmic tail (ephrinB2$_{301-309}$) was used to link the H1 and H2 heads. The peptide is flexible and in its tyrosine-phosphorylated state binds an SH2 domain from the Grb4 adaptor protein with an affinity of 0.2 µM (Su, Xu, and Ni, 2004b, 1725-1736). Four peptides of a general formula Bbs-Arg-(D-Pip)-Gly-(Ser-Pro-His-B-Glu-Lys-Val-Ser-Gly)n-Asp-Phe-Glu-Glu-Ile-Pro-Glu-Glu-Tyr-Leu-Gln (SEQ. ID. NO. 9) were produced, wherein B was either tyrosine (Tyr) or O-phosphotyrosine (Tyr(P)), and n was 1 or 2. $IC_{50}$ of the inhibitors in the fibrinogen clotting assay were comparable and in the vicinity of 0.5-1 nM, except for the peptide with two phosphotyrosines which had an $IC_{50}$ of 18-20 nM (Table 1, FIG. 3).

Looking at the results of FIG. 3, the curves represent $OD_{420}$ time course after the addition of 0.6 nM thrombin in the presence of (♦) 0 nM; (○) 1 nM; (□) 2 nM; (Δ) 4 nM; (◇) 6 nM; (●) 10 nM; (■) 15 nM; and (▲) 25 nM of inhibitor for n=1, B=Y (a); n=1, B=Y(P) (b); n=2, B=Y (c); n=2, B=Y(P) (d); at 25° C. Other experimental conditions were as used for the assays described in FIG. 2. Extracted $IC_{50}$ values are shown in Table 1.

To reverse the inhibitory potency of the peptides they were brought in contact with the SH2 domain in solution. Presence of the SH2 domain reversed the inhibitory potency of the Bbs-Arg-(D-Pip)-Gly-(Ser-Pro-His-Tyr(P)-Glu-Lys-Val-Ser-Gly)n-Asp-Phe-Glu-Glu-Ile-Pro-Glu-Glu-Tyr-Leu-Gln peptide ((SEQ. ID. NO. 10), corresponding to (SEQ. ID. NO. 9) when B is Tyr (P)), but not that of Bbs-Arg-(D-Pip)-Gly-(Ser-Pro-His-Tyr-Glu-Lys-Val-Ser-Gly)n-Asp-Phe-Glu-Glu-Ile-Pro-Glu-Glu-Tyr-Leu-Gln peptide ((SEQ. ID. NO. 11), corresponding to (SEQ. ID. NO. 9) when B is Tyr) (FIG. 4). The change in thrombin inhibitory activity upon binding of SH2 makes it useful in an assay for protein-to-peptide binding, which in some embodiments could be implemented in a high-throughput manner.

Looking at the results of FIG. 4, peptide inhibitors were designated in Table 1 as P3161 (n=2, B=Y); P3162 (n=2, B=Y(P)); P3169 (n=1, B=Y); and P3170 (n=1, B=Y(P)). The curves represent $OD_{420}$ time course after the addition of 0.6 nM thrombin in the presence of (a) (○) 2 nM P3161; (□) 2 nM P3161, 3 µM SH2; (Δ) 50 nM P3162; (◇) 50 nM P3162, 3 µM SH2; (●) no inhibitor, no SH2; (Δ) no inhibitor, 3 µM SH2; and (b) (○) 1 nM P3169; (□) 1 nM P3169, 3 µM SH2;

(Δ) 4 nM P3170; (◇) 4 nM P3170, 3 μM SH2; (●) no inhibitor, no SH2; (■) no inhibitor, 3 μM SH2. Other experimental conditions were as used for assays described in FIG. 3.

In another case a peptide linker Glu-Gln-Lys-Leu-Ile-Ser-Glu-Glu-Asp-Leu (also called the c-myc sequence, SEQ. ID NO. 12) known to bind an anti-c-myc antibody 9E10 with an affinity of approximately 0.5 μM (Hilpert at al. 2001, 803-806) was built into the bivalent thrombin inhibitor Bbs-Arg-(D-Pip)-Gly-Glu-Gln-Lys-Leu-Ile-Ser-Glu-Glu-Asp-Leu-Gly-Asp-Phe-Glu-Glu-Ile-Pro-Glu-Glu-Tyr-Leu-Gln (SEQ. ID. NO. 13). The antibody 9E10 reversed the inhibitory potency of the inhibitor (FIG. 5).

Looking at the results of FIG. 5, the curves represent $OD_{420}$ time course in the presence (□,■) or absence (○,●) of 150 nM of the inhibitor. Addition of ~1.2 μM anti-c-myc antibody 9E10 (Sigma) only slightly slowed clotting of free thrombin (○), but reversed the inhibitory effect of the inhibitor (□). Other experimental conditions were as used for assays described in FIG. 3.

In other cases, disulfide bonds can be formed or opened to rigidify or make the linkers more flexible. Limited specific proteolysis may turn a well-folded disulfide-bonded peptide into a polymeric linker, allowing for bivalent binding. In other instances amino acid side chain modifications producing two or more charged groups (as in the case of phosphorylation of an amino acid side chain) in the linker will generate electrostatic repulsion or attraction affecting the linker's flexibility and the end-to-end statistically average distance.

Incorporation of two phosphotyrosines in the polymeric linker of the peptide with the sequence Bbs-Arg-(D-Pip)-Gly-(Ser-Pro-His-Tyr(P)-Glu-Lys-Val-Ser-Gly)$_2$-Asp-Phe-Glu-Glu-Ile-Pro-Glu-Glu-Tyr-Leu-Gln ((SEQ. ID. NO. 14), corresponding to (SEQ. ID. NO. 10) when n=2) produced a significant drop in inhibition potency as compared to the dephosphorylated analog (FIG. 3). The potency of the bivalent inhibitor generally depends on the phosphorylation state of the linker. Thus, kinase or phosphatase activities can be converted into serine protease (thrombin) activity in a coupled enzymatic assay in light of the disclosure herein. In such an assay, the linker preferably contains tyrosine, or other residues that can be phosphorylated or dephosphorylated after phosphorylation. Therefore, reversible and irreversible posttranslational modifications of the linker can be used as another mechanism of controlling ligand (inhibitor) affinity.

Some flexible peptides will bind metal ions specifically (FIG. 6). Organization of metal ion coordination sphere will change the flexibility of the peptides achieving the required affinity control. For example, a peptide Bbs-Arg-(D-Pip)-Gly-Cys . . . Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ. ID. NO. 91) was prepared through coupling of two peptides, Bbs-Arg-(D-Pip)-Gly-Cys (SEQ. ID. NO. 15) and Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ. ID. NO. 16) by means of a disulfide bond. The linker moiety of the bivalent peptide contains the sequence segment Asp-Lys-Asn-Ala-Asp-Gly-Trp-Ile-Asp-Asn-Gly-Asp-Phe-Glu (SEQ. ID. NO. 17) that binds calcium(II) with an affinity in the millimolar range. Calcium(II) addition altered inhibition of chromogenic substrate proteolysis by human α-thrombin observed in the presence of the peptide (FIG. 7).

Looking at the results in FIG. 6, panels a, b, c, d show changes in the proton NMR spectra of Ac-Asp-Lys-Asn-Ala-Asp-Gly-Trp-Ile-Asp-Asn-Gly-Asp-Phe-Glu-NH$_2$ (SEQ. ID. NO. 109) (P3230, panels a, b) and Ac-Asp-Lys-Asn-Ala-Asp-Gly-Trp-Ile-Asp-Asn-Gly-Asp-Phe-Glu-NH$_2$ (SEQ. ID. NO. 110) (P3231, panels c, d) upon the addition to the initial ~450 μL of the corresponding peptide in 20 mM sodium acetate-d$_3$ buffer, pH 5.5, containing 10% D$_2$O, of 1 μL (final CaCl$_2$ concentration ~0.22 mM), additional 2 μL (final CaCl$_2$ concentration ~0.66 mM), additional 10 μL (final CaCl$_2$ concentration ~2.8 mM) of 100 mM CaCl$_2$, and additional 10 μL (final CaCl$_2$ concentration ~23.9 mM) of 1 M CaCl$_2$. Panels e and f show changes in the proton NMR spectrum of a disulfide-linked peptide Bbs-Arg-(D-Pip)-Gly-Cys . . . Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ. ID. No. 16) upon the addition to the initial volume of ~450 μL of 1 μL (final CaCl$_2$ concentration ~0.22 mM), additional 2 μL (final CaCl$_2$ concentration ~0.66 mM) of 100 mM CaCl$_2$, and additional 10 μL (final CaCl$_2$ concentration ~22.2 mM) of 1 M CaCl$_2$.

Looking at the results in FIG. 7, the effect was tested in the presence of two bivalent thrombin inhibitors, the calcium-binding Bbs-Arg-(D-Pip)-Gly-Cys . . . Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ. ID. No. 16) (CaR), and control peptide Bbs-R-(D-Pip)-GSGSGSGS-GDFEE-IPEEYLQ (SEQ. S10) (P3150). Curves represent $OD_{405}$ time course at 25° C. after the addition of 0.6 nM thrombin to 50 mM S-3266 (Chromogenics) in the clotting buffer, and in the presence of (○) no inhibitors; (□) 150 nM CaR; (Δ) 150 nM CaR, 50 mM CaCl$_2$; (◇) 150 nM CaR, 100 mM CaCl$_2$; (●) 2 nM P3150; (■) 2 nM P3150, 50 mM CaCl$_2$; and (▲) 2 nM P3150, 100 mM CaCl$_2$.

Polypeptides containing only natural amino acids can also be used as starting points for the generation of a bivalent ligand with a controllable linker. In order to design a ligand with a controllable linker, at least two binding heads of adequate affinities to two distinct sites on a target should preferably be known. The binding heads can be discovered through ab initio screening or minimization of structurally or functionally characterized polypeptide interactions with its target. Outlining minimal regions of polypeptides capable of binding to their macromolecular targets ("hot spots") may produce a set of at least two peptide sequences, interacting with distinct sites on the target surface. Determination of minimal binding regions ("hot spots") can be carried out using spectroscopic (e.g. NMR spectroscopy) or recombinant (e.g. alanine scan) methods. Through minimization of hirudin two peptides were designed having sequences of Val-Arg-Phe-Thr-Asp-Gly-Glu-Gly-Thr-Pro-Lys-Pro-Gln-Ser-His-Asn-Asp-Gly-Asp-Phe-Glu-Glu-Ile-Pro-Glu-Glu-Tyr-Leu-Gln (mini-hirudin 1) (SEQ. ID. NO. 22) and Ile-Arg-Phe-Thr-Asp-Gly-Glu-Gly-Thr-Pro-Asn-Pro-Glu-Ser-His-Asn-Asn-Gly-Asp-Phe-Glu-Glu-Ile-Pro-Glu-Glu-Tyr-Leu-Gln (mini-hirudin 2) (SEQ. ID. NO. 23) incorporating N-terminal and C-terminal moieties believed to interact with the active site and exosite I of thrombin, respectively. These peptides displayed high potencies for thrombin inhibition with IC$_{50}$ of 33±3 μM (mini-hirudin 1) and 14±1 nM (mini-hirudin 2), indicating a bivalent mode of binding (FIG. 8). The modular character of interaction was further confirmed when a candidacidal peptide known to bind laminarin (Polonelli, L.; and others, 2003, 6205-6212), in other words, the peptide of the sequence -Ala-Lys-Val-Thr-Met-Thr-Cys-Ser-Ala-Ser- (SEQ. ID. NO. 24), was inserted as a linker into mini-hirudin 2 to give mini-hirudin 3 with a sequence of Ile-Arg-Phe-Thr-Asp-Gly-Ala-Lys-Val-Thr-Met-Thr-Cys-Ser-Ala-Ser-Gly-Asp-Phe-Glu-Glu-Ile-Pro-Glu-Glu-Tyr-Leu-Gln (SEQ. ID. NO. 25). The peptide was shown to preserve high affinity of binding to thrombin, with an IC$_{50}$ of 10±1 nM (FIG. 8).

Looking at the results in FIG. 8, curves (a) represent $OD_{420}$ time course in the presence of (○) 0 μM; (□) 10 nM; (Δ) 30 nM; (◇) 50 nM; (●) 70 nM; and (■) 100 nM of mini-hirudin 1 at 37° C. Curves (b) represent $OD_{420}$ time course in the presence of (○) 0 nM; (□) 4 nM; (Δ) 8 nM; (◇) 12 nM; (●) 20 nM; (■) 30 nM; (▲) 50 nM; and (♦) 100 nM of mini-hirudin 2 at 37° C. Curves (c) represent $OD_{420}$ time course in the presence of (○) 0 nM; (□) 2.15 nM; (Δ) 4.3 nM; (◇) 8.6 nM; (●) 17.2 nM; and (■) 43 nM of mini-hirudin3 at 37° C. Other experimental conditions are as used for assays shown in FIG. 2.

The peptide with a sequence of Trp-Asp-Pro-Arg-Pro-Gln-Arg-His-Asn-Asp-Gly-Asp-Phe-Glu-Glu-Ile-Pro-Glu-Glu-Tyr-Leu-Gln (SEQ. ID. NO. 18) is a bivalent molecule with a $K_I$ of ~17 nM for thrombin inhibition. The peptide can be decomposed into two moieties, an active site binding moiety, Trp-Asp-Pro-Arg-Pro-Gln-Arg-His (SEQ. ID. NO. 19), and an exosite-1 binding moiety, Asp-Phe-Glu-Glu-Ile-Pro-Glu-Glu-Tyr-Leu-Gln (SEQ. ID. NO. 20). A thrombin inhibitor was prepared with the sequence of Trp-Asp-Pro-Arg-Pro-Gln-Arg-His-(CamCKK)-Asp-Phe-Glu-Glu-Ile-Pro-Glu-Glu-Tyr-Leu-Gln (SEQ. ID. NO. 21), designated as CaM-DTI, where CamCKK is a protein with calcium-binding properties (see for example Truong, 2001, 1069-1073). The sequence of the CaM-DTI molecule is shown in FIG. 9. As depicted in FIG. 9, the sequence includes at the N-terminus a binding moiety (bold) to the thrombin active site, a binding moiety (italic bold) to the exosite-1 of thrombin at the C-terminus, and a calcium-responsive protein linker. CaM-DTI was prepared with a recombinant DNA approach. Potency of thrombin inhibition by CaM-DTI was determined by an amidolytic assay. Upon the addition of 5 mM $Ca^{2+}$, an increase in apparent $K_I$ from 480 nM (no calcium) to 2200 nM ($Ca^{2+}$) was observed (FIG. 10).

In another case, the small GTPase Cdc42 binds with high-affinities to the ~40-residue extended CRIB domains of the *Candida* Cla4 and Step 20 kinases ($K_D$=20~50 nM) (the latter also known as Cst20). When subjected to NMR relaxation dispersion analysis (Tolkatchev, Xu, and Ni, 2003b, 12432-12442), these complexes exhibit no responses, as expected for a tight binding complex. The full-length CRIB domains were decomposed into two peptide fragments (FIG. 11): (i) mCla4 (mCst20) including the consensus CRIB motif, and (ii) cCla4 (cCst20) which comprises residues directly to the C-terminus of the minimal CRIB sequence. Looking at FIG. 11, the extended CRIB fragments (eCRIBs) comprise the CRIB motif, plus ~20 residues to the C-terminus and exhibit high-affinity binding to CaCdc42. These sequences were dissected into two fragments: the minimal CRIB (mCRIB), mCla4 and mCst20, and the C-terminal CRIB (cCRIB), cCla4 and cCst20. In order to construct a bivalent peptide ligand for *Candida* Cdc42 (CaCdc42) with a suitable linker, the binding affinities of these component peptides derived from the CRIB domains of *Candida* Cla4 and Step 20 were determined. For this purpose, a CaCdc42 expression vector encoding the R150K mutation was constructed and the sequence of the R150K CaCdc42 mutant (Table 4) was verified by DNA sequencing.

FIG. 12 depicts a bivalency model for two-site binding between extended CRIB peptides and Cdc42. This dissectional strategy is used to analyse the interaction of the CRIB fragments with CaCdc42 (A). The m and c represent the mCRIB and the cCRIB fragments, respectively, as defined in FIG. 11. Dissociation constants and corresponding Gibbs free energies are indicated according to the reaction coordinate. (B) depicts the bivalent binding mode of covalently-linked CRIB sub-fragments with Cdc42. The mCRIB and cCRIB sequences are assumed to have the same "intrinsic" binding affinities after linkage. An additional factor $C_{eff}$ is introduced together with the cooperativity factors, $c_{12}$ and $c_{21}$ to define the partial dissociation constants of the individual dissociation steps. The thermodynamic dissociation constant representing complete dissociation of the extended "bivalent" CRIB peptide can be deduced following microscopic equilibria from either one of the two dissociation pathways.

FIG. 13 shows binding isotherms obtained following the CRIB-induced changes in the sNBD fluorescence of the CaCdc42 (R150K) protein. All the titration curves could be best fitted to a simple bimolecular binding model. The average apparent $K_d$ values for different CRIB peptides are summarized in Table 2. As expected, the extended CRIB (eCRIB) fragments exhibited the strongest affinities to CaCdc42 in the low nanomolar range. The mCRIB fragments containing the consensus CRIB sequence, ISXPXXFXHXXHVGXD (SEQ. ID. NO. 26) (Burbelo, P. D., Drechsel, D., and Hall, A., 1995, 29071-29074), also had moderately strong binding affinities in micromolar concentrations, but clearly, as seen previously for the human PAK homologues (Rudolph, M. G., Bayer, P., Abo, A., Kuhlmann, J., Vetter, I. R., and Wittinghofer, A., 1998, 18067-18076; Thompson, G., Owen, D., Chalk, P. A., and Lowe, P. N., 1998, 7885-7891), require extra residues to retain stronger binding to Cdc42. The cCRIB peptides exhibited much weaker affinities to the CaCdc42 protein. The $K_d$ value of cCla4 for binding to CaCdc42 is in a high micromolar concentration (275 μM). An even weaker binding ($K_d$=1160 μM) was observed between cCst20 and CaCdc42 with the current fluorescence titration strategy.

Looking at the results of FIG. 13, one micromolar concentration of sNBD-labeled, and GMPPCP-loaded CaCdc42 (R150K) was titrated with the indicated amounts of CRIB fragments shown in FIG. 11. (A) eCla4 (open circle) and eCst20 (open triangle); (B) mCla4 (open circle) and mCst20 (open triangle), and (C) cCla4 (open circle), cCst20 (open triangle), cCla4 in the presence of 50 μM mCla4 (filled circle) and cCst20 in the presence of 50 μM mCst20 (filled triangle). Solid lines represent fits of the data to a bimolecular association model.

Fluorescence measurements were used to substantiate and quantify the effects of cross-titrations observed by NMR (Table 2). The affinity of the Cla4 peptide fragments for CaCdc42 was not significantly affected by the addition of the cognate peptide. In contrast, the affinities of the Cst20 peptide fragments preincubated with CaCdc42 exhibited a dramatic enhancement in binding for CaCdc42 by ~5.5-fold, upon addition of the cognate Cst20 peptide (Table 2). Thus, upon addition of mCst20 to the cCst20/CaCdc42 complex, the affinity of cCst20 for CaCdc42 increased from a $K_d$ of 1160 μM to 207 μM (Table 2 and FIG. 13c). Similarly, mCst20 affinity for CaCdc42 increased from 0.43 μM to 0.081 μM when cCst20 was added to a preincubated mCst20/CaCdc42 complex. These results strongly suggest that the eCst20 and eCla4 peptides exhibit different mechanisms for binding CaCdc42, in which long eCst20 peptide utilizes a cooperative mechanism for high-affinity interaction while eCla4 does not.

Modular nature of interactions of m- and c-CRIB fragments is emphasized by the binding affinities of hybrid peptides incorporating m- and c-CRIBs from different molecular species. Both mCla4-cCst20 and mCst20-P-cCla4 constructs (FIG. 11) displayed affinities of the same order of magnitude as the original eCRIB peptides (Table 2). Moreover, incorporation of -Ser-Gly-Ser-Gly-(SEQ. ID. NO. 27) and -Arg-Lys-Ser-Leu-Thr-Ile-Tyr-Ala-Gln-Val-Gln-Lys-(SEQ. ID. NO. 28), in other words the SLAM peptide sequence (Li et al and Pawson, Curr. Biol. 9, 1355-1362, 1999) as linkers into the eCla4 sequence preserved a bivalent mode of binding.

Figure 14A:
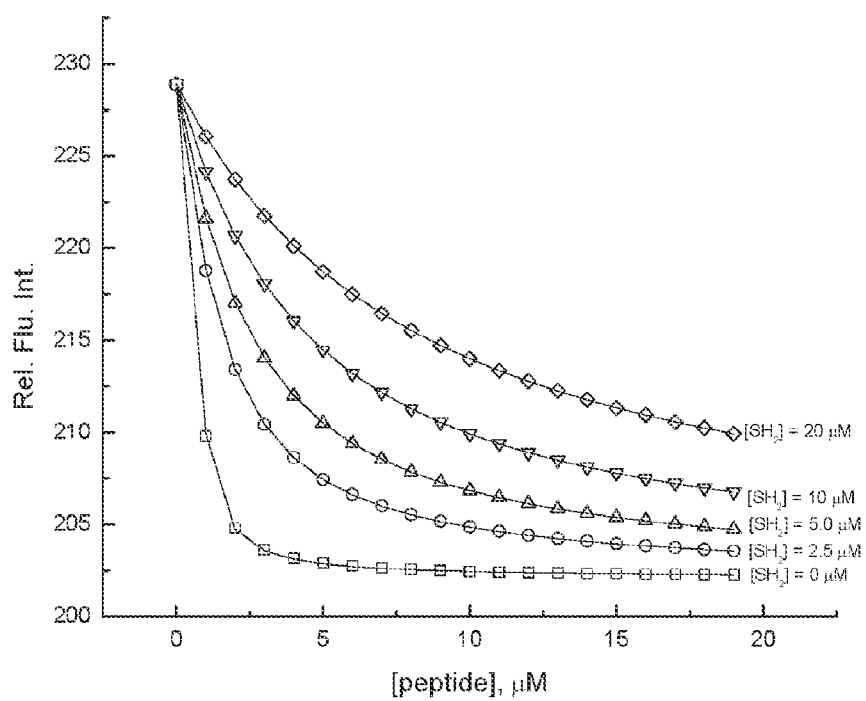
Figure 14B:
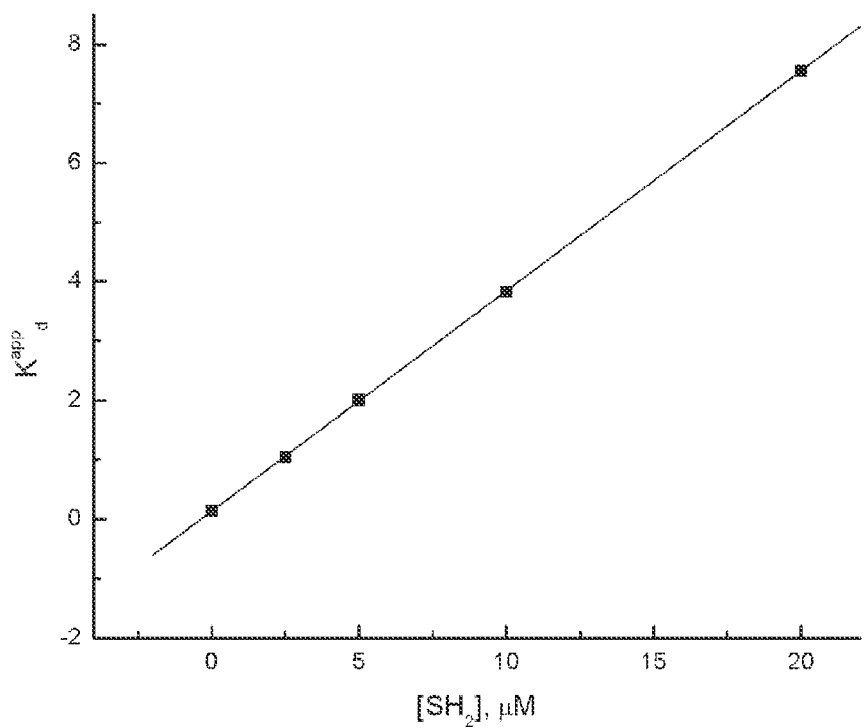

In addition to bivalent binding to CaCdc42, the eCla4-SLAM peptide (FIG. 11 and Table 2) also preserved the binding capacity of the SLAM linker peptide to the SH2 domain derived from the SAP protein (Table 4). FIG. 14A and FIG. 14B depict the competition binding of SAP-SH2 and CaCdc42 to the polypeptide eCla4-SLAM. FIG. 14A shows the effect of including SAP-SH2 at various concentrations on the binding affinity of eCla4-SLAM to CaCdc42 R150K. The concentration of CaCdc42 R150K is 1 µM. FIG. 14B shown that the apparent dissociation constant for the Cdc42-eCla4 complex is a function of the concentration of added SAP-SH2

Figure 14C:
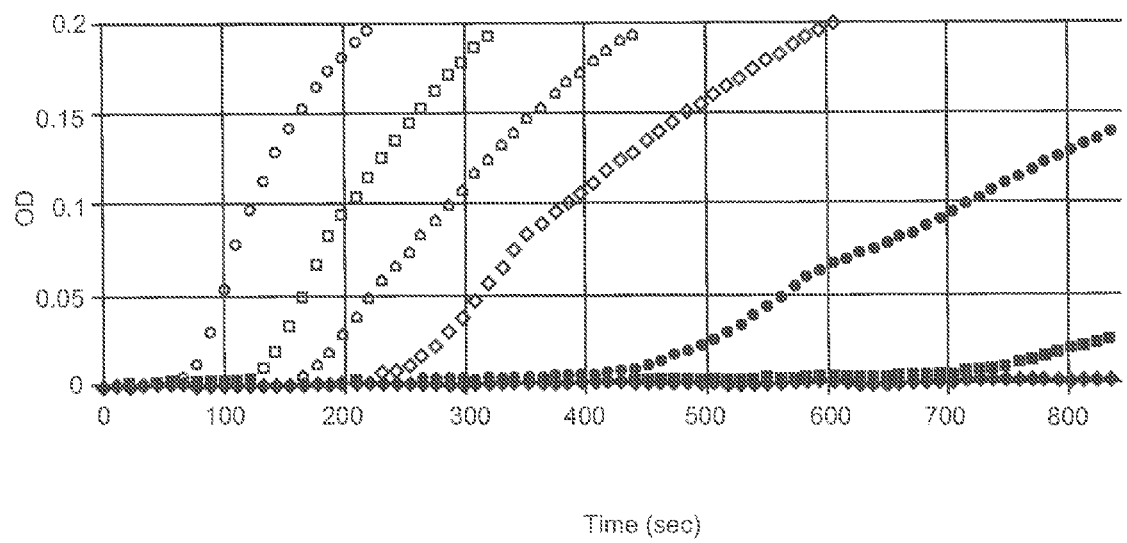
Figure 14D:
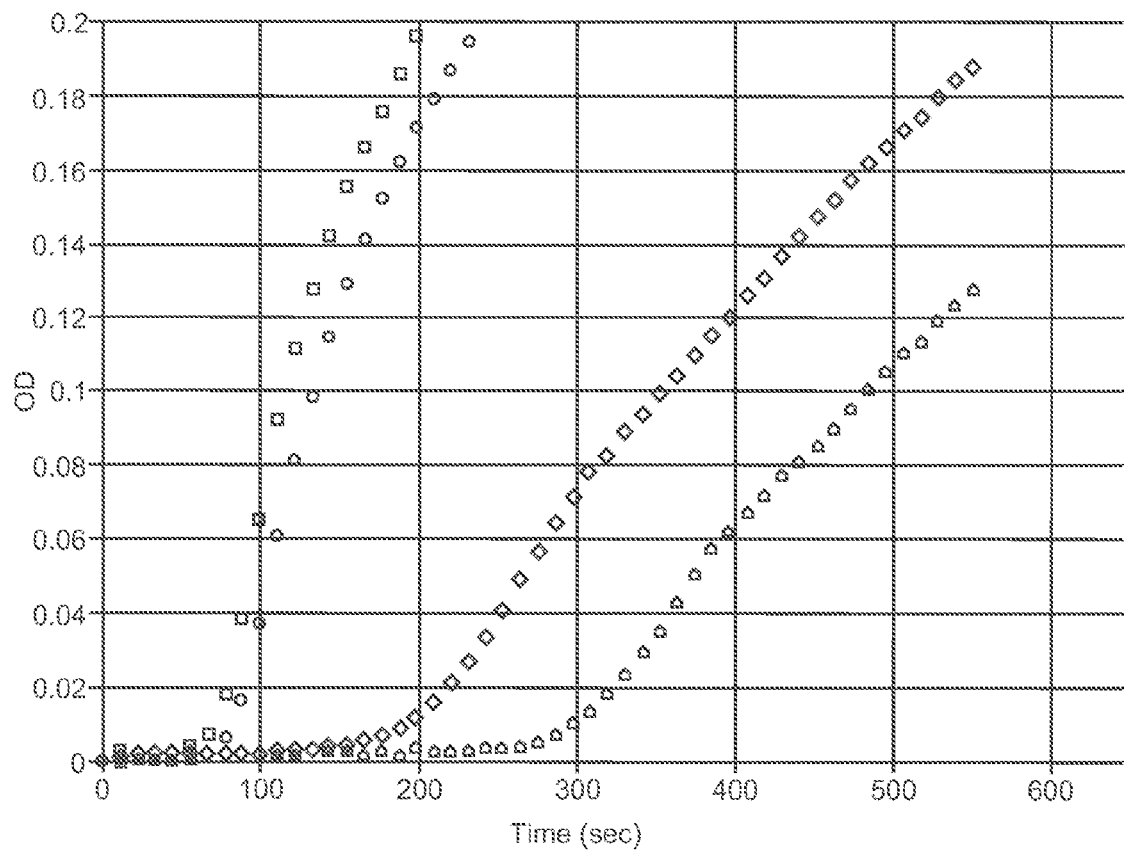
Figure 14E:
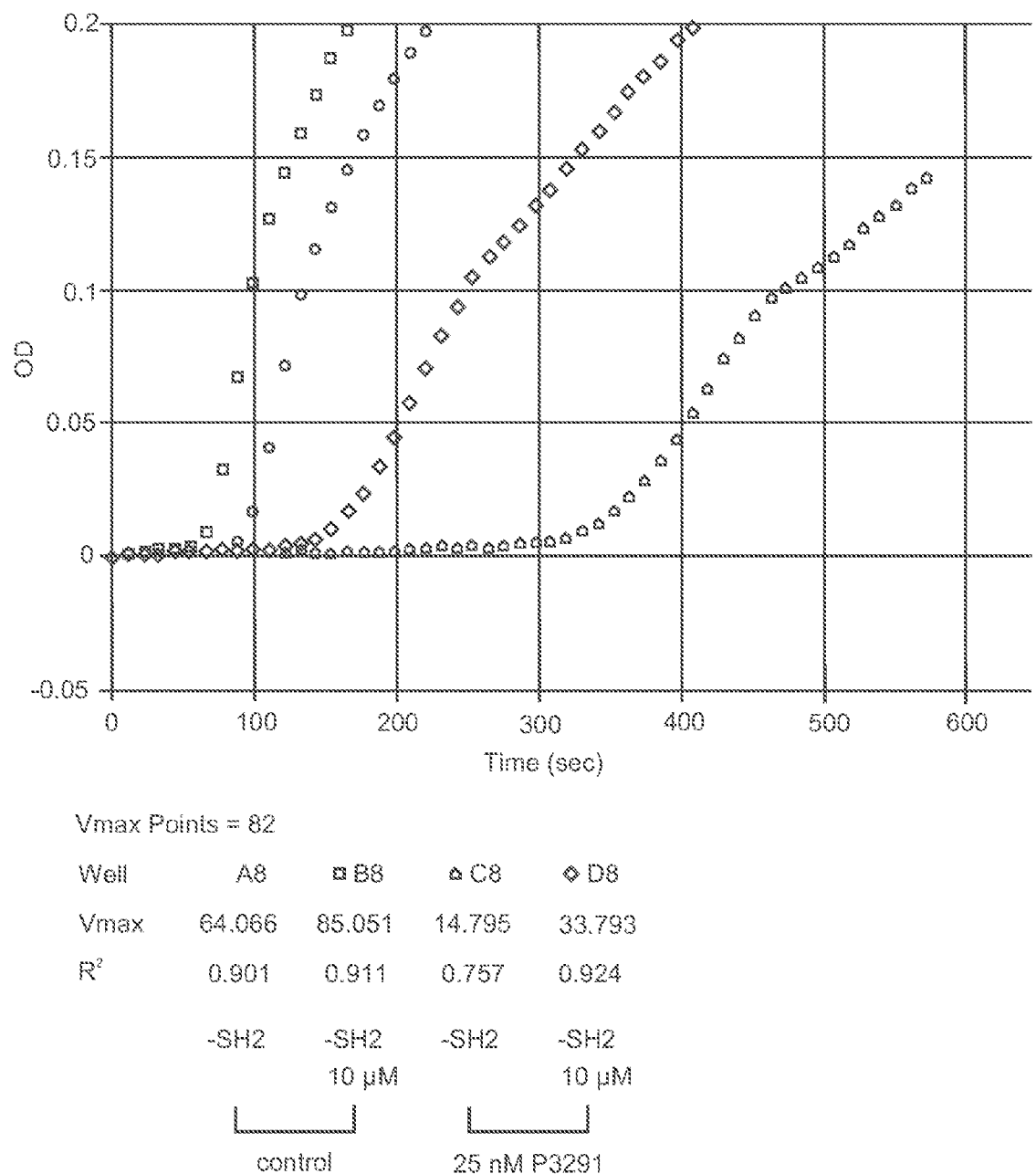

The SLAM sequence, i.e. the peptide of SEQ.ID.NO.28 can also be used as a linker moiety with a bivalent thrombin molecule. FIGS. 14C, 14D and 14E depict inhibition of fibrinogen clotting assays by the thrombin inhibitor Bbs-Arg-dPip-Gly-Arg-Lys-Ser-Leu-Thr-Ile-Tyr-Ala-Gln-Val-Gln-Lys-Gly-Asp-Phe-Glu-Glu-Ile-Pro-Glu-Glu-Tyr-Leu-Gln (SEQ. ID. NO. 102) in the presence and absence of an SH2 domain from the SAP protein (SAP-SH2). This thrombin inhibitor is designated as P3291. The curves represent $OD_{420}$ time course after the addition of 0.6 nM thrombin in the presence of (C) (○) 0 nM P3291; (□) 10 nM P3291; (Δ) 15 nM P3291; (◇) 20 nM P3291; (●) 30 nM P3291; (■) 40 nM P3291; (▲) 50 nM P3291; (◆) 60 nM P3291; (D) (○) 0 nM P3291, 10 µM SAP-SH2; (□) 0 nM P3291, 5 µM SAP-SH2; (Δ) 25 nM P3291, 0 µM SAP-SH2; (◇) 25 nM P3291, 5 µM SAP-SH2; (E) (○) 0 nM P3291, 0 µM SAP-SH2; (□) 0 nM P3291, 10 µM SAP-SH2; (Δ) 25 nM P3291, 0 µM SAP-SH2; (◇) 25 nM P3291, 10 µM SAP-SH2. Other experimental conditions were as used in assays described in FIG. 3.

Generally, linkers are elongate oligomeric or polymeric molecules adapted to permit strong covalent attachment or strong electrostatic binding of at least two moieties, wherein the moieties spaced apart along said linker. Linkers are preferably "modulatable linkers", in other words, linkers which undergo a change in flexibility and/or conformation in response to a defined environmental condition such as pH, temperature, proteolysis, chemical modification, magnetic field, local concentration of one or more molecules or complexes. Examples of temperature-sensitive linkers include polypeptides containing the elastin repeats (Urry, 1997, 11007-11028), specifically the $(VPGVG)_{19}$-VPGV (SEQ. ID. NO. 118) peptide which is producible by recombinant DNA methods (McPherson and others, 1992, 347-352). Other examples of peptide linkers responsive to protein binding including short linear peptide motifs known for cell compartment targeting, protein-protein interactions, and regulation by post-translation modifications (Puntervoll and others, 2003, 3625-3630; Diella and others, 2004, 79).

Introduction of a long oligomeric or polymeric linker between two binding heads may reduce the affinity beyond the point where the bivalent ligand is no longer switchable for a desired application. This is particularly true if one of the binding moieties is significantly weaker than the other, as is the case for the CaM-DTI and CaM-DTI2 proteins (FIG. 10) (see Table 2 for other examples). In addition, long oligomeric linkers are often more flexible, giving rise to significantly larger statistical distances spanning any given covalent spacing (Bright, Woolf and Hoh, 2001, 131-173). In this case the observed affinity is approximately equal to the monovalent affinity of the stronger binding moiety, in other words, the bivalent increase in affinity is lost. One can remedy this situation by optimizing the binding affinities of the individual heads through combinatorial library selection.

A strategy to improve the binding affinity of polypeptide ligands consisting of natural amino acids is to utilize phage display optimization. If one of the binding moieties is sufficiently strong, phage-displayed peptides need to be randomized only in the vicinity of the other binding moiety. The reappearing bivalency allows strong affinity of the ligand and the corresponding polypeptide sequences will be readily selected from a medium-sized phage library. Alternatively or additionally, NMR relaxation dispersion techniques can be used to identify an appropriate candidate from a fragment library for subsequent linkage to the other binding moiety. The advantage of this new NMR-based approach lies in its ability to provide both the molecular structure (identity) and ranking of the dissociation kinetics of hit fragments. Such an NMR-based screening can also be applied to molecules that are either natural polypeptides or other chemical entities available only through chemical synthesis.

In addition, if more than two distinct sites interacting with their specific ligands are known on a target surface, one can design an inhibitor containing more than two binding heads and link them with two or more controllable linkers, identical or different.

Production of polypeptides containing multiple binding moieties and controllable linkers can be achieved either through chemical peptide synthesis or using recombinant methods. Additional opportunities are provided by the possibilities to conjugate peptide fragments using thiol, primary amine or carboxyl chemistries. In light of the disclosure herein, one skilled in the art could readily produce such polypeptides. For example, thiol chemistry is particularly effective for coupling oligonucleotides to peptides (Lin and others, 1995, 11044-11048) in the fabrication of biomolecular devices containing oligonucleotides as linkers (FIG. 16C).

Molecular species and methods of the invention can be used in a number of screening methods. In some instances the recorded compound ("readout") is preferably chromogenic or fluorogenic. For example, some commercially available substrates for thrombin are based on p-nitroaniline (chromogenic) or on 6-amino-1-naphthalenesulfonamide (fluorogenic). The presence of an inhibitor impedes development of color or fluorescence in an assay that can be readily performed in a 96-well plate and recorded by a plate-reader. If the inhibitor contains a linker sensitive to a certain type of specific peptide-protein molecular interaction, the presence of linker-binding protein can be identified in a 96-well plate format. Alternatively, the same 96-well plate format can be used for the identification of an enzymatic activity (e.g. performed by such enzymes as phosphatases or kinases) changing the ability of the linker to bind a known protein or altering flexibility of the linker. In this regard, binding or enzymatic activities are converted and recorded in the activities or changes in the activities of the target protein (e.g. thrombin). As such, it will be complementary to fluorescence-based methods (UK patent Application, GB 2375538) that have limitations in dynamic-range imposed by specific conformational changes (Truong and others, 2001, 1069-1073).

FIG. 15 depicts the concept of covalent conjugations between tweezer-like polypeptides and the binding proteins. FIG. 15A is a model for a conjugated complex of CaCdc42 and an eCRIB via a polymeric linker. FIG. 15B depicts resonance assignment of the $^1H$-$^{15}N$ HSQC spectra for *Candida* Cla4-eCRIB in a conjugated complex with CaCdc42. The resonance peaks have the same pattern as those in the non-covalent complex. However, the conjugated complex is significantly more stable (>3 months) than the non-covalent one (<one week). FIG. 15C shows the $^1H$-$^{15}N$ HSQC spectrum for *Candida* Cst20-eCRIB in a conjugated complex with CaCdc42. FIG. 15D shows the potential application of a stable conjugated complex for discovering stronger and specific binders. The dissociation of the tethered bivalent polypeptide can be detected by use of NMR relaxation and H/D exchange experiments using the assigned H-$^{15}$N HSQC spectrum of the conjugated protein (see FIGS. 15B and 15C).

Certain polypeptides are known to undergo folding or unfolding transitions upon changes of pH, ionic strength or temperature. Inhibitors incorporating these flexible peptides as linkers will be affected in their potency by the corresponding environmental changes. In an embodiment of the invention, the controllable linker is a well-folded and structured biomolecule, whose rigid three-dimensional structure prevents the binding of the bivalent ligand in the high-affinity mode. Defined three-dimensional structure of the biomolecule can be denatured by a variety of environmental effects such as changes in pH, temperature, proteolysis, chemical modifications and localized electromagnetic irradiation. Such a denaturation will render the linker moiety flexible, thereby providing the linker moiety with suitable physicochemical properties for bivalent ligand binding to its target.

Bivalent polypeptides at the generic level are responsive to signals that modulate the physicochemical properties of the linker moiety (FIG. 1). When the linker is responsive to binding, e.g. of a protein or of an oligonucleotide, or other biomolecules, the active concentration of the linker binding molecule can generally be reduced through denaturation, e.g. by use of radio-wave (or radio-frequency magnetic field, RFMF) induced biomolecular heating (Hamad-Schifferli and others, 2002, 152-155). Such a reduction in concentration of the activity-reversing protein will be accompanied by the reactivation of the inhibited target protein, a phenomenon governed by thermodynamic principles (FIG. 1B).

Figure 16:
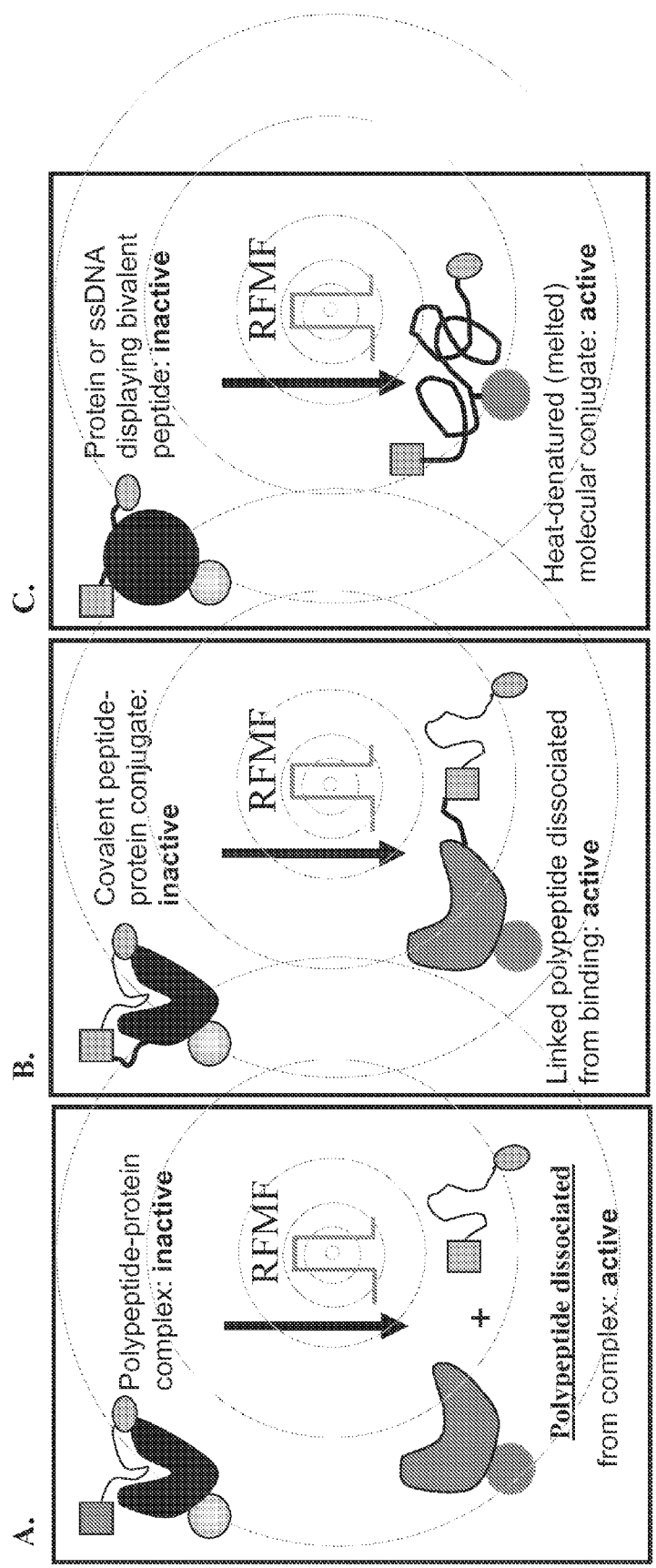

FIG. 16 depicts three scenarios by which the bivalent polypeptides can be used to fabricate biomolecular devices sensitive to electromagnetic irradiation. FIG. 16A shows a generally inactive complex produced by the binding of the linker moiety of a bivalent peptide to a linker-specific protein. The linker-binding protein is in addition conjugated to a heat-transducing nanoparticle, which in the illustrated case is a gold nanoparticle as described previously (Hamad-Schifferli and others, 2002, 152-155). Upon electromagnetic (RF fields) irradiation, the linker-binding (antidote) protein will be denatured upon heating, leading to release and activation of the bivalent polypeptide. FIG. 16B depicts the construction of a covalent conjugate of the bivalent polypeptide with a heat-transducing antidote protein. The bivalent polypeptide is more efficiently inactivated in a covalent conjugate as a result of intramolecular effects. RF irradiation will lead to local release of the bivalent peptide, in a way suitable for target binding through bivalent interactions (FIG. 1). FIG. 16C depicts an extension of the fabrication procedure illustrated in FIG. 16B. In this scenario, the linker moiety itself confers the antidote effect, in that the linker can fold into a defined three-dimensional structure with geometry not suitable for bivalent binding of the attached monovalent ligands. Presence of RF fields will denature the structure of the linker moiety, thereby creating a polymeric linker conformation suitable for bivalency effects. In this regard, the CaM-DTI proteins (FIG. 9) can be attached to a gold nanoparticle or a magnetic nanoparticle (MNPs) and RF irradiation is expected to enhance thrombin inhibitory activity of a MNP-conjugated CaM-DTI protein.

In an embodiment of the invention, the linker moiety is an oligonucleotide, to which is attached covalently two weak-binding monovalent ligands. The oligonucleotide linker is in addition labeled by a gold or magnetic nanoparticle for inductive coupling to and activation by an external field. Specifically, Bbs-Arg-(dPip)-Gly-Cys i(SEQ.ID.NO.15) is to be coupled using thiol chemistry to the 3' or 5' end of a single-stranded DNA (e.g. the DNA-I molecule or 5'-TAGC-GATACTGCGTGGGTTGGGGCGGG-TAGGGCCAGCAGTCTCGT-3' of Lin et al and Jayasena (Lin and others, 1995, 11044-11048) or 5'-GCGCCCTAAACTGGTGGT*GGAATGCGTCATG AGGGCGC-3' of Hamad-Schifferl et al and Jacobson (Hamad-Schifferli and others, 2002, 152-155). The other end of the DNA molecule will be attached covalently with a peptide containing the sequence Asp-Phe-Glu-Gly-Ile-Pro-Glu-Glu-Tyr-Gln. Denaturation of the single-stranded DNA hairpin should activate the bivalent functionality of the attached peptides for high-affinity thrombin inhibition in the presence of an RF magnetic field (FIG. 16C).

In some cases molecular species and methods of the invention can be used to specifically dissect, interrupt or initiate biological pathways. One can design a bivalent ligand with a trigger to release its target at a certain location and/or at a specific time. The ligand/target pair can be delivered together or separately using known methods of extra or intracellular delivery including protein expression from an oligonucleotide template. Alternatively, the target can occur naturally, outside or inside the cell, e.g. the GTPase of the Rho-family, Cdc42 (FIG. 15). The triggering molecular device can be a delivered molecule or a naturally occurring molecule. The triggering molecular device can be a molecular process (for example, catalytic phosphorylation, dephosphorylation, or specific proteolysis). The triggering molecular device can be localized and/or produced and initiated at a certain time point. For example, a bivalent CRIB-based ligand of Cdc42 can be delivered into the cell to arrest the action of membrane-anchored Cdc42 (FIG. 15). The inhibitory action of intracellularly-delivered and membrane-localized CRIB peptides can be reversed by the binding of the linker portion (i.e. the SLAM segment of eCla4-SLAM in FIG. 11 and Table 2) to an SH2 domain. The affinity of the SH2-linker interaction is relatively weak, with a thermodynamic dissociation constant in the micromolar range (~1 µM, see FIGS. 14A and 14B). Therefore, the SH2 domain (i.e. the antidote) is to be conjugated to the surface a nanoparticle for affinity enhancement through multivalent presentation. Vice versa, the complexes of the CRIB peptides with the SH2 molecules conjugated to metal or magnetic nanoparticles (MNPs) can be disrupted by radio-wave induced heating of MNPs, as reported previously (Jordan and others, 1999, 413-419; Hamad-Schifferli and others, 2002, 152-155; also see FIG. 16).

Figure 17:
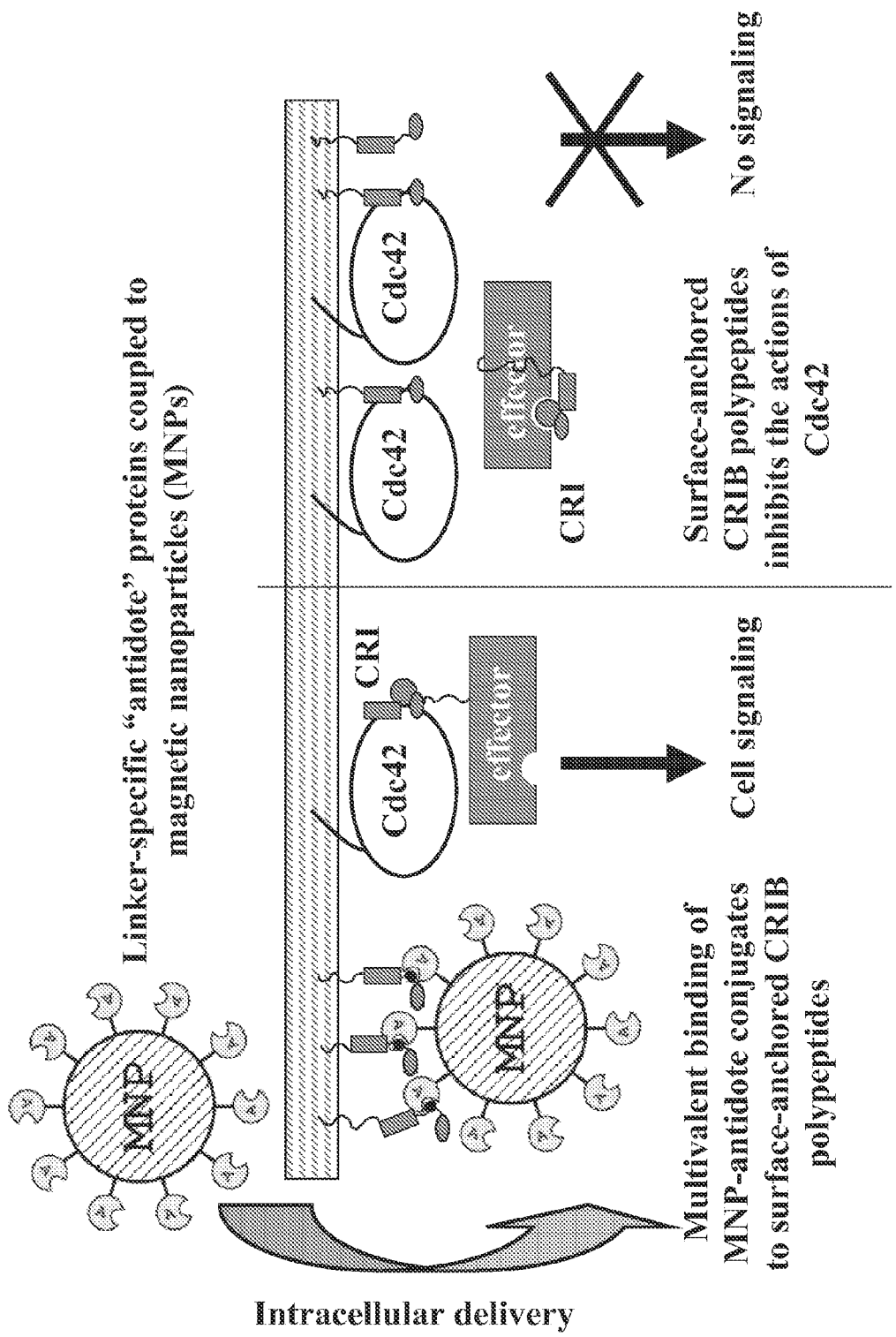

FIG. 17 depicts schematically the use of a bivalent polypeptide with a controllable polymeric linker in the examination of cell-signaling pathways. In the embodiment of FIG. 17, a bivalent CRIB polypeptide is to be delivered into the cytoplasmic space of a cell, specifically for associations with the cytoplasmic face of the cell membrane. As such, the CRIB peptide (e.g. the eCla4 peptide containing the -Arg-Lys-Ser-Leu-Thr-Ile-Tyr-Ala-Gln-Val-Gln-Lys-sequence (SEQ. ID. NO. 28), or eCla4-SLAM (FIG. 11 and Table 2) will inhibit the membrane-anchored Cdc42 for its interactions with downstream effector proteins. This inhibitory action can be reversed by the delivery of an SH2 domain (i.e. the antidote or "A") with specific binding to the linker portion. For affinity enhancement, the SH2 domain antidote can be conjugated to the surface of a nanoparticle for multivalent presentation. A metal or magnetic nanoparticle (MNPs) is used here since these nanoparticles can transduce radio-frequency waves into heat (for both metal and magnetic nanoparticles, see also FIG. 16) or can be used as contrast agents (magnetic nanoparticles) in magnetic resonance imaging (MRI) applications.

In light of the disclosures provided herein, it should be apparent to ones skilled in the art that Cdc42 inhibition can be achieved by any number of suitable polypeptides (see for example Pirone, Carter and Burbelo, Trends in Genetics 17, 370-373, 2001) containing sequences homologous to the extended CRIB sequences derived from *Candida albicans* Cla4 and Cst20 proteins (FIG. 11). In these applications, monovalent CRIB fragments will be identified following the same procedures as used for *Candida* proteins (FIGS. 11-13). Such peptide fragments will then be reassembled into bivalent polypeptides, containing as linkers either the SLAM sequence (SEQ.ID.NO.28) or other linear peptide motifs (Puntervoll and others, 2003, 3625-3630; Diella and others, 2004, 79) depending on the applications. Furthermore, all the bivalent peptides including eCla4-SLAM (FIG. 11 and Table 2) are preferably prepared in palmitoylated forms, which enable intracellular delivery and localization to the cytoplasmic face of the cell membrane (Covic et al, and Kuliopulos, Proc. Natl. Acad. Sci. 99, 643, 2002).

Molecular species and methods of the invention can also be used to design new molecules for pharmaceutical intervention. Medical intervention in case of an injury to an internal organ requires a strategy to seal the wound. Fibrin sealant is found to be effective and can be used safely on vital organs. It is thus widely used as a bioactive hemostat in cases of both superficial and internal injury. The formulation that is commercially available (e.g. Tisseel VH Fibrin Sealant, Baxter) consists of two components: thrombin and fibrinogen. When both components are reconstituted and mixed thrombin catalyses the conversion of fibrinogen to fibrin, which in turn forms a fibrin scaffold or sealant. One of the limitations of the present formulation is that once reconstituted, thrombin proteolytically degrades itself. In light of the disclosure herein there is provided a new formulation, wherein the proteolytic activity of thrombin is inhibited by a stimuli-responsive bivalent inhibitor e.g. Bbs-Arg-(D-Pip)-Gly-(Ser-Pro-His-Tyr(P)-Glu-Lys-Val-Ser-Gly)n-Asp-Phe-Glu-Glu-Ile-Pro-Glu-Glu-Tyr-Leu-Gln (P3170) (SEQ. ID. NO. 29) with a controllable polymeric linker binding to an SH2 domain (FIG. 4). In the new formulation of fibrin glue, thrombin and inhibitor can be premixed and will stay substantially inactive (and stable) for a reasonable period of time until exposed to SH2.

The middle auricular artery of eight rabbits was cut transversely with a scalpel. Two rabbits were left untreated to measure the bleeding time. The Tisseel fibrin glue (one fresh sample, one incubated overnight at 37° C.) was applied to the wound of two other rabbits. The fibrin glue containing inhibitor-stabilized thrombin component, "Thrombin 4", was applied to another pair of rabbits immediately after activation with SH2. SH2-activated fibrin glue with the P3170 inhibitor was able to seal the wound at around ~5 minutes (FIG. 18).

Looking at FIG. 18, the top panel shows arterial bleeding from a rabbit ear 5 minutes after the transversal cut was made. Left bottom panel shows an arrest of the bleeding 1'47" after a commercial Tisseel preparation was applied to the fresh cut according to the manufacturer's procedure. Right bottom panel shows an arrest of bleeding 5 minutes after an inhibited and reactivated commercial Tisseel preparation was applied to the fresh cut according to the manufacturer's instructions. Thrombin inhibition was achieved by the addition of 8 nM of P3170 to the reconstituted "Thrombin 4" component of the Tisseel product. Thrombin activation was achieved by the inclusion of concentrated SH2 solution in the fibrinogen component of Tisseel to a final concentration of 12 µM.

In light of the disclosures provided herein, it will be apparent to one skilled in the art that other forms of fibrin sealants can be formulated. In particular, bivalent thrombin inhibitors with $Ca^{++}$-sensitive linkers can be used to inactivate (and stabilize) thrombin. The inactivated thrombin can in turn be reactivated upon contact with the bleeding wounds, wherein the fresh blood contains $Ca^{++}$ ions in millimolar concentrations. As well, the SH2-binding linker can be replaced by linker peptides with specific binding to other components of the blood, e.g. to integrin receptors on platelet surfaces (i.e. peptides P3234 and P3238 of Table 1, or SEQ. ID. NO. 88 and SEQ. ID. NO. 90), to fibrinogen itself (i.e. peptide P3236, Table 1 or SEQ. ID. NO. 89), to prothrombin (see the next section) and even to human serum albumin. One peptide sequence to use for the latter can be Leu-Ile-Glu-Asp-Ile-Cys-Leu-Pro-Arg-Trp-Gly-Cys-Leu-Trp-Glu-Asp (SEQ. ID. NO. 111), which is derived from panning a phage library against human serum albumin (Dennis and others, 2002, 35035-35043). One bivalent thrombin inhibitor containing an albumin-binding linker will have the sequence of Bbs-Arg-(D-Pip)-Gly-Leu-Ile-Glu-Asp-Ile-Cys-Leu-Pro-Arg-Trp-Gly-Cys-Leu-Trp-Glu-Asp-Gly-Asp-Phe-Gln-Gln-Ile-Pro-Glu-Glu-Tyr-Leu-Gln (SEQ. ID. NO. 112). One can envision a bivalent thrombin inhibitor of the formula Bbs-Arg-dPip-Gly-(Val-Pro-Gly-Val-Gly)$_{20}$-Asp-Phe-Glu-Glu-Ile-Pro-Glu-Glu-Tyr-Leu-Gln, (SEQ. ID. NO. 119) containing as linker a temperature responsive elastin-repeat peptide Gly-(Val-Pro-Gly-Val-Gly)$_{19}$-Val-Pro-Gly-Val (SEQ. ID. NO. 120) (McPherson and others, 1992, 347-352). An analogue of this peptide suitable for recombinant production will have the formula of Ile-Arg-Phe-Thr-Asp-Gly-Glu-Gly-(Val-Pro-Gly-Val-Gly)$_{20}$-Asp-Phe-Glu-Glu-Ile-Pro-Glu-Glu-Leu-Gln (SEQ. ID. NO. 121) with the Bbs-Arg-dPip-Gly (SEQ. ID. NO. 122) moiety replaced by Ile-Arg-Phe-Thr-Asp-Gly-Glu-Gly (SEQ. ID. NO. 116) for binding to the thrombin active site. Other thrombin inhibitors can also be constructed that contain as linkers with specific binding to other bloodborne proteins. For example, these peptide sequences and binding proteins can be selected from the database of linear peptide motifs as published previously (Puntervoll and others, 2003, 3625-3630). The different means of thrombin inhibition and re-activation can be combined to address specific requirements for the properties of new fibrin sealants.

In another case bivalent thrombin inhibitors were generated, which can bind to (and be neutralized by) prothrombin. One clinical application of such inhibitors is in the formulation of new fibrin sealants using inactivated thrombin that can be reactivated by prothrombin (vide supra). Another clinical application of this type of inhibitors is to display potency of thrombin inhibition only at a location with low prothrombin concentration due to its binding to prothrombinase and rapid turnover into thrombin (e.g. localized to the site of an atherosclerotic plaque). C-termini of the inhibitors contain hirudin residues 55-65, a fragment known to bind proexosite I of prothrombin with low affinity (Ni, F., Ning, Q., Jackson, C. M., and Fenton, J. W., 1993, 16899-16902; Anderson, P. J.; Nesset, A.; Dharmawardana, K. R.; and Bock, P. E., 2000, 16428-16434; Tolkatchev, Xu and Ni, 2003, JACS 12432-12442). A linker is engineered to provide additional contacts with prothrombin and confer much stronger specific affinity of the inhibitor to prothrombin. A phage-displayed peptide library was designed and constructed (preparation of the library is described in Su, Z.; Vinogradova, A.; Koutychenko, A.; Tolkatchev, D.; and Ni, F., 2004a, 647-657). The library was panned against prothrombin immobilized on the bottom of a MaxiSorp plate well. Panning enhanced growth of two phage species containing displayed sequences Gly-Ser-Val-Val-Pro-Arg-Pro-Gln-Leu-His-Asn-Asp-Gly-Asp-Phe-Glu-Glu-Ile-Pro-Glu-Glu-Tyr-Leu-Gln (SEQ. ID. NO. 30) and Gly-Ser-His-Ala-Pro-Arg-Pro-Gln-Ile-His-Asn-Asp-Gly-Asp-Phe-Glu-Glu-Ile-Pro-Glu-Glu-Tyr-Leu-Gln (SEQ. ID. NO. 31). Discovered sequences were used to construct two bivalent thrombin inhibitors, Bbs-Arg-(D-Pip)-Gly-Ser-Val-Val-Pro-Arg-Pro-Gln-Leu-His-Asn-Asp-Gly-Asp-Phe-Glu-Glu-Ile-Pro-Glu-Glu-Tyr-Leu-Gln (SEQ. ID. NO. 32) and Bbs-Arg-(D-Pip)-Gly-Ser-His-Ala-Pro-Arg-Pro-Gln-Ile-His-Asn-Asp-Gly-Asp-Phe-Glu-Glu-Ile-Pro-Glu-Glu-Tyr-Leu-Gln (SEQ. ID. NO. 33). Measured $IC_{50}$ were 1.1 and 0.6 nM, respectively, indicating the bivalent nature of inhibitor interaction with thrombin was retained (FIG. 2, Table 1). Further improvement of the linker includes panning against phage-displayed peptide library with four randomized residues in the sequence Gly-Ser-Val-Val-Pro-Asn-Xxx-Xxx-Leu-Xxx-Xxx-Asp-Gly-Asp-Phe-Glu-Glu-Ee-Pro-Glu-Glu-Tyr-Leu-Gln (SEQ. ID. NO. 34). Specifically, bio-panning of new phage libraries against prothrombin will expand the sequence hits from the two sequences shown (i.e. SEQ. ID. NO. 30 and SEQ. ID. NO. 31), leading to bivalent peptides with adequate binding affinities to prothrombin. These new prothrombin-binding polypeptides are conjugated through their N-termini to the Bbs-Arg-(D-Pip) (SEQ. ID. NO. 68) moiety to create high-affinity bivalent inhibitors of thrombin, as demonstrated with peptides Bbs-Arg-(D-Pip)-Gly-Ser-Val-Val-Pro-Arg-Pro-Gln-Leu-His-Asn-Asp-Gly-Asp-Phe-Glu-Glu-Ile-Pro-Glu-Glu-Tyr-Leu-Gln (SEQ. ID. NO. 32) and Bbs-Arg-(D-Pip)-Gly-Ser-His-Ala-Pro-Arg-Pro-Gln-Ile-His-Asn-Asp-Gly-Asp-Phe-Glu-Glu-Ile-Pro-Glu-Glu-Tyr-Leu-Gln (SEQ. ID. NO. 33). Ultimately, a dual-affinity polypeptide is to be selected from this process. In other words, one can generate polypeptides with high-affinity bivalent binding of and inhibition against thrombin and at the same time with suitable binding affinities to prothrombin and whose thrombin-binding potency can be neutralized by circulating concentrations of prothrombin (in the range of a few micromolar in normal plasma).

In an embodiment of the invention, there is provided a method for the purification of a target protein, e.g. thrombin, prothrombin, Cdc42, or any other protein for which a bivalent and retractable polypeptide ligand is designed. The bivalent polypeptide will be immobilized on a solid support for use as an affinity absorbent for the targeted protein. The absorbed protein can be eluted using molecular agents or temperature, which upon contact with the affinity matrix will inactivate the bivalent ligand and release the absorbed protein. In light of the disclosures provided here in, it will be apparent to ones skilled in the art what detailed procedures will need to be followed for the above-mentioned applications.

SPECIFIC EXAMPLES

Example 1

A tolerance of the bivalent mode of inhibition to the amino acid composition of the linker moeity on a series of bivalent inhibitors of thrombin with an active site binding moiety Bbs-Arg-(D-Pip)-Gly (H1, Bbs=4-tert-butyl-benzenesulfonyl, D-Pip=D-pipecolic acid, $K_I$ in low μM range (SEQ. ID. NO. 35) (Slon-Usakiewicz and others, 2000, 2384-2391) and an exosite 1 binding moiety Gly-Asp-Phe-Glu-Glu-Ile-Pro-Glu-Glu-Tyr-Leu-Gln ((SEQ. ID. NO. 36), H2, $K_I$ in low μM range) derived from the C-terminal tail of hirudin was demonstrated. The peptides were synthesized using standard Fmoc chemistry. Crude peptides were purified by HPLC using a reversed-phase $C_{18}$ Vydac column and a linear 10-45% or 20-45% acetonitrile gradient in 0.1% trifluoroacetic acid (TFA). Peptides were freeze-dried and their identity was confirmed by ion-spray mass spectrometry. Clotting assays were carried out by use of the protocols described previously (DiMaio and others, 1990, 21698-21703; Witting and others, 1992, 737-743). The assay employs bovine plasma fibrinogen dissolved at 0.1% in 50 mM Tris-Cl, 100 mM NaCl, 0.1% PEG-8000 at pH 7.6 (i.e. the clotting buffer). Each assay mixture contained a certain concentration of the peptide, and the reaction was started by the addition of human thrombin to a final concentration of 0.6-1.2 nM. Optical absorbance increase at 420 nm caused by fibrin clot formation was measured at 25° C. or 37° C. using the Spectramax plate reader. The onset clotting time was determined as an intersection of the baseline and the extrapolated linear portion of the OD change curve. The concentration of a peptide needed to double the clotting time was defined as $IC_{50}$ (DiMaio and others, 1990, 21698-21703). Kinetic amidolytic curves were obtained in clotting buffer at 25° C. using eight inhibitor concentrations and three to five concentrations of the chromogenic substrate S-2238 (Chromogenix) (DiMaio and others, 1990, 21698-21703). Inhibition constants were extracted from Lineweaver-Burk equation by using weighted linear regression. Errors in $K_i$ determination were estimated by using Monte-Carlo sampling with 1-3% variance of the experimental points. Peptide concentrations were determined spectrophotometrically using predicted extinction coefficients at 278 nm (Gill and von Hippel, 1989, 319-326).

With a wide range of linker lengths and compositions $IC_{50}$ of the bivalent inhibitors in a fibrinogen clotting assay remained in low-nanomolar range (Table 1, and FIG. 2), values sufficiently low for peptide-based antithrombotic pharmaceutical compounds (Witting and others, 1992, 737-743), and much lower than the $K_I$ values of the constituent binding moieties (Slon-Usakiewicz and others, 2000, 2384-2391). In every case an improvement in $IC_{50}$ as compared with that of the H2 moiety confirmed the bivalent mode of the polypeptide-thrombin interaction. The C-terminal portion of the peptide consisting of only natural amino acids and including the polymeric linker plus the H2 moiety ((Gly-Ser)n-Gly-Asp-Phe-Glu-Glu-Ile-Pro-Glu-Glu-Tyr-Leu-Gln) (SEQ. ID. NO, 113) can be produced using recombinant methods. Linking of the H1, containing unnatural amino acids, with the rest of the peptide can be performed using standard coupling techniques. We synthesized and purified peptides with amino acid sequences Bbs-Arg-(D-Pip)-Gly-Cys (SEQ. ID. NO. 4) and Cys-(Gly-Ser)$_8$-Gly-Asp-Phe-Glu-Glu-Ile-Pro-Glu-Glu-Tyr-Leu-Gln (SEQ. ID. NO. 5). They were linked together by thiol oxidation in 2% ammonium acetate buffer, pH 8.6, over a period of 2 days. Resulting products were separated by reversed-phase HPLC and their identity was established by ion-spray mass spectroscopy. A product of disulfide bond linkage between peptides Bbs-Arg-(D-Pip)-Gly-Cys (SEQ. ID. NO. 4) and Cys-(Gly-Ser)$_8$-Gly-Asp-Phe-Glu-Glu-Ile-Pro-Glu-Glu-Tyr-Leu-Gln (SEQ. ID. NO. 5) (corresponding to SEQ. ID. NO. 83) was tested for $IC_{50}$ in the clotting assay. We established that the two-chain peptide was potent and therefore bivalent with an $IC_{50}$ of 1.1±0.2 nM (FIG. 2). Another disulfide-linked bivalent thrombin inhibitor (corresponding to SEQ. ID. NO. 91) was prepared in the same fashion from two peptides Bbs-Arg-(D-Pip)-Gly-Cys (SEQ. ID. NO. 4) an d Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ. ID. NO. 114).

Example 2

We made use of an amino acid sequence Cys-Pro-His-Tyr-Glu-Lys-Val-Ser-Gly (SEQ. ID. NO. 8) derived from the cytoplasmic tail of the cell-surface anchored ligand ephrin B2 (ephrinB2$_{301-309}$) to link the H1 and H2 moeities. The peptide is known to be flexible and in its tyrosine-phosphorylated state to bind SH2 domain from Grb4 with an affinity of 0.2 µM (Su, Xu, and Ni, 2004b, 1725-1736). We produced four peptides of a general formula Bbs-R-(D-Pip)-Gly-(Ser-Pro-His-B-Glu-Lys-Val-Ser-Gly)n-Asp-Phe-Glu-Glu-Ile-Pro-Glu-Glu-Tyr-Leu-Gln (SEQ. ID. NO. 9), wherein B was either tyrosine (Tyr) or phosphotyrosine (Tyr(P)), and n was 1 or 2. The peptides were synthesized and their identity confirmed as outlined in Example 1. $IC_{50}$ of the inhibitors in the thrombin-clotting assay were comparable and in the vicinity of 0.5-1 nM, except for the peptide with two phosphotyrosines whose $IC_{50}$ was 18-20 nM (Table 2, FIG. 3). Incorporation of two phosphotyrosines in the linker resulted in a significant drop in the inhibition potency. Given the fact that the potency of the bivalent inhibitor Bbs-R-(D-Pip)-Gly-(Ser-Pro-His-B-Glu-Lys-Val-Ser-Gly)$_2$-Asp-Phe-Glu-Glu-Ile-Pro-Glu-Glu-Tyr-Leu-Gln (SEQ. ID. NO. 115) depends on the phosphorylation state of the linker, a coupling with enzymatic assay translating activity of kinase or phosphatase into serine protease activity such as that of thrombin can be developed.

Example 3

An alternative way to reverse the inhibitory potency of the peptides with a general formula Bbs-R-(D-Pip)-Gly-(Ser-Pro-His-B-Glu-Lys-Val-Ser-Gly)n-Asp-Phe-Glu-Glu-Ile-Pro-Glu-Glu-Tyr-Leu-Gln (SEQ. ID. NO. 9), wherein B was either tyrosine (Tyr) or phosphotyrosine (Tyr(P)), and n was 1 or 2, is to bring them in contact with SH2 domain in solution. SH2 domain of Grb4 was prepared as follows. The DNA sequences encoding the Grb4 SH2 domain was deduced from the amino acid sequences of murine Grb4 protein using the codon preference of *Escherichia coli*. The synthetic gene was amplified by PCR from six pairs of overlapping synthetic primers containing the two restriction sites of NcoI and BamHI for the SH2 domain at its two ends. The double-digested DNA fragment of SH2 was subcloned into the pET3215 expression vector, which was modified from pET32 and pET15 vectors (Novagen, Madison, Wis., USA), removing the original fusion carrier in the pET32 vector. In order to facilitate protein purification, a His-tag with six histidine residues was placed at the N-terminus of the SH2 domain linked with a thrombin cleavage sequence. The expression construct was confirmed by DNA sequencing and transformed into the *E. coli* BL21(DE3) expression host. The SH2 protein was expressed at 37° C. The cells were harvested four hours after induction with isopropyl thio-β-D-galactoside at $OD_{600}$=0.8. Protein purification was performed under denaturing conditions with Ni-nitriloacetic acid agarose beads (Qiagen) in the presence of 20 mM 2-mercaptoethanol at pH values of 8.0, 6.3, 5.9 and 4.5 for the binding, two washing, and eluting steps, respectively. Protein fractions were analyzed using SDS PAGE. Fractions containing SH2 domain were collected and refolded by dialyzing 2 3 times against a large volume of 50 mM sodium phosphate buffer containing 20 mM 2-mercaptoethanol (pH 6.8) at 4° C. The pellet was removed by centrifugation and the supernatant was concentrated by ultrafiltration (Millipore, Bedford, Mass., USA). Protein concentration was determined spectrophotometrically at 280 nm with a calculated extinction coefficient of 12210 $M^{-1}cm^{-1}$.

Influence of SH2 on inhibitory potency of the four peptides was tested in the clotting assay. Clotting time in the presence or absence of each of the inhibitors, presence and absence of 3 μM SH2 (inhibitor antidote), and equal amount of thrombin (0.6 nM) was measured at 22° C. The peptide Bbs-R-(D-Pip)-Gly-(Ser-Pro-His-Tyr-Glu-Lys-Val-Ser-Gly)-Asp-Phe-Glu-Glu-Ile-Pro-Glu-Glu-Tyr-Leu-Gln (SEQ. ID. NO. 80) was used at a concentration of 1 nM, the peptide Bbs-R-(D-Pip)-Gly-(Ser-Pro-His-Tyr(P)-Glu-Lys-Val-Ser-Gly)-Asp-Phe-Glu-Glu-Ile-Pro-Glu-Glu-Tyr-Leu-Gln (SEQ. ID. NO. 82) was used at a concentration of 4 nM, the peptide Bbs-R-(D-Pip)-Gly-(Ser-Pro-His-Tyr-Glu-Lys-Val-Ser-Gly)$_2$-Asp-Phe-Glu-Glu-Ile-Pro-Glu-Glu-Tyr-Leu-Gln (SEQ. ID. NO. 81) was used at a concentration of 2 nM, and the peptide Bbs-R-(D-Pip)-Gly-(Ser-Pro-His-Tyr(P)-Glu-Lys-Val-Ser-Gly)$_2$-Asp-Phe-Glu-Glu-Ile-Pro-Glu-Glu-Tyr-Leu-Gln (SEQ. ID. NO. 14) was used at a concentration of 50 nM. Interaction of the SH2 domain with phosphotyrosine-containing inhibitors reversed the inhibitory potency of the Bbs-R-(D-Pip)-Gly-(Ser-Pro-His-Tyr(P)-Glu-Lys-Val-Ser-Gly)n-Asp-Phe-Glu-Glu-Ile-Pro-Glu-Glu-Tyr-Leu-Gln (SEQ. ID. NO. 29) (n=1,2) peptides, but not that of Bbs-K-(D-Pip)-Gly-(Ser-Pro-His-Tyr-Glu-Lys-Val-Ser-Gly)n-Asp-Phe-Glu-Glu-Ile-Pro-Glu-Glu-Tyr-Leu-Gln (SEQ. ID. NO. 11) (n=1,2) peptides (FIG. 4). The change in thrombin activity upon binding of SH2 is a basis for developing an assay for protein-to-peptide binding, which can be realized in a high-throughput manner.

A linker known to bind to a specific antibody may be used to perform as a switchable polymeric linker if the antibody is introduced into the activity assay. A peptide with a formula Bbs-R-(D-Pip)-Gly-Glu-Gln-Lys-Leu-Ile-Ser-Glu-Glu-Asp-Leu-Gly-Asp-Phe-Glu-Glu-Ile-Pro-Glu-Glu-Tyr-Leu-Gln (SEQ. ID. NO. 13) was prepared and tested for its ability to inhibit thrombin and be neutralized by a commercially available anti-c-myc antibody, known to bind to the peptide with a sequence Glu-Gln-Lys-Leu-Ile-Ser-Glu-Glu-Asp-Leu (SEQ. ID. NO. 12). The peptide was present in the clotting assay at a concentration of 150 nM, and thrombin—at a concentration of 0.6 nM. In the absence of the neutralizing antibody clotting onset time was delayed from approximately 100 s to approximately 530 s (FIG. 5). Addition of anti-c-myc antibody 9E10 (Sigma) in the stock buffer provided by the supplier to the final concentration of 1.2 μM reversed the inhibitory effect of the inhibitor to the clotting onset time of approximately 230 s. The effect of the control on thrombin activity in the absence of the inhibitor was very small (FIG. 5).

Example 4

An inhibitor with a linker known to bind specific metal ions will be affected by the presence of these ions in solution. Two peptides homologous to the calcium-binding loop of troponin C were designed and established that they bind calcium ions in solution. The peptides have the following sequences—Ac-Asp-Lys-Asn-Ala-Asp-Gly-Trp-Ile-Asp-Asn-Gly-Glu-Phe-Glu-$NH_2$ (P3230) (SEQ. ID. NO. 109) and Ac-Asp-Lys-Asn-Ala-Asp-Gly-Trp-Ile-Asp-Asn-Gly-Asp-Phe-Glu-$NH_2$ (P3231) (SEQ. ID. NO. 110). The peptides were synthesized, purified and their identity was confirmed as described in Example 1. They were tested for calcium binding by use of NMR. For this both freeze-dried peptides were reconstituted at a concentration of approximately 0.5 mM in 20 mM sodium acetate-$d_3$ buffer, pH 5.5, containing 10% $D_2O$. Proton spectra of the peptides were recorded at 800 MHz, 15° C., before and after addition of increasing amounts of 0.1 and 1 M stock solutions of $CaCl_2$ in the same buffer. FIGS. **6*a,b,c,d*** show changes in the proton NMR spectra of these two peptides upon the addition to the initial volume of ~450 μL of 1

μL (final CaCl$_2$ concentration ~0.22 mM), additional 2 μL (final CaCl$_2$ concentration ~0.66 mM), additional 10 μL (final CaCl$_2$ concentration ~2.8 mM) of 100 mM CaCl$_2$, and additional 10 μL (final CaCl$_2$ concentration ~23.9 mM) of 1 M CaCl$_2$. The changes in the spectra confirm binding of calcium with affinity in mM range.

One of the two designed peptides was used to construct a calcium-responsive bivalent thrombin inhibitor. The disulfide-linked bivalent thrombin inhibitor (corresponding to SEQ. ID. NO. 91) prepared by cross-oxidation of cysteine thiol groups from two peptides Bbs-Arg-(D-Pip)-Gly-Cys (SEQ. ID. NO. 4) and Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln (SEQ. ID. NO. 114) (preparation described in Example 1) was tested for its ability to bind calcium and inhibit amidolytic reaction in the presence and absence of calcium. FIGS. 6e,f show changes in the proton NMR spectrum of this peptide upon the addition to the initial volume of 450 μL of 1 μL (final CaCl$_2$ concentration ~0.22 mM), additional 2 μL (final CaCl$_2$ concentration ~0.66 mM) of 100 mM CaCl$_2$, and additional 10 μL (final CaCl$_2$ concentration ~22.2 mM) of 1 M CaCl$_2$. The changes in the spectra confirm binding of calcium and the peptide with affinity in mM range.

Samples tested for inhibition potency contained in the clotting buffer 0.6 nM thrombin, 50 μM chromogenic substrate S-3266 (Chromogenix), and either no inhibitors or 2 nM of P3150, or 150 nM of the calcium-responsive disulfide-linked bivalent thrombin inhibitor. The time course of reactions is displayed in FIG. 7. Upon addition of increasing concentrations of calcium (50 and 100 mM) to the inhibitor incorporating calcium-binding linker, the potency of the latter is decreased. The same amounts of calcium produce no visible effect on the potency of control peptide P3150.

Example 5

Two peptides with sequences Val-Arg-Phe-Thr-Asp-Gly-Glu-Gly-Thr-Pro-Lys-Pro-Gln-Ser-His-Asn-Asp-Gly-Asp-Phe-Glu-Glu-Ile-Pro-Glu-Glu-Tyr-Leu-Gln (SEQ. ID. NO. 22) (mini-hirudin 1) and Ile-Arg-Phe-Thr-Asp-Gly-Glu-Gly-Thr-Pro-Asn-Pro-Glu-Ser-His-Asn-Asn-Gly-Asp-Phe-Glu-Glu-Ile-Pro-Glu-Glu-Tyr-Leu-Gln (SEQ. ID. NO. 23) (mini-hirudin 2) were designed incorporating N-terminal and C-terminal moieties presumably interacting with the active site and exosite I of thrombin. We found that they displayed high affinity to thrombin with IC$_{50}$ of 33±3 nM (mini-hirudin 1) and 14±1 nM (mini-hirudin 2) indicating a bivalent mode of binding (FIG. 8). The modular character of interaction was further implied when a candidacidal peptide known to bind laminarin (Polonelli, L.; and others, 2003, 6205-6212), or -Ala-Lys-Val-Thr-Met-Thr-Cys-Ser-Ala-Ser- (SEQ. ID. NO. 24), was inserted as a linker into the minihirudin-2 to give minihirudin-3 with a sequence of Ile-Arg-Phe-Thr-Asp-Gly-Ala-Lys-Val-Thr-Met-Thr-Cys-Ser-Ala-Ser-Gly-Asp-Phe-Glu-Glu-Ile-Pro-Glu-Glu-Tyr-Leu-Gln (SEQ. ID. NO. 25). The peptide exhibited high affinity of binding to thrombin, with IC$_{50}$ of 10±1 nM (FIG. 8), confirming the presence of bivalent interactions.

Example 6

A peptide with a sequence of Trp-Asp-Pro-Arg-Pro-Gln-Arg-His-Asn-Asp-Gly-Asp-Phe-Glu-Glu-Ile-Pro-Glu-Glu-Tyr-Leu-Gln (SEQ. ID. NO. 18) is a bivalent inhibitor of thrombin with a K$_I$ of 17 nM (subject of another patent application). The peptide is built of two moieties, an active site binding moiety, Trp-Asp-Pro-Arg-Pro-Gln-Arg-His (SEQ. ID. NO. 19), and an exosite-1 binding moiety, Asp-Phe-Glu-Glu-Ile-Pro-Glu-Glu-Tyr-Leu-Gln (SEQ. ID. NO. 20). We prepared a bivalent thrombin inhibitor with the sequence Trp-Asp-Pro-Arg-Pro-Gln-Arg-His-(CamCKK)-Asp-Phe-Glu-Glu-Ile-Pro-Glu-Glu-Tyr-Leu-Gln (SEQ. ID. NO. 21), designated as CaM-DTI, where CamCKK is a protein linker with a calcium-responsive property (Truong and others, 2001, 1069-1073). Another potentially bivalent thrombin inhibitor was derived from CaM-DTI, where the active-site targeting moiety Trp-Asp-Pro-Arg-Pro-Asn-Arg-His (SEQ. ID. NO. 18) of CaM-DTI was replaced by the sequence Ile-Arg-Phe-Thr-Asp-Gly-Glu-Gly (SEQ. ID. NO. 116) in mini-hirudins 1 and 3. In other words, this bivalent peptide incorporating the CamCKK linker was built from an N-terminal module, Ile-Arg-Phe-Thr-Asp- (SEQ. ID. NO. 72), and the exosite-1 binding moiety, Asp-Phe-Glu-Glu-Ile-Pro-Glu-Glu-Tyr-Leu-Gln (SEQ. ID. NO. 20). CaM-DTI2 has the sequence Ile-Arg-Phe-Thr-Asp-Gly-Glu-Gly-(CamCKK)-Asp-Phe-Glu-Glu-Ile-Pro-Glu-Glu-Tyr-Leu-Gln (SEQ. ID. NO. 117). This new generation of CaM-DTI was named Cam-DTI2. The sequences of the thrombin inhibitors CaM-DTI and CaM-DTI2 are shown in FIG. 9. Both CaM-DTI and CaM-DTI2 were prepared by use of a recombinant DNA approach. Typically, the proteins were expressed and purified by a standard procedure using Ni-NTA agarose affinity chromatographic column (Qiagen). The N-terminal tag was removed by digesting the sample with enterokinase with a subsequent passage through a Ni-NTA agarose affinity chromatographic column. 20 mM EDTA was added into the flow-through and the sample was desalted on a PD-10 column. The final purification was carried out with ion-exchange chromatography on a Mono-S column. Purity was confirmed by SDS-PAGE. Final samples were essentially Ca$^{2+}$-free.

Thrombin inhibition potencies of CaM-DTI and CaM-DTI2 were determined by an amidolytic assay. Kinetics of thrombin-catalyzed hydrolysis of the chromogenic substrates S-2238 or S-2366 (Chromogenix) was followed by absorbance at 405 nm on a SpectraMax plate reader thermostated at 37° C. The concentration of the substrate was 400 μM. Inhibition assays were performed in the clotting buffer with a certain fixed concentration of α-thrombin (~0.3 nM) such that linear progress curves were observed within at least 15 min in the absence of the inhibition. The total volume of the reaction mixture was 200 μl. Reactions were initiated by addition of the chromogenic substrate to the wells containing thrombin and a certain concentration of CaM-DTI premixed for less than 2 min. The concentration of CaM-DTI ranged from 25 nM to 2.5 μM. Kinetics data from initial rate experiments were used to construct Lineweaver-Burke plot; i.e. the relationship of (substrate concentration)$^{-1}$ versus (initial velocity)$^{-1}$ which were analysed by linear regression with MicroCal Origin 6.0 program (MicroCal, Md.). The K$_i$ values of the inhibitors were determined using the equation K$_i$=[I]/{(SL$_o$/SL$_1$)−1}, where [I] is the inhibitor concentration, SL$_o$ is the slope of the reaction in the absence of inhibitors, and SL$_1$ is the slope of the reaction in the presence of the inhibitor.

Figure 10A:
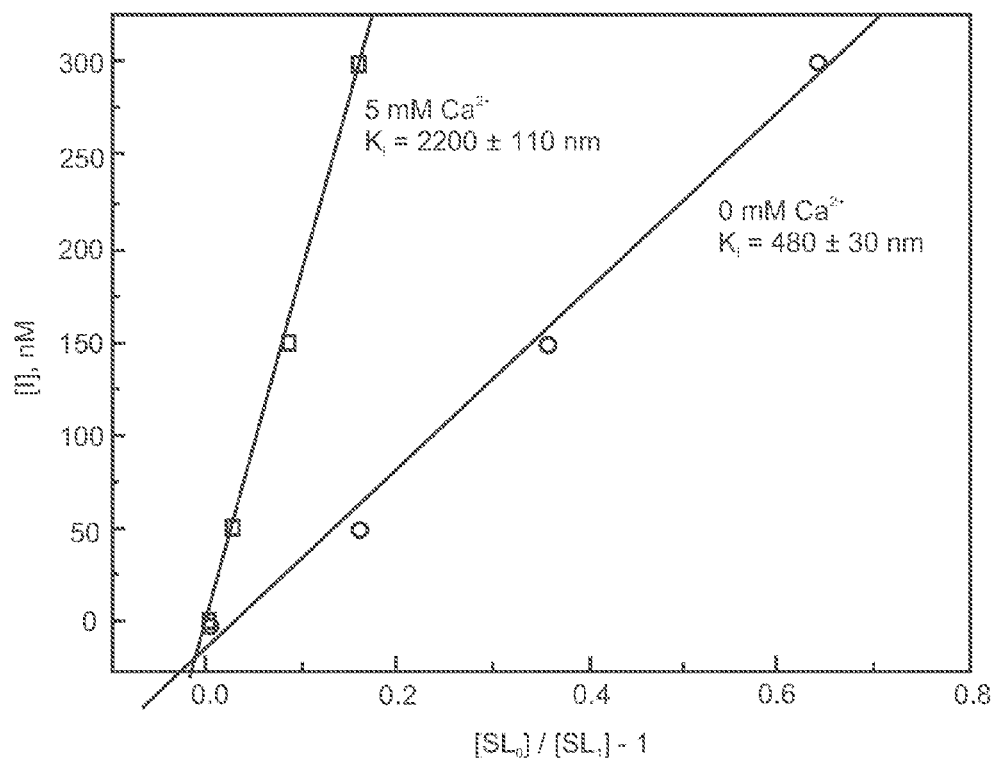

Upon the addition of 5 mM Ca$^{2+}$ an increase in inhibition constant for CaM-DTI was observed from 480 nM (calcium-free sample) to 2200 nM (calcium-loaded sample) (FIG. 10A). The CaM-DTI2 protein also inhibited the thrombin active site (FIG. 10B), but this inhibition was not affected by the presence of Ca$^{2+}$ upon concentration of 5 mM.

Figure 10B:
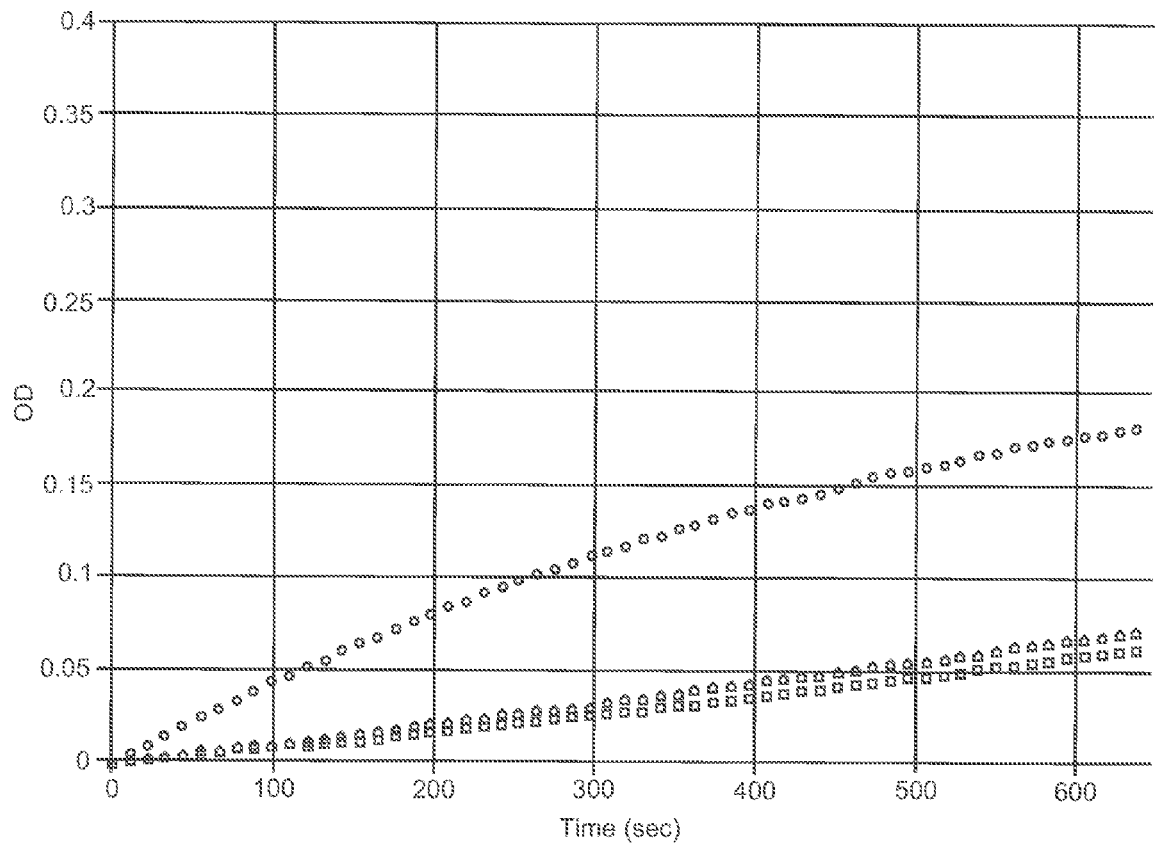

FIG. 10B depicts the kinetics of thrombin-catalyzed hydrolysis of the chromogenic S-2366 (Chromogenix).

Thrombin inhibition potency of CaM-DTI2 was determined by amidolytic assay. Kinetics of thrombin-catalyzed hydrolysis of the chromogenic substrate S-2366 (Chromogenix) was followed by absorbance at 405 nm on a SpectraMax plate reader at 25° C. The concentration of the substrate S-2366 was 50 µM. Inhibition assays were performed in the clotting buffer with a certain fixed concentration of α-thrombin (~0.6 nM). The total volume of the reaction mixture was 200 µl. Reactions were initiated by the addition of the chromogenic substrate to the wells containing thrombin in the presence of 4.2 µM and 8.4 µM CaM-DTI2. Curves represent $OD_{405}$ time course after the addition of 0.6 nM thrombin in the presence of (○) 0 nM; (Δ) 4.2 µM; and (□) 8.4 M CaM-DTI2. Inhibition of the amidolytic reaction confirming the bivalent mode of binding as shown for CaM-DTI in FIG. 10A.

Example 7

Cdc42 binds tightly to the ~40-residue extended CRIB domains of Candida Cla4 and Step 20. When subjected to NMR relaxation dispersion analysis (Tolkatchev, Xu, and Ni, 2003b, 12432-12442), these complexes exhibit no responses, as expected for a tight binding complex.

We over-expressed two peptide fragments of the extended CRIB regions from the Candida Cla4 and Candida Step 20 (or Cst20) kinases (FIG. 11): (i) mCla4 (mCst20) including the consensus CRIB motif, and (ii) cCla4 (cCst20) which comprises residues directly to the C-terminus of the minimal CRIB sequence. All the peptides described in the example were prepared via a recombinant technique as described previously (Gizachew, D. and Oswald, R. E., 2001, 14368-14375; Osborne, M. J., and others, 2003, 317-326). The identity of the final products was verified by mass spectrometry.

Cdc42 constructs were prepared as follows. DNA fragments encoding the Cdc42 protein (residues 1-178) of Candida albicans SC5314 were amplified from the genomic DNA by a standard PCR reaction using the pfu polymerase. Through PCR reactions, two restriction sites, Nde I and BamH I, were generated in the 5'-end and 3'-end, respectively. A stop codon, TAG, was placed immediately after the codon for residue 178. The PCR fragment was subcloned into pET-15b (Novagen, Madison, Wis.) and the resulting construct was defined as pCaCdc42Δ13 (Stevens & Ni, unpublished data). A CaCdc42 expression vector encoding the R150K mutation was performed using the QuickChange Site-directed Mutegenesis Kit (Stratagene, La Jolla, Calif.). The sequences of the wild-type and R150K mutant CaCdc42 (Table 4) vectors were verified by DNA sequencing.

Wild type and mutant CaCdc42 proteins were expressed in the E. coli BL21 strain as hexa-histidine fusion proteins. Cells expressing CaCdc42 were grown in LB media. Cells were harvested from 1 L culture by centrifugation at 8000 g for 30 min and re-suspended in 50 mL of lysis buffer (20 mM Tris-HCl, pH 8.0, 500 mM NaCl, 10 mM imidazole, 5 mM $MgCl_2$, 100 µM GDP, 2 µg/ml aprotinin, leupeptin and pepstatin, and 10 µg/mL benzamidine and PMSF). The collected cells were treated with lysozyme (1 mg/mL) for 30 min on ice, followed by sonication for 4 min and subsequent addition of DNase at 2 µg/ml. The insoluble fraction was removed by centrifugation at 10,000 g for 30 min. The supernatant was mixed with Ni-NTA agarose beads (Qiagen, Mississauga, ON) by rocking for one hour and then washed extensively in a column with a washing buffer (20 mM Tris-HCl, pH 8.0, 500 mM NaCl, 15 mM imidazole, 5 mM $MgCl_2$). The fusion protein was eluted with the wash buffer (50 mL) except that the concentration of imidazole was 200 mM. The protein sample was buffer-exchanged extensively using CentriPrep YM10 to remove imidazole.

The non-hydrolyzable GTP analogues, GMPPNP or GMP-PCP (Sigma, St-Louis, Mich.) were used to produce the activated, but stable nucleotide-loaded form of CaCdc42. In this work, no differences were observed for the two GTP analogues-loaded forms of Cdc42 in NMR and fluorescence experiments except that the lifetime of the complex with GMPPCP is longer than that with GMPPNP. Nucleotide exchange was facilitated by incubating CaCdc42 with a 5- to 10-fold molar excess of the non-hydrolyzable GTP analogue in the presence of 10 mM EDTA. To this mixture, 100 units of alkaline phosphatase beads were added and the mixture was gently shaken on ice for 3 hrs. The alkaline phosphatase beads were removed by filtration, followed by the addition of $MgCl_2$ to a final concentration of 15 mM. The excess unbound nucleotides were removed using a PD-10 gel filtration column (Amersham Bioscience, Piscataway, N.J.).

In order to construct a bivalent peptide ligand for Candida Cdc42 (CaCdc42) (with a suitable linker) (FIG. 12), the binding affinities of component peptides derived from the CRIB domains of Candida Cla4 and Step 20 were determined. Residue K150 of the R150K CaCdc42 mutant was covalently modified with the fluorescent probe, sNBD (Molecular Probes, Eugene, Oreg.), essentially as described by Nomanbhoy and Cerione (Nomanbhoy, T. and Cerione, R. A., 1999, 15878-15884.). The stoichiometry of the fluorescent probe per protein molecule was estimated at 1.13, based on protein concentration determined with $\epsilon_{280nm}=13,610$ $M^{-1}$ $cm^{-1}$ (Gill, S. C. and von Hippel, P. H., 1989, 319-326), and using the absorbance of the sNBD moiety of $\epsilon_{463nm}=22,000$ $M^{-1}$ $cm^{-1}$. Interaction of the CRIB peptides with sNBD-labeled CaCdc42 was monitored using extrinsic fluorescence measurements with a Hitachi F-2500 fluorescence spectrophotometer. Samples of sNBD-labeled, activated CaCdc42 were added in the assay buffer (50 mM phosphate, pH 6.8, 50 mM NaCl and 5 mM $MgCl_2$) to a cuvette being continuously stirred. The protein concentration was 1 µM. Individual CRIB peptide dissolved in the same assay buffer was added dropwise to the cuvette. The mixture was excited at 488 nm with an excitation slit width of 5 nm. The emission spectra were scanned from 510 nm to 590 nm. The fluorescence emission intensity at the emission maximum 545 nm was determined from each spectrum and the final value was obtained by averaging the values from five scans of the same sample. Control titration experiments were performed by adding the same volume of buffer instead of peptide. Each set of the titration data was repeated three times.

FIG. 13 shows binding isotherms obtained following the CRIB-induced changes in the sNBD fluorescence of the CaCdc42 (R150K) protein. The $K_d$ values for the binding of the CRIB peptides to sNBD-labeled activated CaCdc42 were determined by fitting the fluorescence titration data to a simple bimolecular association model as described by Leonard et al (Leonard, D. A., and others, 1997, 1173-1180).

The association between CaCdc42 (P) and a CRIB peptide (L) can be described by the following equation $$P + L \underset{k_{off}}{\overset{k_{on}}{\rightleftharpoons}} P \cdot L$$

The fluorescence intensity (F) is related to the dissociation constant, $K_d$ as follows, $$F = F_0 + (F_t - F_0)\left[\frac{(K_d + L_T + P_T) - \sqrt{(K_d + L_T + P_T)^2 - 4P_T L_T}}{2P_T}\right]$$

where $F_0$ and $F_t$ are the fluorescence intensities at the starting and end points of the titration, respectively. $P_T$ is the total concentration of sNBD-labeled activated CaCdc42 and $L_T$ is the total concentration of the CRIB peptide at any point in the titration. Fitting of the data was carried out using the computer program Microcal Origin™ 6.0 (Northampton, Mass.). Average $K_d$ values were determined from multiple independent measurements.

The average apparent $K_d$ values for different CRIB peptides are summarized in Table 2. As expected, the extended CRIB (eCRIB) fragments exhibited the strongest affinities of binding to CaCdc42 in the low nanomolar range. The mCRIB fragments containing the consensus CRIB sequence, ISXPXXFXHXXHVGXD (SEQ. ID. NO. 26) (Burbelo, P. D., Drechsel, D., and Hall, A., 1995, 29071-29074), also had moderately strong binding affinities in micromolar concentrations, but clearly, as seen previously for the human PAK homologues (Rudolph, M. G., Bayer, P., Abo, A., Kuhlmann, J., Vetter, I. R., and Wittinghofer, A., 1998, 18067-18076; Thompson, G., Owen, D., Chalk, P. A., and Lowe, P. N., 1998, 7885-7891), require extra residues to retain stronger binding to Cdc42. The cCRIB peptides exhibited much weaker affinities to the CaCdc42 protein. The $K_d$ value of cCla4 for binding to CaCdc42 is in a high micromolar concentration (275 μM). An even weaker binding ($K_d$=1160 μM) was observed between cCst20 and CaCdc42 with the current fluorescence titration strategy.

Fluorescence measurements of cross-titrations were used to quantify allosteric effects (Table 2). The affinity of the Cla4 peptide fragments for CaCdc42 was not significantly affected by the addition of the cognate peptide. In contrast, the affinities of the Cst20 peptide fragments preincubated with CaCdc42 exhibited a dramatic enhancement in binding for CaCdc42 by ~5.5-fold, upon addition of the cognate Cst20 peptide (Table 2). Thus, upon addition of mCst20 to the cCst20/CaCdc42 complex, the affinity of cCst20 for CaCdc42 increased from a $K_d$ of 1160 μM to 207 μM (Table 2 and FIG. 13c). Similarly, mCst20 affinity for CaCdc42 increased from 0.43 μM to 0.081 μM when cCst20 was added to a preincubated mCst20/CaCdc42 complex. These results strongly suggest that the eCst20 and eCla4 peptides exhibit different mechanisms for binding CaCdc42, in which long eCst20 peptide utilizes a cooperative mechanism for high-affinity interaction while eCla4 does not.

Modular nature of interactions of m- and c-CRIB fragments is confirmed by the binding affinities of hybrid peptides incorporating m- and c-CRIBs from different molecular species. Both mCla4-cCst20 and mCst20-P-cCla4 constructs (FIG. 11) displayed affinities of the same order of magnitude as the original eCRIB peptides (Table 2). Moreover, incorporation of -Ser-Gly-Ser-Gly- (SEQ. ID. NO. 27) and -Arg-Lys-Ser-Leu-Thr-Ile-Tyr-Ala-Gln-Val-Gln-Lys-(SEQ. ID. NO. 28) linkers (FIG. 11) into the eCla4 sequence preserved a bivalent mode of binding, since the affinity of the chimeric peptide was significantly stronger than those of H1 and H2 heads (Table 2).

Example 8

The dissociation constant ($K_i$) for the interaction between SAP-SH2 and the eCla4-SLAM peptide was obtained by fitting fluorescence titration data (FIGS. 14A and 14B) using the following equation $$K_d^{app} = K_d + \frac{K_d}{K_i}[SH_2]$$

where, $K_d^{app}$, $K_d$ are the apparent dissociation constants between CaCdc42 and eCla4-SLAM in the presence or absence of SAP-SH2, respectively. $K_i$ is the dissociation constant for the binding interaction between SAP-SH2 and the linker portion (i.e. the SLAM sequence of eCla4-SLAM). The value of $K_i$ determined from these experiments is 362 μM, indicating that the SLAM sequence in the eCla4-SLAM peptide preserved the binding affinity to SAP-SH2 (Li et al and Pawson, Curr. Biol. 9, 1355-1362, 1999).

A peptide of the sequence Bbs-Arg-dPip-Gly-Arg-Lys-Ser-Leu-Thr-Ile-Tyr-Ala-Gln-Val-Gln-Lys-Gly-Asp-Phe-Glu-Glu-Ile-Pro-Glu-Glu-Tyr-Leu-Gln (SEQ. ID. NO. 102), was synthesized and purified which contains as linker the SLAM sequence with specific binding to SAP-SH2 in the absence of tyrosine phosphorylation (Li et al and Pawson, Curr. Biol. 9, 1355-1362, 1999). The peptide was added at the concentrations of 10, 15, 20, 30, 40, 50 and 60 nM to 0.6 nM thrombin in the clotting buffer. Optical absorbance increase at 420 nm caused by fibrin clot formation was measured at 25° C. using the Spectramax plate reader. The onset clotting time was determined as an intersection of the baseline and the extrapolated linear portion of the OD change curve. The concentration of the peptide needed to double the clotting time was defined as $IC_{50}$. The peptide is found to be a potent inhibitor of thrombin with $IC_{50}$=7±1 nM (FIG. 14C). Also, to the clotting buffer containing 0.6 nM thrombin and 25 nM of the inhibitor were added 5 and 10 μM SAP-SH2 from the stock solution of 116 μM SAP-SH2 in 10 mM 2-[N-Morpholino]ethanesulfonic buffer (MES) at pH 5.0. The clotting assays serving as control experiments included thrombin+inhibitor, thrombin+SAPSH2, and thrombin alone. FIGS. 14D and 14E shows the course of the optical absorbance changes at 420 nm, and at 25° C., demonstrating the reversal of thrombin inhibition by SAP-SH2.

Example 9

The tweezer-like bivalent ligands can be attached to the protein target, either chemically or through recombinant techniques. We used the recombinant approach to conjugate *Candida albicans* Cdc42 (CaCdc42) with the full-length CRIB peptides from *Candida* Cla4 and Step 20 (FIG. 11). A model for a conjugated complex of CaCdc42 and the eCRIBs via a polymeric linker is displayed in FIG. 15a. Resonance assignments of the $^1$H-$^{15}$N HSQC spectra for *Candida* Cla4-eCRIB in a conjugated complex with CaCdc42 are displayed in FIG. 15b. The resonance peaks of the Cla4-eCRIB have the same pattern as those in the non-covalent complex. However, the conjugated complex is more stable (>3 months) than the non-covalent one (<one week). The $^1$H-$^{15}$N HSQC spectrum of *Candida* Cst20-eCRIB in a conjugated complex with CaCdc42 is shown in FIG. 15c. One potential application of the stably-conjugated complex is for discovering stronger and specific binding molecules to Cdc42 is outlined in FIG. 15d. More specifically, NMR techniques such as relaxation and H/D exchange can be used to detect the dissociation of a conjugated bivalent ligand by competing monovalent small molecules.

Example 10

Molecular species and methods of invention can also be used to design new molecules for pharmaceutical intervention. Medical intervention in case of an injury to an internal organ requires a strategy to seal the wound. Fibrin sealant is found to be effective and can be used safely on vital organs. It is thus widely used as a bioactive hemostat in cases of internal injury. The formulation that is commercially available (e.g. Tisseel VH Fibrin Sealant, Baxter) contains two major components: thrombin and fibrinogen. When both components are reconstituted and mixed thrombin catalyses the conversion of fibrinogen to fibrin, which in turn forms a fibrin scaffold or sealant. One of the limitations of the present formulation is that once reconstituted, thrombin proteolytically degrades itself.

Thus, there is provided herein a new formulation, wherein the proteolytic activity of thrombin is inhibited by a specific bivalent inhibitor Bbs-Arg-(D-Pip)-Gly-(Ser-Pro-His-Tyr (P)-Glu-Lys-Val-Ser-Gly)-Asp-Phe-Glu-Glu-Ile-Pro-Glu-Glu-Tyr-Leu-Gln (P3170) (SEQ. ID. NO. 82) with a controllable polymeric linker binding to SH2 domain (FIG. 4). Therefore in the modified formulation, thrombin and inhibitor can be premixed and will stay inactive (and stable) until exposed to SH2.

The middle auricular artery of eight rabbits was cut transversely with a scalpel. Two rabbits were left untreated to measure the bleeding time. A commercial source of fibrin glue (one fresh sample, one incubated overnight at 37° C.) was applied to the wound of two other rabbits. The fibrin glue containing inhibitor-stabilized thrombin component, "Thrombin 4", was applied to another pair of rabbits immediately after activation with SH2. The fibrin glue containing inhibitor-stabilized and highly purified human α-thrombin (Haemotologics), replacing the "Thrombin 4" component from the Tisseel kit, was applied to the last pair of rabbits immediately after SH2 activation. The final table of applied formulations employed in the example was as follows:

|  | Left ear | Right ear |
| --- | --- | --- |
| Group 1- R1 | Bleeding rabbit (no sealant) |  |
| Group 1- R2 | Bleeding rabbit (no sealant) |  |
| Group 2- R1 | Syringe (1) - 250 µL Commercial Tisseel solution, prepared fresh Syringe (2) - 250 µL Tisseel "Thrombin 4" solution, prepared fresh | Syringe (1) - 250 µL Commercial Tisseel solution, prepared fresh Syringe (2) - 250 µL Tisseel "Thrombin 4" solution, prepared the night before and incubated o/n at 37 C. |
| Group 2- R2 | Same sample as above | Same sample as above |
| Group 3- R1 | Syringe (1) - 250 µL Commercial Tisseel solution, prepared fresh + SH2 to 12 µM concentration. | Syringe (1) - 250 µL Commercial Tisseel solution, prepared fresh + SH2 to 12 µM concentration. |
| | Syringe (2) - 250 µL Tisseel "Thrombin 4" solution + P3170 to 8 nM concentration, prepared the night before and incubated o/n at 37 C. | Syringe (2) - 250 µL Tisseel "Thrombin 4" solution, prepared the night before and incubated o/n at 37 C. |
| Group 3- R2 | Same sample as above | Same sample as above |
| Group 4- R1 | Syringe (1) - 250 µL Commercial Tisseel solution, prepared fresh + SH2 to 12 µM concentration. | Syringe (1) - 250 µL Commercial Tisseel solution, prepared fresh + SH2 to 12 µM concentration. |
| | Syringe (2) - 250 µL "α-thrombin (10$^{-5}$)" solution + P3170 to 8 nM concentration, prepared the night before and incubated o/n at 37 C. | Syringe (2) - 250 µL "α-thrombin (10$^{-5}$)" solution, prepared the night before and incubated o/n at 37 C. |
| Group 4- R2 | Same sample as above | Same sample as above |

SH2-activated fibrin glue with P3170 inhibitor was able to seal the wound after ~5 minutes (FIG. 18).

In an embodiment of the invention there is provided a multivalent binding molecule and uses thereof. The molecule is useful in binding a target under certain conditions and releasing it under other conditions. The molecule has the general formula (1) of

wherein,

BM1 is a binding moiety 1 having an affinity for site 1 on the target,

BM2 is a binding moiety 2 having an affinity for a site other than site 1 on the target, n is 1 or greater, and L is a linker joining BM1 and BM2, said linker being adapted to respond to a change in its environment with a change in conformation and/or flexibility, wherein BM1 and BM2 may be the same or different, and when n>1, different BM2 moieties may have affinities for different binding sites on the target. BM1 and BM 2 are selected such that in use each of the BM1 and BM2 existing separately has a lower binding affinity then the complex of BM1 and BM2 does when they are linked to form the molecule. In some instances the ligand is a polypeptide. In some instances the ligand is covalently attached to its target. In some instances the target is a protein, and the ligand is attached to its protein target by means of recombinant conjugation. In some instances the linkers are modified by means of binding to a biomolecule. In some instances the linkers are modified by means of covalent modification. In some instances the linkers are modified by means of a local environment change. In some instances the linker binds to an antibody. In some instances the linker binds to an SH2 domain. In some instances the linker binds to Cdc42. In some instances the linker binds to prothrombin. In some instances the linker binds to metal ion. In some instances the linker binds to calcium. In some instances the linker binds to a cell surface. In some instances the linker sequence contains at least two residues, selected from the group of tyrosine; serine; threonine; histidine; phosphotyrosine; phosphoserine; phoshothreonine; phosphohistidine.

In some instances the linker sequence is selected from the group consisting of

-Glu-Gln-Lys-Leu-Ile-Ser-Glu-Glu-Asp-Leu- (SEQ ID NO: 12);

-Gly-Gly-Asn-Ser-Gly-Val-Ser-Gly-Pro-Ile-Asn-Phe-Thr-His-Lys-Val-His-Val-Gly-Phe-Asp-Pro-Ala-Ser-Gly-Asn-Phe-Thr-Gly-Leu-Pro-Asp-Thr-Trp-Lys-Ser-Leu-Leu-Gln-His-Ser-Lys-Ile-Thr- (SEQ ID NO: 37);

-Glu-Val-Asn-Ile-Lys-Ile-Ser-Thr-Pro-Phe-Asn-Ala-Lys-His-Leu-Ala-His-Val-Gly-Ile-Asp-Asp-Asn-Gly-Ser-Tyr-Thr-Gly-Leu-Pro-Ile-Glu-Trp-Glu-Arg-Leu-Leu-Ser-Ala-Ser-Gly-Ile-Thr- (SEQ ID NO: 38);

-Thr-Leu-Asp-Leu-Asn-Thr-Pro-Val-Asp-Lys-Thr-Ser-Asn- (SEQ ID NO: 39);

-Ser-Val-Val-Pro-Arg-Pro-Gln-Leu-His-Asn-Asp- (SEQ ID NO: 40);

-Ser-His-Ala-Pro-Arg-Pro-Gln-Ile-His-Asn-Asp- (SEQ ID NO: 41);

-Asn-Gly-Arg-Lys-Ile-Cys-Leu-Asp-Leu-Gln-Ala-Pro-Leu-Tyr-Lys-Lys-Ile-Ile-Lys-Lys-Leu-Leu-Glu-Ser- (SEQ ID NO: 42);

-Asn-Gly-Arg-Lys-Ile-Cys-Leu-Glu-Leu-Arg-Ala-Pro-Leu-Tyr-Lys-Lys-Ile-Ile-Lys-Lys-Leu-Leu-Glu-Ser- (SEQ ID NO: 43);

-His-His-Leu-Gly-Gly-Ala-Lys-Gln-Ala-Gly-Asp-Val- (SEQ ID NO: 44);

-Tyr-Met-Glu-Ser-Arg-Ala-Asp-Arg- (SEQ ID NO: 45);

-Gln-Ser-His-Asn-Arg- (SEQ ID NO: 46);

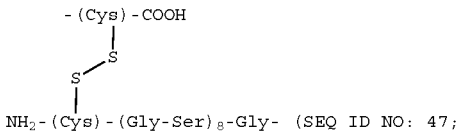

NH$_2$-(Cys)-(Gly-Ser)$_8$-Gly- (SEQ ID NO: 47;

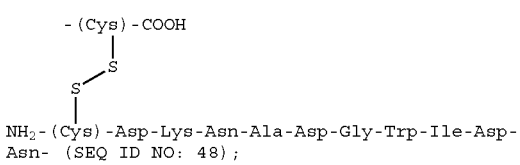

NH$_2$-(Cys)-Asp-Lys-Asn-Ala-Asp-Gly-Trp-Ile-Asp-Asn- (SEQ ID NO: 48);

-Asp-Lys-Asn-Ala-Asp-Gly-Trp-Ile-Asp-Asn-Gly-Glu-Phe-Glu- (SEQ ID NO: 49);

-Asp-Lys-Asn-Ala-Asp-Gly-Trp-Ile-Asp-Asn-Gly-Asp-Phe-Glu- (SEQ ID NO: 17);

-Ala-Lys-Val-Thr-Met-Thr-Cys-Ser-Ala-Ser- (SEQ ID NO: 24);

-Arg-Lys-Ser-Leu-Thr-Ile-Tyr-Ala-Gln-Val-Gln-Lys- (SEQ ID NO: 28);

In some instances the FL sequence is selected from the group consisting of

-(Gly-Ser)$_2$-; (SEQ ID NO: 50)

-(Gly-Ser)$_4$- (SEQ ID NO: 51);

-(Gly-Ser)$_6$- (SEQ ID NO: 52);

-(Gly-Ser)$_8$- (SEQ ID NO: 53);

-(Gly-Ser)$_{10}$- (SEQ ID NO: 54);

-(Gly-Ser)$_{12}$- (SEQ ID NO: 55);

-(Gly-Ser)$_{14}$- (SEQ ID NO: 56);

-Gly-Cys...Cys-(Gly-Ser)$_8$- (SEQ ID NO: 57);

-(Gly-Ser)$_4$-Gly-Lys-(Gly-Ser)$_5$- (SEQ ID NO: 58);

-Ser-Pro-His-Tyr-Glu-Lys-Val-Ser-Gly- (SEQ ID NO: 59);

-(Ser-Pro-His-Tyr-Glu-Lys-Val-Ser-Gly)$_2$- (SEQ ID NO: 60);

-Ser-Pro-His-Tyr(P)-Glu-Lys-Val-Ser-Gly- (SEQ ID NO: 61);

-(Ser-Pro-His-Tyr(P)-Glu-Lys-Val-Ser-Gly)$_2$- (SEQ ID NO: 62);

-Pro-His-Tyr-Glu-Lys-Val-Ser- (SEQ ID NO: 63);

-Pro-His-Tyr-Glu-Lys-Val-Ser-Gly-Ser-Pro-His-Tyr-Glu-Lys-Val-Ser- (SEQ ID NO: 64);

-Pro-His-Tyr(P)-Glu-Lys-Val-Ser- (SEQ ID NO: 65);

-Pro-His-Tyr(P)-Glu-Lys-Val-Ser-Gly-Ser-Pro-His-Tyr(P)-Glu-Lys-Val-Ser- (SEQ ID NO: 66);

wherein Tyr(P) is O-phosphotyrosine;

In some instances the FL sequence is selected from the group consisting of -Ser-Val-Val-Pro-Asn-Aaa-Bbb-Leu-Ccc-Ddd-Asp- (SEQ ID NO: 67); wherein Aaa, Bbb, Ccc, and Ddd—natural amino acids;

In some instances the molecule is a thrombin inhibitor;

In some instances the BM1 sequence is selected from the group consisting of:

Bbs-Arg-(D-Pip) (SEQ ID NO: 68);

Bbs-Arg-(D-Pip)-Gly (SEQ ID NO: 35);

where Bbs is 4-tert-butylbenzenesulfonyl, D-Pip is D-pipecolic acid;

In some instances the BM1 sequence is a subsequence from an amino acid sequence selected from the group consisting of

```
Val-Arg-Phe-Thr-Asp-Gly-Glu-Gly-Thr-

Pro-Lys (SEQ ID NO: 69);

Val-Arg-Phe-Thr-Asp (SEQ ID NO: 70);

Ile-Arg-Phe-Thr-Asp-Gly-Glu-Gly-Thr-

Pro-Asn (SEQ ID NO: 71);

Ile-Arg-Phe-Thr-Asp (SEQ ID NO: 72);

Trp-Asp-Pro-Arg-Pro-Gln-Arg-His (SEQ ID NO: 19);
```

In some instances the BM2 amino acid sequence is selected from the group consisting of:

```
Asp-Phe-Glu-Glu-Ile-Pro-Glu-Glu-Tyr-

Leu-Gln (SEQ ID NO: 20);

Gly-Asp-Phe-Glu-Glu-Ile-Pro-Glu-Glu-

Tyr-Leu-Gln (SEQ ID NO: 36);
```

In some instances the molecule is

WDPRPQRHADQLTEEQIAEFKEAFSLFDKGDGTITTKELGTVMRSLGQNP

TEAELQDMINEVDADGNGTIDFPEFLTMMARKMKDTGGVKLIPSWTTVIL

VKSMLRKRSFGNPFGGDSEEEIREAFRVFDKDGNGYISAAELRHVMTNLG

EKLTDEEVDEMIREADIDGDGQVNYEEFVQMMTAKDFEEIPEEYLQ (SEQ ID NO: 21);

In some instances the molecule is a ligand of Cdc42;
In some instances the BM1 sequence is a subsequence from an amino acid sequence selected from the group consisting of Gly-Gly-Asn-Ser-Gly-Val-Ser-Gly-Pro-Ile-Asn-Phe- Thr-His-Lys-Val-His-Val-Gly-Phe-Asp-Pro-Ala-Ser (SEQ ID NO: 92);

Gly-Gly-Asn-Ser-Gly-Val-Ser-Gly-Pro-Ile-Asn-Phe-

Thr-His-Lys-Val-His-Val-Gly-Phe-Asp (SEQ ID NO: 93);

Glu-Val-Asn-Ile-Lys-Ile-Ser-Thr-Pro-Phe-Asn-Ala-

Lys-His-Leu-Ala-His-Val-Gly-Ile-Asp-ASp-Asn-Gly (SEQ ID NO: 94);

Glu-Val-Asn-Ile-Lys-Ile-Ser-Thr-Pro-Phe-Asn-Ala-

Lys-His-Leu-Ala-His-Val-Gly-Ile-Asp (SEQ ID NO: 95);

In some instances the BM2 sequence is a subsequence from an amino acid sequence selected from the group consisting of Gly-Asn-Phe-Thr-Gly-Leu-Pro-Asp-Thr-Trp-Lys-Ser- Leu-Leu-Gln-His-Ser-Lys-Ile-Thr (SEQ ID NO: 96);

Asn-Phe-Thr-Gly-Leu-Pro-Asp-Thr-Trp-Lys-Ser-Leu-

Leu-Gln-His-Ser-Lys-Ile-Thr (SEQ ID NO: 97);

Gly-Ser-Tyr-Thr-Gly-Leu-Pro-Ile-Glu-Trp-Glu-Arg-

Leu-Leu-Ser-Ala-Ser-Gly-Ile-Thr (SEQ ID NO: 98);

Ser-Tyr-Thr-Gly-Leu-Pro-Ile-Glu-Trp-Glu-Arg-Leu-

Leu-Ser-Ala-Ser-Gly-Ile-Thr (SEQ ID NO: 99);

In some instances the molecule is selected from the group consisting of:

Gly-Gly-Asn-Ser-Gly-Val-Ser-Gly-Pro-Ile-Asn-Phe-

Thr-His-Lys-Val-His-Val-Gly-Phe-Asp-Ser-Gly-Ser-

Gly-Asn-Phe-Thr-Gly-Leu-Pro-Asp-Thr-Trp-Lys-Ser-

Leu-Leu-Gln-His-Ser-Lys-Ile-Thr (SEQ ID NO: 100);

Gly-Gly-Asn-Ser-Gly-Val-Ser-Gly-Pro-Ile-Asn-Phe-

Thr-His-Lys-Val-His-Val-Gly-Phe-Asp-Arg-Lys-Ser-

Leu-Thr-Ile-Tyr-Ala-Gln-Val-Gln-Lys-Asn-Phe-Thr-

Gly-Leu-Pro-Asp-Thr-Trp-Lys-Ser-Leu-Leu-Gln-His-

Ser-Lys-Ile-Thr (SEQ ID NO: 101);

In an embodiment of the invention there is provided a method to obtain the polypeptide molecule according to claim 3 with high affinity to a protein target, said method comprising steps of:
a) Identification of two binding peptide moieties to two different binding sites of the target based on already existing polypeptide ligands with high affinity;
b) Establishing a weaker binding peptide moiety using NMR titration or NMR relaxation dispersion spectroscopy;
c) Connecting the peptide moieties with a polymeric linker;
d) Increasing the bivalent affinity by sequence optimization of the weaker moiety by means of phage display;

In an embodiment of the invention there is provided a method to prolong the lifetime of reconstituted autocatalytic protease said method comprising the steps of
a) Inhibiting the protease with a bivalent protease inhibitor containing a controllable linker,
b) Releasing and activating the protease with an appropriate linker-targeted antidote;

In some instances the protease is thrombin.

In some instances thrombin is a component of a fibrin sealant kit.

Thus, it will be apparent that there has been provided herein multivalent binding molecules containing linkers through which binding can be modulated.

TABLE 1

$IC_{50}$ and $K_I$ values of thrombin inhibitors of the series
Bbs-R-(D-Pip)-linker-GDFEEIPEEYLQ (SEQ. ID. NO. 2).

| | linker | $K_I$, nM (25° C.) | $IC_{50}$, nM (37° C.) | FIG. |
|---|---|---|---|---|
| P3149, SEQ. ID. NO. 73 | GSGS (SEQ. ID. NO. 50) | | 9.7 ± 0.7 | 2a |
| P3150, SEQ. ID. NO. 74 | GSGSGSGS (SEQ. ID. NO. 51) | 0.5 ± 0.2 | 0.5 ± 0.1 | 2b |
| P3151, SEQ. ID. NO. 75 | GSGSGSGSGSGS (SEQ. ID. NO. 52) | 0.6 ± 0.1 | 0.5 ± 0.1 | 2c |
| P3152, SEQ. ID. NO. 76 | GSGSGSGSGSGSGS (SEQ. ID. NO. 53) | 1.3 ± 0.3 | 0.7 ± 0.1 | 2d |

TABLE 1-continued

IC$_{50}$ and K$_I$ values of thrombin inhibitors of the series
Bbs-R-(D-Pip)-linker-GDFEEIPEEYLQ (SEQ. ID. NO. 2).

| | linker | K$_I$, nM (25° C.) | IC$_{50}$, nM (37° C.) | FIG. |
|---|---|---|---|---|
| P3153 SEQ. ID. NO. 77 | GSGSGSGSGSGSGSGSGSGS (SEQ. ID. NO. 54) | 2.0 ± 0.3 | 1.0 ± 0.1 | 2e |
| P3160, SEQ. ID. NO. 78 | GSGSGSGSGGSGSGSGSGSGS (SEQ. ID. NO. 55) | 4.6 ± 0.8 | 2.8 ± 0.1 | 2f |
| P3159, SEQ. ID. NO. 79 | GSGSGSGSGSGSGSGSGSGSGSGS (SEQ. ID. NO. 56) | 6.7 ± 1.9 | 3.5 ± 0.2 | 2g |
| P3172-P3165, SEQ. ID. NO. 83 | Gly-Cys...Cys-GSGSGSGSGSGSGSGS (SEQ. ID. NO. 57) | | 1.1 ± 0.2 | 2h |
| P3169, SEQ. ID. NO. 80 | GSPHYEKVS (SEQ. ID. NO. 123) Ligand of an SH2 domain from Grb4, dephosphorylated | 1.0 ± 0.2 | 0.4 (25° C.) | 3a |
| P3170, SEQ. ID. NO. 82 | GSPH(Y(P))EKVS (SEQ. ID. NO. 124) Ligand of an SH2 domain from Grb4, phosphorylated | 1.5 ± 0.4 | 0.7 (25° C.) | 3b |
| P3161, SEQ. ID. NO. 81 | GSPHYEKVSGSPHYEKVS (SEQ. ID. NO. 125) Tandem of two peptide ligands to SH2 from Grb4, dephosphorylated | | 0.7 (25° C.) | 3c |
| P3162, SEQ. ID. NO. 14 | GSPH(Y(P))EKVSGSPH(Y(P))EKVS (SEQ. ID. NO. 126) Tandem of two peptide ligands to SH2 from Grb4, phosphorylated | | 19 ± 1 (25° C.) | 3d |
| P3174, SEQ. ID. NO. 84 | GSGSGSGSGKGSGSGSGSGS (SEQ. ID. NO. 58) Lys in the middle of a long GS repeat linker | | 1.6 ± 0.9 (25° C.) | 2j |
| P3181, SEQ. ID. NO. 85 | GTLDLNTPVDKTSN (SEQ. ID. NO. 103) C5a receptor peptide | | 1.9 ± 0.2 | 2i |
| P3182, SEQ. ID. NO. 13 | GEQKLISEEDL (SEQ. ID. NO. 123) c-myc peptide | 66 ± 13 | ~25 | |
| P3209, SEQ. ID. NO. 32 | GSVVPRPQLHND (SEQ. ID. NO. 105) Prothrombin-binding linker 1 (VV) | | 1.1 | 2k |
| P3210, SEQ. ID. NO. 33 | GSHAPRPQIHND (SEQ. ID. NO. 104) Prothrombin-binding linker 2 (HA) | | 0.6 | 2l |
| P3234, SEQ. ID. NO. 88 | GHHLGGAKQAGDV (SEQ. ID. NO. 106) Fibrinogen γ-chain 400-411, integrin specific | | 3.9 ± 0.8 | 2m |
| P3236, SEQ. ID. NO. 89 | GYMESRADR (SEQ. ID. NO. 107) Fibrinogen antagonist, also targets the fibrinogen-integrin interaction | | 1.0 ± 0.5 | 2n |
| P3238, SEQ. ID. NO. 90 | GQSHNR (SEQ. ID. NO. 108) Linkers conferring a RGDF sequence, with potential | | 2 ± 1 | 2o |

TABLE 1-continued

IC$_{50}$ and K$_I$ values of thrombin inhibitors of the series
Bbs-R-(D-Pip)-linker-GDFEEIPEEYLQ (SEQ. ID. NO. 2).

| | linker | K$_I$, nM (25° C.) | IC$_{50}$, nM (37° C.) | FIG. |
|---|---|---|---|---|
| | binding to an integrin receptor | | | |
| 3243-3255, SEQ. ID. NO. 91 | Gly-Cys...Cys-DKNADGWIDN (SEQ. ID. NO. 48) Calcium-binding linker | | | 7 |
| P3291, SEQ. ID. NO. 102 | GRKSLTIYAQVQK (SEQ. ID. NO. 128) SLAM peptide (ligand for SAP-SH2) | | 7 ± 1 | |

TABLE 2

Dissociation constants for binding of *Candida* CRIB
fragments to CaCdc42 measured by fluorescence titration.

| Peptide | mCla4 | mCst20 | cCla4 | cCst20 | eCla4 | eCst20 |
|---|---|---|---|---|---|---|
| K$_d^m$ (μM) | 4.2 ± 0.15 | 0.43 ± 0.03 | 275 ± 9 | 1160 ± 106 | 0.025 ± 0.002 | 0.046 ± 0.002 |

| Peptide | mCla4 (+cCla4) | mCst20 (+cSt20) | cCla4 (+mCla4) | cCst20 (+mCst20) |
|---|---|---|---|---|
| K$_d^m$ (μM) | 4.1 ± 0.13 | 0.081 ± 0.002 | 311 ± 12 | 207 ± 10 |

| Peptide | mCla4-cCst20 | mCst20-cCla4 | mCst20-P-cCla4 | eCla4-SG | eCla4-SLAM |
|---|---|---|---|---|---|
| K$_d^m$ (μM) | 0.031 ± 0.002 | 2.64 ± 0.20 | 0.093 ± 0.01 | 0.067 ± 0.008 | 0.127 ± 0.07 |

TABLE 3

| SEQ. ID. NO. | SEQUENCE |
|---|---|
| SEQ. ID. NO. 1 | Gly-Asp-Phe-Glu-Glu-Ile-Glu-Glu-Tyr-Leu-Gln |
| SEQ. ID. NO. 2 | Bbs-Arg-(D-Pip)-linker-Gly-Asp-Phe-Glu-Glu-Ile-Pro-Glu-Glu-Tyr-Leu-Gln |
| SEQ. ID. NO. 3 | [-linker-Gly-Asp-Phe-Glu-Glu-Ile-Pro-Glu-Glu-Tyr-Leu-Gln] |
| SEQ. ID. NO. 4 | Bbs-Arg-(D-Pip)-Gly-Cys |
| SEQ. ID. NO. 5 | Cys-(Gly-Ser)$_8$-Gly-Asp-Phe-Glu-Ile-Pro-Glu-Glu-Tyr-Leu-Gln |
| SEQ. ID. NO. 6 | Bbs-Arg-(D-Pip)-Gly-Cys |
| SEQ. ID. NO. 7 | Cys-(Gly-Ser)$_8$-Gly-Asp-Phe-Glu-Ile-Pro-Glu-Glu-Tyr-Leu-Gln |
| SEQ. ID. NO. 8 | Cys-Pro-His-Tyr-Glu-Lys-Val-Ser-Gly |
| SEQ. ID. NO. 9 | Bbs-Arg-(D-Pip)-Gly-(Ser-Pro-His-B-Glu-Lys-Val-Ser-Gly)n-Asp-Phe-Glu-Ile-Pro-Glu-Glu-Tyr-Leu-Gln |
| SEQ. ID. NO. 10 | Bbs-Arg-(D-Pip)-Gly-(Ser-Pro-His-Tyr(P)-Glu-Lys-Val-Ser-Gly)-Asp-Phe-Glu-Ile-Pro-Glu-Glu-Tyr-Leu-Gln |
| SEQ. ID. NO. 11 | Bbs-Arg-(D-Pip)-Gly-(Ser-Pro-His-Tyr-Glu-Lys-Val-Ser-Gly)n-Asp-Phe-Glu-Glu-Ile-Pro-Glu-Glu-Tyr-Leu-Gln |
| SEQ. ID. NO. 12 | Glu-Gln-Lys-Leu-Ile-Ser-Glu-Glu-Asp-Leu |
| SEQ. ID. NO. 13 | Bbs-Arg-(D-Pip)-Gly-Glu-Gln-Lys-Leu-Ile-Ser-Glu-Glu-Asp-Leu-Gly-Asp-Phe-Glu-Glu-Ile-Pro-Glu-Glu-Tyr-Leu-Gln |
| SEQ. ID. NO. 14 | Bbs-Arg-(D-Pip)-Gly-(Ser-Pro-His-Tyr(P)-Glu-Lys-Val-Ser-Gly)$_2$-Asp-Phe-Glu-Glu-Ile-Pro-Glu-Glu-Tyr-Leu-Gln |
| SEQ. ID. NO. 15 | Bbs-Arg-(D-Pip)-Gly-Cys... |
| SEQ. ID. NO. 16 | Bbs-Arg-(D-Pip)-Gly-Cys ... Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln |
| SEQ. ID. NO. 17 | Asp-Lys-Asn-Ala-Asp-Gly-Trp-Ile-Asp-Asn-Gly-Asp-Phe-Glu |
| SEQ. ID. NO. 18 | Trp-Asp-Pro-Arg-Pro-Gln-Arg-His-Asn-Asp-Gly-Asp-Phe-Glu-Glu-Ile-Pro-Glu-Glu-Tyr-Leu-Gln |
| SEQ. ID. NO. 19 | Trp-Asp-Pro-Arg-Pro-Gln-Arg-His |
| SEQ. ID. NO. 20 | Asp-Phe-Glu-Glu-Ile-Pro-Glu-Glu-Tyr-Leu-Gln |
| SEQ. ID. NO. 21 | Trp-Asp-Pro-Arg-Pro-Gln-Arg-His-(CamCKK)-Asp-Phe-Glu-Glu-Ile-Pro-Glu-Glu-Tyr-Leu-Gln |
| SEQ. ID. NO. 22 | Val-Arg-Phe-Thr-Asp-Gly-Glu-Gly-Thr-Pro-Lys-Pro-Gln-Ser-His-Asn-Asn-Gly-Asp-Phe-Glu-Glu-Ile-Pro-Glu-Glu-Tyr-Leu-Gln (mini-hirudin 1) |
| SEQ. ID. NO. 23 | Ile-Arg-Phe-Thr-Asp-Gly-Glu-Gly-Thr-Pro-Asn-Pro-Glu-Ser-His-Asn-Asn-Gly-Asp-Phe-Glu-Glu-Ile-Pro-Glu-Glu-Tyr-Leu-Gln (mini-hirudin 2) |
| SEQ. ID. NO. 24 | Ala-Lys-Val-Thr-Met-Thr-Cys-Ser-Ala-Ser- |
| SEQ. ID. NO. 25 | Ile-Arg-Phe-Thr-Asp-Gly-Ala-Lys-Val-Thr-Met-Thr-Cys-Ser-Ala-Ser-Gly-Asp-Phe-Glu-Glu-Ile-Pro-Glu-Glu-Tyr-Leu-Gln |
| SEQ. ID. NO. 26 | ISXPXXFXHXXHVGXD |
| SEQ. ID. NO. 27 | -Ser-Gly-Ser-Gly- |
| SEQ. ID. NO. 28 | -Arg-Lys-Ser-Leu-Thr-Ile-Tyr-Ala-Gln-Val-Gln-Lys- |
| SEQ. ID. NO. 29 | Bbs-Arg-(D-Pip)-Gly-(Ser-Pro-His-Tyr(P)-Glu-Lys-Val-Ser-Gly)n-Asp-Phe-Glu-Glu-Ile-Pro-Glu-Glu-Tyr-Leu-Gln |
| SEQ. ID. NO. 30 | Gly-Ser-Val-Val-Pro-Arg-Pro-Gln-Gln-Leu-His-Asn-Asp-Gly-Asp-Phe-Glu-Glu-Ile-Pro-Glu-Glu-Tyr-Leu-Gln |
| SEQ. ID. NO. 31 | Gly-Ser-His-Ala-Pro-Arg-Pro-Gln-Ile-His-Asn-Asp-Gly-Asp-Phe-Glu-Glu-Ile-Pro-Glu-Glu-Tyr-Leu-Gln |
| SEQ. ID. NO. 32 | Bbs-Arg-(D-Pip)-Gly-Ser-Val-Val-Pro-Arg-Pro-Gln-Leu-His-Asn-Asp-Gly-Asp-Phe-Glu-Glu-Ile-Pro-Glu-Glu-Tyr-Leu-Gln |

TABLE 3-continued

| SEQ. ID. NO. | SEQUENCE |
| --- | --- |
| SEQ. ID. NO. 33 | Bbs-Arg-(D-Pip)-Gly-Ser-His-Ala-Pro-Arg-Pro-Gln-Ile-His-Asn-Asp-Gly-Asp-Phe-Glu-Glu-Ile-Pro-Glu-Glu-Tyr-Leu-Gln |
| SEQ. ID. NO. 34 | Gly-Ser-Val-Val-Pro-Asn-Xxx-Xxx-Leu-Xxx-Xxx-Asp-Gly-Asp-Phe-Glu-Glu-Ile-Pro-Glu-Glu-Tyr-Leu-Gln |
| SEQ. ID. NO. 35 | Bbs-Arg-(D-Pip)-Gly (H1, Bbs = 4-tert-butyl-benzenesulfonyl, D-Pip = D-pipecolic acid, $K_I$ in low μM range |
| SEQ. ID. NO. 36 | Gly-Asp-Phe-Glu-Glu-Ile-Pro-Glu-Glu-Tyr-Leu-Gln |
| SEQ. ID. NO. 37 | -Gly-Gly-Asn-Ser-Gly-Val-Ser-Gly-Pro-Ile-Asn-Phe-Thr-His-Lys-Val-His-Val-Gly-Phe-Asp-Pro-Ala-Ser-Gly-Asn-Phe-Thr-Gly-Leu-Pro-Asp-Thr-Trp-Lys-Ser-Leu-Leu-Gln-His-Ser-Lys-Ile-Thr- |
| SEQ. ID. NO. 38 | -Glu-Val-Asn-Ile-Lys-Ile-Ser-Thr-Pro-Phe-Asn-Ala-Lys-His-Leu-Ala-His-Val-Gly-Ile-Asp-Asp-Asn-Gly-Ser-Tyr-Thr-Gly-Leu-Pro-Ile-Glu-Trp-Glu-Arg-Leu-Leu-Ser-Ala-Ser-Gly-Ile-Thr-; |
| SEQ. ID. NO. 39 | -Thr-Leu-Asp-Leu-Asn-Thr-Pro-Val-Asp-Lys-Thr-Ser-Asn- |
| SEQ. ID. NO. 40 | -Ser-Val-Val-Pro-Arg-Pro-Gln-Leu-His-Asn-Asp- |
| SEQ. ID. NO. 41 | -Ser-His-Ala-Pro-Arg-Pro-Gln-Ile-His-Asn-Asp- |
| SEQ. ID. NO. 42 | -Asn-Gly-Arg-Lys-Ile-Cys-Leu-Asp-Leu-Gln-Ala-Pro-Leu-Tyr-Lys-Lys-Ile-Ile-Lys-Lys-Leu-Leu-Glu-Ser- |
| SEQ. ID. NO. 43 | -Asn-Gly-Arg-Lys-Ile-Cys-Leu-Glu-Leu-Arg-Ala-Pro-Leu-Tyr-Lys-Lys-Ile-Ile-Lys-Lys-Leu-Leu-Glu-Ser- |
| SEQ. ID. NO. 44 | -His-His-Leu-Gly-Gly-Ala-Lys-Gln-Ala-Gly-Asp-Val- |
| SEQ. ID. NO. 45 | -Tyr-Met-Glu-Ser-Arg-Ala-Asp-Arg- |
| SEQ. ID. NO. 46 | -Gln-Ser-His-Asn-Arg- |
| SEQ. ID. NO. 47 | -(Cys)-COOH<br>\|<br>S<br>/<br>S<br>\|<br>NH$_2$-(Cys)-(Gly-Ser)$_8$-Gly- |
| SEQ. ID. NO. 48 | -(Cys)-COOH<br>\|<br>S<br>/<br>S<br>\|<br>NH$_2$-(Cys)-Asp-Lys-Asn-Ala-Asp-Gly-Trp-Ile-Asp-Asn- |
| SEQ. ID. NO. 49 | -Asp-Lys-Asn-Ala-Asp-Gly-Trp-Ile-Asp-Asn-Gly-Glu-Phe-Glu- |
| SEQ. ID. NO. 50 | -(Gly-Ser)$_2$- |
| SEQ. ID. NO. 51 | -(Gly-Ser)$_4$- |
| SEQ. ID. NO. 52 | -(Gly-Ser)$_6$- |
| SEQ. ID. NO. 53 | -(Gly-Ser)$_8$- |
| SEQ. ID. No. 54 | -(Gly-Ser)$_{10}$- |
| SEQ. ID. NO. 55 | -(Gly-Ser)$_{12}$- |
| SEQ. ID. NO. 56 | -(Gly-Ser)$_{14}$- |
| SEQ. ID. NO. 57 | -Gly-Cys . . . Cys-(Gly-Ser)$_8$- |
| SEQ. ID. NO. 58 | -(Gly-Ser)$_4$-Gly-Lys-(Gly-Ser)$_5$- |
| SEQ. ID. NO. 59 | -Ser-Pro-His-Tyr-Glu-Lys-Val-Ser-Gly- |
| SEQ. ID. NO. 60 | -(Ser-Pro-His-Tyr-Glu-Lys-Val-Ser-Gly)$_2$- |
| SEQ. ID. NO. 61 | -Ser-Pro-His-Tyr(P)-Glu-Lys-Val-Ser-Gly- |
| SEQ. ID. NO. 62 | -(Ser-Pro-His-Tyr(P)-Glu-Lys-Val-Ser-Gly)$_2$- |
| SEQ. ID. NO. 63 | -Pro-His-Tyr-Glu-Lys-Val-Ser- |
| SEQ. ID. NO. 64 | -Pro-His-Tyr-Glu-Lys-Val-Ser-Gly-Ser-Pro-His-Tyr-Glu-Lys-Val-Ser- |
| SEQ. ID. NO. 65 | -Pro-His-Tyr(P)-Glu-Lys-Val-Ser- |
| SEQ. ID. NO. 66 | -Pro-His-Tyr(P)-Glu-Lys-Val-Ser-Gly-Ser-Pro-His-Tyr(P)-Glu-Lys-Val-Ser- |
| SEQ. ID. NO. 67 | -Ser-Val-Val-Pro-Asn-Aaa-Bbb-Leu-Ccc-Ddd-Asp- |
| SEQ. ID. NO. 68 | Bbs-Arg-(D-Pip) |
| SEQ. ID. NO. 69 | Val-Arg-Phe-Thr-Asp-Gly-Glu-Gly-Thr-Pro-Lys |
| SEQ. ID. NO. 70 | Val-Arg-Phe-Thr-Asp |
| SEQ. ID. NO. 71 | Ile-Arg-Phe-Thr-Asp-Gly-Glu-Gly-Thr-Pro-Asn |
| SEQ. ID. NO. 72 | Ile-Arg-Phe-Thr-Asp |
| SEQ. ID. NO. 73 | Bbs-Arg-(D-Pip)-(Gly-Ser)$_2$-Gly-Asp-Phe-Glu-Glu-Ile-Pro-Glu-Glu-Tyr-Leu-Gln |
| SEQ. ID. NO. 74 | Bbs-Arg-(D-Pip)-(Gly-Ser)$_4$-Gly-Asp-Phe-Glu-Glu-Ile-Pro-Glu-Glu-Tyr-Leu-Gln |
| SEQ. ID. NO. 75 | Bbs-Arg-(D-Pip)-(Gly-Ser)$_6$-Gly-Asp-Phe-Glu-Glu-Ile-Pro-Glu-Glu-Tyr-Leu-Gln |
| SEQ. ID. NO. 76 | Bbs-Arg-(D-Pip)-(Gly-Ser)$_8$-Gly-Asp-Phe-Glu-Glu-Ile-Pro-Glu-Glu-Tyr-Leu-Gln |
| SEQ. ID. NO. 77 | Bbs-Arg-(D-Pip)-(Gly-Ser)$_{10}$-Gly-Asp-Phe-Glu-Glu-Ile-Pro-Glu-Glu-Tyr-Leu-Gln |
| SEQ. ID. NO. 78 | Bbs-Arg-(D-Pip)-(Gly-Ser)$_{12}$-Gly-Asp-Phe-Glu-Glu-Ile-Pro-Glu-Glu-Tyr-Leu-Gln |
| SEQ. ID. NO. 79 | Bbs-Arg-(D-Pip)-(Gly-Ser)$_{14}$-Gly-Asp-Phe-Glu-Glu-Ile-Pro-Glu-Glu-Tyr-Leu-Gln |
| SEQ. ID. NO. 80 | Bbs-Arg-(D-Pip)-Gly-Ser-Pro-His-Tyr-Glu-Lys-Val-Ser-Gly-Asp-Phe-Glu-Glu-Ile-Pro-Glu-Glu-Tyr-Leu-Gln |
| SEQ. ID. NO. 81 | Bbs-Arg-(D-Pip)-Gly-(Ser-Pro-His-Tyr-Glu-Lys-Val-Ser-Gly)$_2$-Asp-Phe-Glu-Glu-Ile-Pro-Glu-Glu-Tyr-Leu-Gln |
| SEQ. ID. NO. 82 | Bbs-Arg-(D-Pip)-Gly-Ser-Pro-His-Tyr(P)-Glu-Lys-Val-Ser-Gly-Asp-Phe-Glu-Glu-Ile-Pro-Glu-Glu-Tyr-Leu-Gln |

TABLE 3-continued

| SEQ. ID. NO. | SEQUENCE |
|---|---|
| SEQ. ID. NO. 83 | Bbs-Arg-(D-Pip)-Gly-(Cys)-COOH<br>\|<br>S<br>/<br>S<br>\|<br>NH₂-(Cys)-(Gly-Ser)₈-Gly-Asp-Phe-Glu-Glu-Ile-Pro-Glu-Glu-Tyr-Leu-Gln; |
| SEQ. ID. NO. 84 | Bbs-Arg-(D-Pip)-(Gly-Ser)₄-Gly-Lys-(Gly-Ser)₅-Gly-Asp-Phe-Glu-Glu-Ile-Pro-Glu-Glu-Tyr-Leu-Gln |
| SEQ. ID. NO. 85 | Bbs-Arg-(D-Pip)-Gly-Thr-Leu-Asp-Leu-Asn-Thr-Pro-Val-Asp-Lys-Thr-Ser-Asn-Gly-Asp-Phe-Glu-Glu-Ile-Pro-Glu-Glu-Tyr-Leu-Gln |
| SEQ. ID. NO. 86 | Bbs-Arg-(D-Pip)-Gly-Asn-Gly-Arg-Lys-Ile-Cys-Leu-Asp-Leu-Gln-Ala-Pro-Leu-Tyr-Lys-Lys-Ile-Ile-Lys-Lys-Leu-Leu-Glu-Ser-Gly-Asp-Phe-Glu-Glu-Ile-Pro-Glu-Glu-Tyr-Leu-Gln |
| SEQ. ID. NO. 87 | Bbs-Arg-(D-Pip)-Gly-Asn-Gly-Arg-Lys-Ile-Cys-Leu-Glu-Leu-Arg-Ala-Pro-Leu-Tyr-Lys-Lys-Ile-Ile-Lys-Lys-Leu-Leu-Glu-Ser-Gly-Asp-Phe-Glu-Glu-Ile-Pro-Glu-Glu-Tyr-Leu-Gln |
| SEQ. ID. NO. 88 | Bbs-Arg-(D-Pip)-Gly-His-His-Leu-Gly-Gly-Ala-Lys-Gln-Ala-Gly-Asp-Val-Gly-Asp-Phe-Glu-Glu-Ile-Pro-Glu-Glu-Tyr-Leu-Gln |
| SEQ. ID. NO. 89 | Bbs-Arg-(D-Pip)-Gly-Tyr-Met-Glu-Ser-Arg-Ala-Asp-Arg-Gly-Asp-Phe-Glu-Glu-Ile-Pro-Glu-Glu-Tyr-Leu-Gln |
| SEQ. ID. NO. 90 | Bbs-Arg-(D-Pip)-Gly-Gln-Ser-His-Asn-Arg-Gly-Asp-Phe-Glu-Glu-Ile-Pro-Glu-Glu-Tyr-Leu-Gln |
| SEQ. ID. NO. 91 | Bbs-Arg-(D-Pip)-Gly-(Cys)-COOH<br>\|<br>S<br>/<br>S<br>\|<br>NH₂-(Cys)-<br>Asp-Lys-Asn-Ala-Asp-Gly-Trp-Ile-Asp-Asn-Gly-Asp-Phe-Glu-Glu-Ile-Pro-Glu-Glu-Tyr-Leu-Gln |
| SEQ. ID. NO. 92 | Gly-Gly-Asn-Ser-Gly-Val-Ser-Gly-Pro-Ile-Asn-Phe-Thr-His-Lys-Val-His-Val-Gly-Phe-Asp-Pro-Ala-Ser |
| SEQ. ID. NO. 93 | Gly-Gly-Asn-Ser-Gly-Val-Ser-Gly-Pro-Ile-Asn-Phe-Thr-His-Lys-Val-His-Val-Gly-Phe-Asp |
| SEQ. ID. NO. 94 | Glu-Val-Asn-Ile-Lys-Ile-Ser-Thr-Pro-Phe-Asn-Ala-Lys-His-Leu-Ala-His-Val-Gly-Ile-Asp-Asp-Asn-Gly |
| SEQ. ID. NO. 95 | Glu-Val-Asn-Ile-Lys-Ile-Ser-Thr-Pro-Phe-Asn-Ala-Lys-His-Leu-Ala-His-Val-Gly-Ile-Asp |
| SEQ. ID. NO. 96 | Gly-Asn-Phe-Thr-Gly-Leu-Pro-Asp-Thr-Trp-Lys-Ser-Leu-Leu-Gln-His-Ser-Lys-Ile-Thr |
| SEQ. ID. NO. 97 | Asn-Phe-Thr-Gly-Leu-Pro-Asp-Thr-Trp-Lys-Ser-Leu-Leu-Gln-His-Ser-Lys-Ile-Thr |
| SEQ. ID. NO. 98 | Gly-Ser-Tyr-Thr-Gly-Leu-Pro-Ile-Glu-Trp-Glu-Arg-Leu-Leu-Ser-Ala-Ser-Gly-Ile-Thr |
| SEQ. ID. NO. 99 | Ser-Tyr-Thr-Gly-Leu-Pro-Ile-Glu-Trp-Glu-Arg-Leu-Leu-Ser-Ala-Ser-Gly-Ile-Thr |
| SEQ. ID. NO. 100 | Gly-Gly-Asn-Ser-Gly-Val-Ser-Gly-Pro-Ile-Asn-Phe-Thr-His-Lys-Val-His-Val-Gly-Phe-Asp-Ser-Gly-Ser-Gly-Asn-Phe-Thr-Gly-Leu-Pro-Asp-Thr-Trp-Lys-Ser-Leu-Leu-Gln-His-Ser-Lys-Ile-Thr |
| SEQ. ID. NO. 101 | Gly-Gly-Asn-Ser-Gly-Val-Ser-Gly-Pro-Ile-Asn-Phe-Thr-His-Lys-Val-His-Val-Gly-Phe-Asp-Arg-Lys-Ser-Leu-Thr-Ile-Tyr-Ala-Gln-Val-Gln-Lys-Asn-Phe-Thr-Gly-Leu-Pro-Asp-Thr-Trp-Lys-Ser-Leu-Leu-Gln-His-Ser-Lys-Ile-Thr |
| SEQ. ID. NO. 102 | Bbs-R-dPip-Gly-Arg-Lys-Ser-Leu-Thr-Ile-Tyr-Ala-Gln-Val-Gln-Lys-Gly-Asp-Phe-Glu-Glu-Ile-Pro-Glu-Glu-Tyr-Leu-Gln |
| SEQ. ID. NO. 103 | Gly-Thr-Leu-Asp-Leu-Asn-Thr-Pro-Val-Asp-Lys-Thr-Ser-Asn- |
| SEQ. ID. NO. 104 | Gly-Ser-His-Ala-Pro-Arg-Pro-Gln-Ile-His-Asn-Asp- |
| SEQ. ID. NO. 105 | Gly-Ser-Val-Val-Pro-Arg-Pro-Gln-Leu-His-Asn-Asp- |
| SEQ. ID. NO. 106 | Gly-His-His-Leu-Gly-Gly-Ala-Lys-Gln-Ala-Gly-Asp-Val- |
| SEQ. ID. NO. 107 | Gly-Tyr-Met-Glu-Ser-Arg-Ala-Asp-Arg- |
| SEQ. ID. NO. 108 | Gly-Gln-Ser-His-Asn-Arg- |
| SEQ. ID. NO. 109 | Ac-Asp-Lys-Asn-Ala-Asp-Gly-Trp-Ile-Asp-Asn-Gly-Glu-Phe-Glu-NH₂ |
| SEQ. ID. NO. 110 | Ac-Asp-Lys-Asn-Ala-Asp-Gly-Trp-Ile-Asp-Asn-Gly-Asp-Phe-Glu-NH₂ |
| SEQ. ID. NO. 111 | Leu-Ile-Glu-Asp-Ile-Cys-Leu-Pro-Arg-Trp-Gly-Cys-Leu-Trp-Glu-Asp |
| SEQ. ID. NO. 112 | Bbs-Arg-(D-Pip)-Gly-Leu-Ile-Glu-Asp-Ile-Cys-Leu-Pro-Arg-Trp-Gly-Cys-Leu-Trp-Glu-Asp-Gly-Asp-Phe-Gln-Gln-Ile-Pro-Glu-Glu-Tyr-Leu-Gln |
| SEQ. ID. NO. 113 | ((Gly-Ser)n-Gly-Asp-Phe-Glu-Glu-Ile-Pro-Glu-Glu-Tyr-Leu-Gln) |
| SEQ. ID. NO. 114 | Cys-Asp-Lys-Asn-Ala-Asp-Gly-Trp-Ile-Asp-Asn-Gly-Asp-Phe-Glu-Glu-Ile-Pro-Glu-Glu-Tyr-Leu-Gln |
| SEQ. ID. NO. 115 | Bbs-R-(D-Pip)-Gly-(Ser-Pro-His-B-Glu-Lys-Val-Ser-Gly)₂-Asp-Phe-Glu-Glu-Ile-Pro-Glu-Glu-Tyr-Leu-Gln |
| SEQ. ID. NO. 116 | Ile-Arg-Phe-Thr-Asp-Gly-Glu-Gly |
| SEQ. ID. NO. 117 | Ile-Arg-Phe-Thr-Asp-Gly-Glu-Gly-(CamCKK)-Asp-Phe-Glu-Glu-Ile-Pro-Glu-Glu-Tyr-Leu-Gln |
| SEQ. ID. NO. 118 | (Val-Pro-Gly-Val-Gly)19-Val-Pro-Gly-Val |

TABLE 3-continued

| SEQ. ID. NO. | SEQUENCE |
| --- | --- |
| SEQ. ID. NO. 119 | Bbs-Arg-dPip-Gly-(Val-Pro-Gly-Val-Gly)20-Asp-Phe-Glu-Glu-Ile-Pro-Glu-Glu-Tyr-Leu-Gln |
| SEQ. ID. NO. 120 | Gly-(Val-Pro-Gly-Val-Gly)19-Val-Pro-Gly-Val |
| SEQ. ID. NO. 121 | Ile-Arg-Phe-Thr-Asp-Gly-Glu-Gly-(Val-Pro-Gly-Val-Gly)20-Asp-Phe-Glu-Glu-Ile-Pro-Glu-Glu-Leu-Gln |
| SEQ. ID. NO. 122 | Bbs-Arg-dPip-Gly |
| SEQ. ID. NO. 123 | Gly-Ser-Pro-His-Tyr-Glu-Lys-Val-Ser |
| SEQ. ID. NO. 124 | Gly-Ser-Pro-His-Tyr(P)-Glu-Lys-Val-Ser |
| SEQ. ID. NO. 125 | Gly-Ser-Pro-His-Tyr-Glu-Lys-Val-Ser-Gly-Ser-Pro-His-Tyr-Glu-Lys-Val-Ser |
| SEQ. ID. NO. 126 | Gly-Ser-Pro-His-Tyr(P)-Glu-Lys-Val-Ser-Gly-Ser-Pro-His-Tyr(P)-Glu-Lys-Val-Ser |
| SEQ. ID. NO. 127 | Gly-Glu-Gln-Lys-Leu-Ile-Ser-Glu-Glu-Asp-Leu |
| SEQ. ID. NO. 128 | Gly-Arg-Lys-Ser-Leu-Thr-Ile-Tyr-Ala-Gln-Val-Gln-Lys |
| SEQ. ID. NO. 129 | -Ser-Pro-His-Tyr(P)-Glu-Lys-Val-Ser-Gly- |
| SEQ. ID. NO. 130 | GGNSGFPGPI NFTHKVHVGF DRKSLTIYAQ VQKNFTGLPD TWKSLLQHSK IT |
| SEQ. ID. NO. 131 | YGRKKRRQRR RGGNSGFPGP INFTHKVHVG FDRKSLTIYA QVQKNFTGLP |
| SEQ. ID. NO. 132 | GSSHHHHHHSSFNPRGSWYY GNVTRHQAECALNERGVEGDFLIRDSE SSPSDFSVSLKASGRNKHFKVQL VDSVYCIGQRRFHSMDELVEHYKKAP IFTSEHGEKLYLVRALQ |
| SEQ. ID. NO. 133 | GSSHHHHHHSSFNPRGSD AVAVYHGKISRETGEKLLLATGLDG SYLLRDSESVPGVYCLCVLYHGYI YTYRVSQTETGSWSAETAPGVHKRYF RKIKNLISAFQKPDQGIVIPLQVPVEK |
| SEQ. ID. NO. 134 | GSSHHHHHHSSGLVPRGSHMQTIKCV VGDGAVGKTCLLISYTTSKFPA DYVPTVFDNYAVTVMIGDEPFTLGLF DTAGQEDYDRLRPLSYPSTDV FLVCFSVISPASFENVKEKWFPEVHHH CPGVPIIIVGTQTDLRNDDVI LQRLHRQKLSPITQEQGEKLAKELKA VKYVECSALTQRGLKTVFDEAIVAALE |

TABLE 4

Full sequences of recombinant peptides and proteins 1. eCla4-SLAM
GGNSGFPGPI NFTHKVHVGF DRKSLTIYAQ VQKNFTGLPD
TWKSLLQHSK IT
(SEQ. ID. NO. 130)

2. TAT-eCla4-SLAM:
YGRKKRRQRR RGGNSGFPGP INFTHKVHVG FDRKSLTIYA
QVQKNFTGLP DTWKSLLQHS KIT
(SEQ. ID. NO. 131)

TABLE 4-continued

Full sequences of recombinant peptides and proteins

3. Grb4-SH2
GSSHHHHHHSSFNPRGSWYYGNVTRHQAECALNERGVEGDFLIRDSESSP
SDFSVSLKASGRNKHFKVQLVDSVYCIGQRRFHSMDELVEHYKKAP IFT
SEHGEKLYLVRALQ
(SEQ. ID. NO. 132)

4. SAP-SH2:
GSSHHHHHH SSFNPRGSD AVAVYHGKISR ETGEKLLLATGLDG
SYLLRDSESVPGVYCLC VLYHGYI YTYRVSQT ETGSWSAE
TAPGVHKRYF RKIKNLI SAFQ KPDQGI VIPLQYPVEK
(SEQ. ID. NO. 133)

5. CaCdc42 (R150K)
GSSHHHHHHS SGLVPRGSH MQTIKCVV VGDGAVG KTCLLISY
TTSKFPA DYVPTVF DNYAVT VMIGDE PFTLGLF DTAGQED
YDRLRPL SYPSTDV FLVCFSV ISPASF ENVKEKW FPEVHHH
CPGVPII IVGTQTD LRNDDVI LQRLHRQ KLSPIT QEQGEKLA
KELKA VKYVEC SALTQRGLKT VFDEA IVAALE
(SEQ. ID. NO. 134)

6. CaM-DTI:
WDPRPQRHADQLTEEQIAEFKEAFSLFDKDGDGTITTKELGTVMRSLGQN
PTEAELQDMINEVDADGNGTIDFPEFLTMMARKMKDTGGVKLIPSWTTVI
LVKSMLRKRSFGNPFGGDSEEEIREAFRVFDKDGNGYISAAELRHVMTNL
GEKLTDEEVDEMIREADIDGDGQVNYEEFVQMMTAKDFEEIPEEYLQ
(SEQ. ID. NO. 21)

7. CaM-DTI2:
IRFTDGEGADQLTEEQIAEFKEAFSLFDKDGDGTITTKELGTVMRSLGQN
PTEAELQDMINEVDADGNGTIDFPEFLTMMARKMKDNGGVKLIPSWTTVI
LVKSMLRKRSFGNPFGGDSEEEIREAFRVFDKDGNGYIRAAELRHVMTNL
GEKLTDEEVDEMIREADIDGDGQVNYEEFVQMMTAKDFEEIPEEYLQ
(SEQ. ID. NO. 117)

REFERENCE LIST

1. Anderson, P. J.; Nesset, A.; Dharmawardana, K. R.; and Bock, P. E., 2000, Characterization of proexosite I on prothrombin: J. Biol. Chem., 275, 16428-16434.
2. Bright, J. N., Woolf, T. B., Hoh, J. H., 2001, Predicting properties of intrinsically unstructured proteins. Prog. Biophys. Mol. Biol., 76, 131-173.
3. Burbelo, P. D., Drechsel, D., and Hall, A., 1995, A conserved binding motif defines numerous candidate target proteins for both Cdc42 and Rac GTPases: J. Biol. Chem. 270, 29071-29074.
4. Dennis, M. S., Zhang, M., Meng, Y. G., Kadkhodayan, M., Kirchhofer, D., Combs, D., and Damico, L. A., 2002, Albumin binding as a general strategy for improving the pharmacokinetics of proteins: J. Biol. Chem., 277, 35035-35043.
5. Diella, F., Cameron, S., Gemund, C., Linding, R., Via, A., Kuster, B., Sicheritz-Ponten, T., Blom, N., and Gibson, T. J., 2004, Phospho. ELM: a database of experimentally verified phosphorylation sites in eukaryotic proteins: BMC. Bioinformatics., 5, 79.
6. DiMaio, J., Gibbs, B., Munn, D., Lefebvre, J., Ni, F., and Konishi, Y., 1990, Bifunctional thrombin inhibitors based on the sequence of hirudin45-65: J. Biol. Chem., 265, 21698-21703.
6. Gill, S. C. and von Hippel, P. H., 1989, Calculation of protein extinction coefficients from amino acid sequence data: Anal. Biochem., 182, 319-326.
7. Gizachew, D. and Oswald, R. E., 2001, Concerted motion of a protein-peptide complex: backbone dynamics studies of an (15)N-labeled peptide derived from P(21)-activated kinase bound to Cdc42Hs.GMPPCP: Biochemistry 40, 14368-14375.

8. Hamad-Schifferli, K., Schwartz, J. J., Santos, A. T., Zhang, S., and Jacobson, J. M., 2002, Remote electronic control of DNA hybridization through inductive coupling to an attached metal nanocrystal antenna: Nature, 415, 152-155.
9. Hilpert, K., Hansen, G., Wessner, H., Kuttner, G., Welfie, K., Seifert, M., and Hohne, W., 2001, Anti-c-myc antibody 9E10: epitope key positions and variability characterized using peptide spot synthesis on cellulose: Protein Eng, 14, 803-806.
10. Jordan, Andreas, Scholz, Regina, Wust, Peter, Fahling, Horst, and Roland, Felix, 1999, Magnetic fluid hyperthermia (MFH): Cancer treatment with AC magnetic field induced excitation of biocompatible superparamagnetic nanoparticles: Journal of Magnetism and Magnetic Materials, 201, 413-419.
11. Leonard, D. A., Satoskar, R. S., Wu, W. J., Bagrodia, S., Cerione, R. A., and Manor, D., 1997, Use of a fluorescence spectroscopic readout to characterize the interactions of Cdc42Hs with its target/effector, mPAK-3: Biochemistry 36, 1173-1180.
11. Lin, Y., Padmapriya, A., Morden, K. M., and Jayasena, S. D., 1995, Peptide conjugation to an in vitro-selected DNA ligand improves enzyme inhibition: Proc. Natl. Acad. Sci. U.S.A, 92, 11044-11048.
12. McPherson, D. T., Morrow, C., Minehan, D. S., Wu, J., Hunter, E., and Urry, D. W., 1992, Production and purification of a recombinant elastomeric polypeptide, G-(VPGVG)19-VPGV, from *Escherichia coli*: Biotechnol. Prog., 8, 347-352.
12. Ni, F., Ning, Q., Jackson, C. M., and Fenton, J. W., 1993, Thrombin exosite for fibrinogen recognition is partially accessible in prothrombin: J. Biol. Chem., 268, 16899-16902.
13. Nomanbhoy, T. and Cerione, R. A., 1999, Fluorescence assays of Cdc42 interactions with target/effector proteins: Biochemistry 38, 15878-15884.
14. Osborne, M. J., Su, Z., Sridaran, V., and Ni, F., 2003, Efficient expression of isotopically labeled peptides for high resolution NMR studies: application to the Cdc42/Rac binding domains of virulent kinases in *Candida albicans*: J. Biomol. NMR 26, 317-326.
15. Pawson, T. and Linding, R., 2005, Synthetic modular systems—reverse engineering of signal transduction: FEBS Lett., 579, 1808-1814.
16. Pawson, T. and Nash, P., 2003, Assembly of cell regulatory systems through protein interaction domains: Science, 300, 445-452.
15. Polonelli, L.; Magliani, W.; Conti, S.; Bracci, L.; Lozzi, L.; Neri, P.; Adriani, D.; De Bernardis, F.; Cassone, A., 2003, Therapeutic activity of an engineered synthetic killer antiidiotypic antibody fragment against experimental mucosal and systemic candidiasis: Infect. Immun. 71, 6205-6212.
18. Puntervoll, P., Linding, R., Gemund, C., Chabanis-Davidson, S., Mattingsdal, M., Cameron, S., Martin, D. M., Ausiello, G., Brannetti, B., Costantini, A., Ferre, F., Maselli, V., Via, A., Cesareni, G., Diella, F., Superti-Furga, G., Wyrwicz, L., Ramu, C., McGuigan, C., Gudavalli, R., Letunic, I., Bork, P., Rychlewski, L., Kuster, B., Helmer-Citterich, M., Hunter, W. N., Aasland, R., and Gibson, T. J., 2003, ELM server: A new resource for investigating short functional sites in modular eukaryotic proteins: Nucleic Acids Res., 31, 3625-3630.
16. Rudolph, M. G., Bayer, P., Abo, A., Kuhlmann, J., Vetter, I. R., and Wittinghofer, A., 1998, The Cdc42/Rac interactive binding region motif of the Wiskott Aldrich syndrome protein (WASP) is necessary but not sufficient for tight binding to Cdc42 and structure formation: J. Biol. Chem. 273, 18067-18076.
17. Slon-Usakiewicz, J. J., Sivaraman, J., Li, Y., Cygler, M., and Konishi, Y., 2000, Design of P1' and P3' residues of trivalent thrombin inhibitors and their crystal structures: Biochemistry, 39, 2384-2391.
18. Su, Z.; Vinogradova, A.; Koutychenko, A.; Tolkatchev, D.; and Ni, F., 2004a, Rational design and selection of bivalent peptide ligands of thrombin incorporating P4-P1 tetrapeptide sequences: from good substrates to potent inhibitors: Protein Eng. Des. Sel., 17, 647-657.
19. Su, Z., Xu, P., and Ni, F., 2004b, Single phosphorylation of Tyr304 in the cytoplasmic tail of ephrin B2 confers high-affinity and bifunctional binding to both the SH2 domain of Grb4 and the PDZ domain of the PDZ-RGS3 protein: Eur. J. Biochem., 271, 1725-1736.
20. Thompson, G., Owen, D., Chalk, P. A., and Lowe, P. N., 1998, Delineation of the Cdc42/Rac-binding domain of p21-activated kinase: Biochemistry 37, 7885-7891.
21. Tolkatchev, D., Xu, P., and Ni, F., 2003a, Probing the kinetic landscape of transient peptide-protein interactions by use of peptide (15)n NMR relaxation dispersion spectroscopy: binding of an antithrombin peptide to human prothrombin: J. Am. Chem. Soc., 125, 12432-12442.
22. Truong, K., Sawano, A., Mizuno, H., Hama, H., Tong, K. I., Mal, T. K., Miyawaki, A., and Ikura, M., 2001, FRET-based in vivo Ca2+ imaging by a new calmodulin-GFP fusion molecule: Nat. Struct. Biol., 8, 1069-1073.
22 Urry, D. W., 1997, Physical Chemistry of Biological Free Energy Transduction As Demonstrated by Elastic Protein-Based Polymers: J. Phys. Chem. B., 101, 11007-11028.
23. Witting, J. I., Bourdon, P., Brezniak, D. V., Maraganore, J. M. and Fenton, J. W., 1992, Thrombin-specific inhibition by and slow cleavage of hirulog-1: Biochem. J., 283 (Pt 3), 737-743.
34. Pirone, D. M., Carter, D. E., and Burbelo, P. D. 2001, Evolutionary Expansion of CRIB-Containing Cdc42 Effector Proteins. Trends in Genetics, 17, 370-373.
35. Li, S. C., Gish, G., Yang, D., Coffey, A. J., Forman-Kay, J. D., Ernberg, I., Kay, L. E. and Pawson, T. 1999, Novel Mode of Ligand Binding by the SH2 Domain of the Human XLP Disease Gene Product SAP/SH2D1A. Curr. Biol. 9, 1355-1362.
36. Covic, J., Gresser, A. L., Talavera, J., Swift, S., and Kuliopulos, A. 2002, Activation and Inhibition of G Protein-Coupled Receptors by Cell-Penetrating Membrane-Tethered Peptides. Proc. Natl. Acad. Sci., 99, 643-648.

The invention claimed is:

1. A molecule that binds thrombin and has the general formula of BM1-L-BM2, wherein:
   BM1 is a first thrombin binding moiety consisting of the amino acid sequence as set forth in SEQ ID NO: 4, SEQ ID NO: 19, SEQ ID NO: 35, SEQ ID NO: 69, SEQ ID NO: 70, SEQ ID NO: 71, SEQ ID NO: 72 or SEQ ID NO: 116, said first thrombin binding moiety having an affinity for a catalytic active site of thrombin;
   BM2 is a second thrombin binding moiety consisting of the amino acid sequence as set forth in SEQ ID NO: 20, said second thrombin binding moiety having an affinity for an exosite of thrombin that is not the catalytic active site; and
   L is a linker joining BM1 and BM2, said linker consisting of the amino acid sequence as set forth in SEQ ID NO: 17, SEQ ID NO: 48, SEQ ID NO: 49, SEQ ID NO: 109, SEQ ID NO: 110 or amino acids 9 to 186 of SEQ ID NO: 117, wherein said linker binds a calcium ion and undergoes a change in flexibility in response to the binding of the calcium ion,
   wherein BM1 and BM2 are selected such that each of the BM1 and BM2 existing separately has a lower binding affinity than the complex of BM1 and BM2 does when they are linked to form the molecule.

2. A pharmaceutical composition comprising a molecule of claim 1 with a carrier.

3. The molecule of claim 1, wherein the linker consists of the amino acid sequence as set forth in SEQ ID NO: 48, SEQ ID NO: 49, SEQ ID NO: 109 or SEQ ID NO: 110.

4. The molecule of claim 1 wherein the linker consists of the amino acid sequence as set forth in amino acids 9 to 186 of SEQ ID NO: 117.

5. The molecule of claim 1 wherein the linker consists of the amino acid sequence as set forth in SEQ ID NO: 17.

6. The molecule of claim 1, wherein the molecule consists of the amino acid sequence as set forth in SEQ ID NO: 21 or SEQ ID NO: 117.

7. The molecule of claim 1, wherein the molecule consists of the amino acid sequence as set forth in SEQ ID NO: 117.

* * * * *